(12) United States Patent
Archetti et al.

(10) Patent No.: US 9,726,933 B2
(45) Date of Patent: Aug. 8, 2017

(54) LIQUID-CRYSTAL DISPLAYS AND LIQUID-CRYSTALLINE MEDIA HAVING HOMEOTROPIC ALIGNMENT

(71) Applicant: Merck Patent GmbH, Darmstadt (DE)

(72) Inventors: Graziano Archetti, Darmstadt (DE); Andreas Taugerbeck, Darmstadt (DE); Renate Bender, Darmstadt (DE); Rocco Fortte, Frankfurt am Main (DE); Peer Kirsch, Seeheim-Jugenheim (DE); Izumi Saito, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/652,568

(22) PCT Filed: Nov. 26, 2013

(86) PCT No.: PCT/EP2013/003563
§ 371 (c)(1),
(2) Date: Jun. 16, 2015

(87) PCT Pub. No.: WO2014/094959
PCT Pub. Date: Jun. 26, 2014

(65) Prior Publication Data
US 2015/0301368 A1    Oct. 22, 2015

(30) Foreign Application Priority Data
Dec. 17, 2012 (EP) .................................. 12008389

(51) Int. Cl.
| | | |
|---|---|---|
| *G02F 1/1333* | (2006.01) | |
| *G02F 1/1337* | (2006.01) | |
| *C09K 19/06* | (2006.01) | |
| *C09K 19/56* | (2006.01) | |
| *C07C 31/27* | (2006.01) | |
| *C07C 33/26* | (2006.01) | |
| *C07C 33/36* | (2006.01) | |
| *C07C 43/23* | (2006.01) | |
| *C09K 19/34* | (2006.01) | |
| *C09K 19/54* | (2006.01) | |
| *G02F 1/1343* | (2006.01) | |
| *C09K 19/04* | (2006.01) | |
| *C09K 19/12* | (2006.01) | |
| *C09K 19/30* | (2006.01) | |

(52) U.S. Cl.
CPC ............ *G02F 1/1337* (2013.01); *C07C 31/27* (2013.01); *C07C 31/276* (2013.01); *C07C 33/26* (2013.01); *C07C 33/36* (2013.01); *C07C 43/23* (2013.01); *C09K 19/063* (2013.01); *C09K 19/3003* (2013.01); *C09K 19/3402* (2013.01); *C09K 19/542* (2013.01); *C09K 19/56* (2013.01); *G02F 1/134363* (2013.01); *C07C 2101/14* (2013.01); *C09K 2019/0444* (2013.01); *C09K 2019/0448* (2013.01); *C09K 2019/122* (2013.01); *C09K 2019/123* (2013.01); *C09K 2019/301* (2013.01); *C09K 2019/304* (2013.01); *C09K 2019/3009* (2013.01); *C09K 2019/3016* (2013.01); *C09K 2019/3036* (2013.01); *C09K 2019/3063* (2013.01); *C09K 2019/3422* (2013.01); *G02F 2001/133742* (2013.01)

(58) Field of Classification Search
CPC .. C09K 19/063; C09K 19/56; C09K 19/3003; C09K 19/3402; C09K 19/542; C09K 2019/0444; C09K 2019/0448; C09K 2019/122; C09K 2019/123; C09K 2019/3009; C09K 2019/3036; C09K 2019/304; C09K 2019/3063; C09K 2019/301; C09K 2019/3016; C09K 2019/3422; G02F 1/1333; G02F 2001/133742; C07C 31/27; C07C 31/276; C07C 33/26; C07C 33/36; C07C 43/23
USPC .................... 252/299.01, 299.6; 349/182
See application file for complete search history.

(56) References Cited

U.S. PATENT DOCUMENTS

| | | |
|---|---|---|
| 3,848,966 A | 11/1974 | Smith et al. |
| 3,981,816 A | 9/1976 | Moriyama et al. |
| (Continued) | | |

FOREIGN PATENT DOCUMENTS

| | | |
|---|---|---|
| DE | 269856 A1 | 7/1989 |
| DE | 285103 A5 | 12/1990 |
| (Continued) | | |

OTHER PUBLICATIONS

International Search Report dated Feb. 10, 2014 issued in corresponding PCT/EP2013/003563 application (pp. 1-4).
(Continued)

*Primary Examiner* — Geraldina Visconti
(74) *Attorney, Agent, or Firm* — Millen White Zelano and Branigan, PC; Richard Traverso; Csaba Henter

(57) ABSTRACT

The present invention relates to liquid-crystalline media (LC media) having negative or positive dielectric anisotropy comprising self-alignment additives (SAMs) with an at least one bifunctional or polyfunctional anchor group, which effects the homeotropic (vertical) alignment of the LC media at a surface or the cell walls of a liquid-crystal display (LC display). The invention therefore also encompasses LC displays having homeotropic alignment of the liquid-crystalline medium (LC medium) without conventional imide alignment layers. The LC media may be supplemented by a polymerizable or polymerized component, which serves for stabilization of the alignment, for adjustment of the tilt angle and/or as passivation layer.

24 Claims, No Drawings

(56) References Cited

U.S. PATENT DOCUMENTS

| | | | |
|---|---|---|---|
| 7,846,903 B2 | 12/2010 | Hato et al. | |
| 9,120,970 B2* | 9/2015 | Archetti | C09K 19/42 |
| 9,234,135 B2* | 1/2016 | Archetti | C09K 19/44 |
| 2008/0113923 A1 | 5/2008 | Hatoh et al. | |
| 2013/0114034 A1 | 5/2013 | Archetti et al. | |
| 2013/0148069 A1 | 6/2013 | Archetti et al. | |
| 2013/0182202 A1 | 7/2013 | Graziano et al. | |

FOREIGN PATENT DOCUMENTS

| | | |
|---|---|---|
| DE | 102011108708 A1 | 3/2012 |
| EP | 1813287 A1 | 8/2007 |
| JP | 4506105 B2 | 5/2010 |
| NO | 2012/007107 A1 | 1/2012 |
| TW | 201221629 A1 | 6/2012 |
| WO | 2006/015683 A1 | 2/2006 |
| WO | 2012/038026 A1 | 3/2012 |

OTHER PUBLICATIONS

Partial English Translation of JP 4506105 B2 published May 14, 2010.

B. Neumann et al., "Molecular Design of Amphotropic Materials: Influence of Oligooxyethylene Groups on the Mesogenic Properties of Calamitic Liquid Crystals", Journal of Materials Chemistry, vol. 6, No. 7 (Jul. 1, 1996) pp. 1087-1098.

Chinese Office Action dated Sep. 9, 2016 issued in corresponding CN 201380065433.9 application (8 pages).

\* cited by examiner

LIQUID-CRYSTAL DISPLAYS AND LIQUID-CRYSTALLINE MEDIA HAVING HOMEOTROPIC ALIGNMENT

The present invention relates to liquid-crystalline media (LC media) having negative or positive dielectric anisotropy comprising self-alignment additives with an at least one bifunctional or polyfunctional anchor group, which effects the homeotropic (vertical) alignment of the LC media at a surface or the cell walls of a liquid-crystal display (LC display). The invention therefore also encompasses LC displays having homeotropic alignment of the liquid-crystalline medium (LC medium) without conventional imide alignment layers. The LC media may be supplemented by a polymerizable or polymerized component, which serves for stabilisation of the alignment, for adjustment of the tilt angle and/or as passivation layer.

The principle of electrically controlled birefringence, the ECB effect or also DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). This was followed by papers by J. F. Kahn (Appl. Phys. Lett. 20 (1972), 1193) and G. Labrunie and J. Robert (J. Appl. Phys. 44 (1973), 4869).

The papers by J. Robert and F. Clerc (SID 80 Digest Techn. Papers (1980), 30), J. Duchene (Displays 7 (1986), 3) and H. Schad (SID 82 Digest Techn. Papers (1982), 244) showed that liquid-crystalline phases must have high values for the ratio of the elastic constants $K_3/K_1$, high values for the optical anisotropy $\Delta n$ and values for the dielectric anisotropy of $\Delta\epsilon \leq -0.5$ in order to be suitable for use in high-information display elements based on the ECB effect. Electro-optical display elements based on the ECB effect have homeotropic edge alignment (VA technology=vertically aligned).

Displays which use the ECB effect, as so-called VAN (vertically aligned nematic) displays, for example in the MVA (multi-domain vertical alignment, for example: Yoshide, H. et al., paper 3.1: "MVA LCD for Notebook or Mobile PCs . . . ", SID 2004 International Symposium, Digest of Technical Papers, XXXV, Book I, pp. 6 to 9, and Liu, C. T. et al., paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, paper 15.4: "Super PVA Sets New State-of-the-Art for LCD-TV", SID 2004 International Symposium, Digest of Technical Papers, XXXV, Book II, pp. 760 to 763), ASV (advanced super view, for example: Shigeta, Mitzuhiro and Fukuoka, Hirofumi, paper 15.2: "Development of High Quality LCDTV", SID 2004 International Symposium, Digest of Technical Papers, XXXV, Book II, pp. 754 to 757) modes, have established themselves as one of the three more recent types of liquid-crystal display that are currently the most important, in particular for television applications, besides IPS (in-plane switching) displays (for example: Yeo, S. D., paper 15.3: "An LC Display for the TV Application", SID 2004 International Symposium, Digest of Technical Papers, XXXV, Book II, pp. 758 & 759) and the long-known TN (twisted nematic) displays. The technologies are compared in general form, for example, in Souk, Jun, SID Seminar 2004, seminar M-6: "Recent Advances in LCD Technology", Seminar Lecture Notes, M-6/1 to M-6/26, and Miller, Ian, SID Seminar 2004, seminar M-7: "LCD-Television", Seminar Lecture Notes, M-7/1 to M-7/32. Although the response times of modern ECB displays have already been significantly improved by addressing methods with over-drive, for example: Kim, Hyeon Kyeong et al., paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular on switching of grey shades, is still a problem which has not yet been satisfactorily solved.

Considerable effort is associated with the production of VA displays having two or more domains of different preferential direction. It is an aim of this invention to simplify the production processes and the display devices themselves without giving up the advantages of VA technology, such as relatively short response times and good viewing-angle dependence.

VA displays which comprise LC media having positive dielectric anisotropy are described in S. H. Lee et al. *Appl. Phys. Lett.* (1997), 71, 2851-2853. These displays use interdigital electrodes arranged on a substrate surface (in-plane addressing electrode configuration having a comb-shaped structure), as employed, inter alia, in the commercially available IPS (in-plane switching) displays (as disclosed, for example, in DE 40 00 451 and EP 0 588 568), and have a homeotropic arrangement of the liquid-crystal medium, which changes to a planar arrangement on application of an electric field (VA-IPS).

Further developments of the above-mentioned display can be found, for example, in K. S. Hun et al. *J. Appl. Phys.* (2008), 104, 084515 (DSIPS: 'double-side in-plane switching' for improvements of driver voltage and transmission), M. Jiao et al. *App. Phys. Lett* (2008), 92, 111101 (DFFS: 'dual fringe field switching' for improved response times) and Y. T. Kim et al. *Jap. J. App. Phys.* (2009), 48, 110205 (VAS: 'viewing angle switchable' LCD).

In addition, VA-IPS displays are also known under the name positive-VA and HT-VA.

In all such displays (referred to below in general as VA-IPS displays), an alignment layer is applied to both substrate surfaces for homeotropic alignment of the LC medium; the production of this layer has hitherto been associated with considerable effort.

It is an aim of this invention to simplify the production processes themselves without giving up the advantages of VA-IPS technology, such as relatively short response times, good viewing-angle dependence and high contrast.

Industrial application of these effects in electro-optical display elements requires LC phases, which have to satisfy a multiplicity of requirements. Particularly important here are chemical resistance to moisture, air, the materials in the substrate surfaces and physical influences, such as heat, infrared, visible and ultraviolet radiation and direct and alternating electric fields.

Furthermore, industrially usable LC phases are required to have a liquid-crystalline mesophase in a suitable temperature range and low viscosity.

VA and VA-IPS displays are generally intended to have very high specific resistance at the same time as a large working-temperature range, short response times and a low threshold voltage, with the aid of which various grey shades can be produced.

In conventional VA and VA-IPS displays, a polyimide layer on the substrate surfaces ensures homeotropic alignment of the liquid crystal. The production of a suitable alignment layer in the display requires considerable effort. In addition, interactions of the alignment layer with the LC medium may impair the electrical resistance of the display. Owing to possible interactions of this type, the number of suitable liquid-crystal components is considerably reduced. It would therefore be desirable to achieve homeotropic alignment of the LC medium without polyimide.

The disadvantage of the active-matrix TN displays frequently used is due to their comparatively low contrast, the relatively high viewing-angle dependence and the difficulty of producing grey shades in these displays.

VA displays have significantly better viewing-angle dependences and are therefore used principally for televisions and monitors.

A further development are the so-called PS (polymer sustained) or PSA (polymer sustained alignment) displays, for which the term "polymer stabilised" is also occasionally used. The PSA displays are distinguished by the shortening of the response times without significant adverse effects on other parameters, such as, in particular, the favourable viewing-angle dependence of the contrast.

In these displays, a small amount (for example 0.3% by weight, typically <1% by weight) of one or more polymerizable compound(s) is added to the LC medium and, after introduction into the LC cell, is polymerized or crosslinked in situ, usually by UV photopolymerization, between the electrodes with or without an applied electrical voltage. The addition of polymerizable mesogenic or liquid-crystalline compounds, also known as reactive mesogens or "RMs", to the LC mixture has proven particularly suitable. PSA technology has hitherto been employed principally for LC media having negative dielectric anisotropy.

Unless indicated otherwise, the term "PSA" is used below as representative of PS displays and PSA displays.

In the meantime, the PSA principle is being used in diverse classical LC displays. Thus, for example, PSA-VA, PSA-OCB, PSA-IPS, PSA-FFS and PSA-TN displays are known. The polymerization of the polymerizable compound(s) preferably takes place with an applied electrical voltage in the case of PSA-VA and PSA-OCB displays, and with or without an applied electrical voltage in the case of PSA-IPS displays. As can be demonstrated in test cells, the PS(A) method results in a 'pretilt' in the cell. In the case of PSA-OCB displays, for example, it is possible for the bend structure to be stabilized so that an offset voltage is unnecessary or can be reduced. In the case of PSA-VA displays, the pretilt has a positive effect on the response times. A standard MVA or PVA pixel and electrode layout can be used for PSA-VA displays. In addition, however, it is also possible, for example, to manage with only one structured electrode side and no protrusions, which significantly simplifies production and at the same time results in very good contrast at the same time as very good light transmission.

PSA-VA displays are described, for example, in JP 10-036847 A, EP 1 170 626 A2, U.S. Pat. No. 6,861,107, U.S. Pat. No. 7,169,449, US 2004/0191428 A1, US 2006/0066793 A1 and US 2006/0103804 A1. PSA-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221. PSA-VA-IPS displays are disclosed, for example, in WO 2010/089092 A1.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors or "TFTs"), while in the case of passive-matrix displays, individual pixels are usually addressed by the multiplex method, both methods being known from the prior art.

In particular for monitor and especially TV applications, optimization of the response times, but also of the contrast and luminance (i.e. also transmission), of the LC display is still sought after. The PSA method can provide crucial advantages here. In particular in the case of PSA-VA displays, a shortening of the response times, which correlate with a pretilt which can be measured in test cells, can be achieved without significant adverse effects on other parameters.

In the prior art, polymerizable compounds of the following formula, for example, are used for PSA-VA:

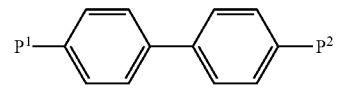

in which P denotes a polymerizable group, usually an acrylate or methacrylate group, as described, for example, in U.S. Pat. No. 7,169,449.

The effort for the production of a polyimide layer, treatment of the layer and improvement with bumps or polymer layers is relatively great. A simplifying technology compatible with (PSA-)VA/VA-IPS which on the one hand reduces production costs and on the other hand helps to optimize the image quality (viewing-angle dependence, contrast, response times) would therefore be desirable.

The document WO 2012/038026 A1 discloses self-aligning mesogens (SAMs) with a hydroxy group attached to a mesogenic core structure comprising two or more rings.

The existing approaches for achieving display applications without a polyimide layer could be still improved.

The present invention relates firstly to an LC medium comprising a low-molecular-weight liquid-crystalline component and one or more self-alignment additives of formula I, $$R^1\text{-}A^1\text{-}(Z^2\text{-}A^2)_{m1}\text{-}R^2 \tag{I}$$

wherein
$R^2$ denotes a group

    (A1)

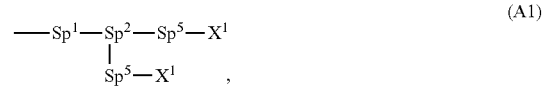    (A2)

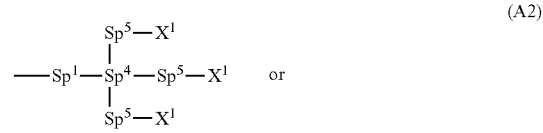 or

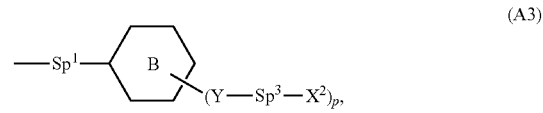    (A3)

$Sp^1$, $Sp^3$, $Sp^5$ independently of each other, denotes a spacer group or a single bond,
$Sp^2$ denotes a trivalent, acyclic spacer group, preferably a group CH, $CR^0$ or N,
$Sp^4$ denotes a tetravalent, acyclic spacer group, preferably a carbon atom, Y is independently of each other O, S, (CO), $NR^0$ or a single bond, $X^1$ and $X^2$ independently of each other a group —OH, $-NH_2$, $-NHR^{11}$, —SH, $-SR^{11}$, $-NR^{11}_2$, $-OR^{11}$ or —(CO)OH,

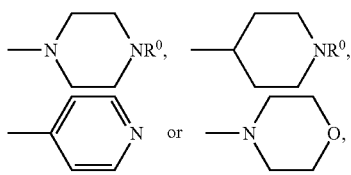

$R^{11}$ in each case independently denotes a halogenated or unsubstituted alkyl having 1 to 15 C atoms, where, in addition, one or more $CH_2$ groups in this alkyl may each be replaced, independently of one another, by $-C\equiv C-$, $-CH=CH-$, $-(CO)O-$, $-O(CO)-$, $-(CO)-$ or —O— in such a way that O or N atoms are not linked directly to one another, and where two radicals $R^{11}$ are optionally linked to one another to form a ring,
preferably $R^{11}$ is alkyl with 1 to 7 C atoms, more preferably $CH_3$ or $CH_2CH_3$, B any ring or condensed ring, optionally substituted by one, two or three substituents $R^L$, preferably a six-membered ring, particularly preferred benzene, where the optional substituents of said benzene reside in place of any of the positions of hydrogen atoms, p 2, 3, 4 or 5, preferably 2 or 3, $A^1$ and $A^2$ each, independently of one another, denote an aromatic, heteroaromatic, alicyclic or heterocyclic group, preferably having 4 to 25 C atoms, which may also contain fused rings, and which may also be mono- or polysubstituted by $R^L$, $R^L$ in each case, independently of one another, denotes OH, SH, $SR^0$, $-(CH_2)_{n1}-OH$, F, Cl, Br, I, —CN, $-NO_2$, —NCO, —NCS, —OCN, —SCN, $-C(=O)N(R^0)_2$, $-C(=O)R^0$, $-N(R^0)_2$, $-(CH_2)_{n1}-N(R^0)_2$, optionally substituted silyl, optionally substituted aryl or cycloalkyl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F or Cl, and two vicinal $R^L$ together are optionally =O(carbonyl O), n1 denotes 1, 2, 3 or 4, $Z^2$ in each case, independently of one another, denotes a single bond, —O—, —S—, —CO—, —CO—O—, —OCO—, —O—CO—O—, $-OCH_2-$, $-CH_2O-$, $-SCH_2-$, $-CH_2S-$, $-CF_2O-$, $-OCF_2-$, $-CF_2S-$, $-SCF_2-$, $-(CH_2)_{n1}-$, $-CF_2CH_2-$, $-CH_2CF_2-$, $-(CF_2)_{n1}-$, —CH=CH—, —CF=CF—, —C≡C—, —CH=CH—COO—, —OCO—CH=CH— or $CR^0R^{00}$, preferably a single bond or $-CH_2CH_2-$, $R^0$ and $R^{00}$ each, independently of one another, denote H or alkyl having 1 to 12 C atoms, $R^1$ denotes H, halogen, straight-chain, branched or cyclic alkyl having 1 to 25 C atoms, in which, in addition, one or more non-adjacent $CH_2$ groups may be replaced by —C≡C—, —CH=CH—, $-NR^0-$, —O—, —S—, —CO—, —CO—O—, —O—CO—, —O—CO—O— in such a way that N, O and/or S atoms are not linked directly to one another, and in which, in addition, one or more tertiary carbon atoms (CH groups) may be replaced by N, and in which, in addition, one or more H atoms may be replaced by F or Cl, and m1 denotes 0, 1, 2, 3, 4 or 5, preferably 1 or 2.

The liquid-crystalline component or the LC medium can have either positive or negative dielectric anisotropy. The LC medium according to the invention is preferably nematic.

In addition, the LC medium preferably comprises a polymerized or polymerizable component, where the polymerized component is obtainable by polymerization of a polymerizable component.

This polymer component enables the LC medium and in particular its alignment to be stabilized, a passivation layer to be built, and a desired pretilt optionally to be established.

The present invention furthermore relates to a process for the preparation of an LC medium in which a low-molecular-weight liquid-crystalline component is mixed with one or more of said self-alignment additives, and one or more polymerizable compounds and/or auxiliary substances are optionally added. The liquid-crystalline component or the LC medium can have either positive or negative dielectric anisotropy.

The present invention furthermore relates to a liquid-crystal display (LC display) comprising a liquid-crystal cell (LC cell) having two parallel, planar substrates and at least two electrodes, where at least one substrate is transparent to light and at least one substrate has one or two electrodes, and a layer of a liquid-crystal medium (LC medium), located between the substrates, comprising a low-molecular-weight liquid-crystalline component and one or more of said self-alignment additives suitable for effecting homeotropic (vertical) alignment of the LC medium with respect to the substrate surfaces.

In addition, the LC medium of the LC display preferably comprises a polymerized or polymerizable component, where the polymerized component is obtainable by polymerization of one or more polymerizable compounds in the LC medium between the substrates of the LC cell, optionally with application of an electrical voltage to the electrodes of the cell or under the action of another electric field.

The invention furthermore relates to a process for the production of an LC display, preferably of the PSA-VA(-IPS) type, comprising an LC cell having two substrates and at least two electrodes, where at least one substrate is transparent to light and at least one substrate has one or two electrodes, comprising the process steps of:

filling of the cell with an LC medium as described above and below or in the claims, comprising one or more self-alignment additives which is suitable for effecting the homeotropic (vertical) alignment of the LC medium with respect to the substrate surfaces, and optionally polymerization of a polymerizable component optionally present, optionally with application of a voltage to the electrodes of the cell or under the action of another electric field.

The invention furthermore relates to new compounds summarized under formula I above and below, in particular with the preferred meanings of the substituents.

The aforementioned self-alignment additive is dissolved or dispersed in the liquid crystal mixture. It effects the homeotropic alignment of the liquid crystal with respect to the substrate surfaces (such as, for example, a $SiN_x$ or glass surface or an ITO- or polyimide- or photoresist-coated surface). Considering the investigations for this invention, it appears that the polar anchor group interacts with the substrate surface. The additive, after interaction with the substrate surface, consequently aligns relative to the boundaries of the mixture and induces homeotropic alignment of the liquid crystal.

The self-alignment additive is preferably employed in a concentration of <5% by weight, more preferably <3% by weight and particularly <1% by weight, and most preferably <0.5% by weight. The use of 0.1 to 0.5% by weight of the self-alignment additive generally results in a complete homeotropic alignment of the LC layer for conventional cell thicknesses (3 to 4 μm) and for the substrate materials used in the display industry. Other surfaces, e.g. by special treatments, may allow to further reduce the amount of additive (<0.1 wt %) while keeping up the alignment or may also allow to increase the amount of additive (>5 wt %) without affecting the display performance.

The polar anchor group $R^2$ of the self-alignment additive preferably comprises hydroxy or amino groups which presumably undergo a non-covalent interaction with the glass, metal-oxide or polymer substrate surface. The groups should at the same time be sufficiently stable for use as LC medium. In addition, they should have only little effect on the VHR values ('voltage holding ratio') of the LC medium. Hydroxy groups are therefore preferred.

The polar anchor group $R^2$ preferably contains two or three, particularly two OH groups or two or three, particularly two N atoms, where the N atoms are in a primary, secondary or tertiary amino group.

The anchor group $R^2$ of formula I thus encompasses, for example, preferably a pair of hydroxy groups or a pair of amino groups, which are connected to each other and to the mesogenic core (the group $R^1$-$A^1$-$(Z^2$-$A^2)_{m1}$-) by a polyvalent organic group consisting of a branching part provided by the polyvalent spacer $Sp^2$, $Sp^4$ or a ring B, as further described for the group $R^2$, and optional further bivalent spacers ($Sp^1$, $Sp^5$, —Y-$Sp^3$) between each of these structural elements. The structure of the anchor group $R^2$ hence may be branched, cyclic or a combination thereof.

The term "spacer group", or "Sp", as used herein, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the terms "spacer group" or "spacer" as used herein will be understood to mean a group which connects two or more different parts of a molecule.

A divalent spacer of formula $Sp^1$ or $Sp^3$ or $Sp^5$ as used herein independently preferably denotes one of the meanings indicated for group Sp, where Sp denotes alkylene having 1 to 20, preferably 1 to 12, more preferably 1 to 6, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^0$$R^{00}$)—, —CO—, —CO—O—, —O—CO—, —O—CO—O—, —S—CO—, —CO—S—, —N($R^0$)—CO—O—, —O—CO—N($R^0$)—, —N($R^0$)—CO—N($R^0$)—, —CH=CH— or —C≡C— in such a way that O, N and/or S atoms are not linked directly to one another, and $R^0$ and $R^{00}$ each, independently of one another, denote H or alkyl having 1 to 12 C atoms.

The group $R^2$ in the above formulae preferably denotes a group of the formula (A1), (A2) or (A3), as shown above, wherein independently the following definitions are preferred:

Sp$^1$ denotes —$(CH_2)_n$—, —$(CH_2)_nO$—, —$O(CH_2)_n$—, —O—, —S—, —$NR^0$—, —C≡C—, —C=C—

$(CH_2)_n$—, —CH=CH— or —CH=CH—$(CH_2)_n$—, where n is 1 to 6, or a single bond,
more preferably —$CH_2$—, —$CH_2CH_2$—, —$CH_2O$—, —$OCH_2$—, —$CH_2CH_2CH_2$—, —$CH_2CH_2O$—, —$OCH_2CH_2$—, —C≡C—$(CH_2)_n$—, —O—, or a single bond, most preferably not a single bond for structure (A1) and (A2), and preferably a single bond for structure (A3), $Sp^2$ is CH or N, $Sp^3$ is —$(CH_2)_n$—, —$(CH_2CH_2O)_{q1}$—$CH_2CH_2$—, —$CH_2CH_2$—S—$CH_2CH_2$—, —$CH_2CH_2$—NH—$CH_2CH_2$— or —$(SiR^0R^{00}$—$O)_{p1}$—, in which n is an integer from 1 to 12, q1 is an integer from 1 to 3, and $R^0$ and $R^{00}$ have the meanings indicated above,
more preferably —$(CH_2)_n$—, $Sp^4$ is a tetravalent carbon atom, $Sp^5$ is —$(CH_2)_n$—, —$(CH_2)_n$—O—$(CH_2)_m$—, wherein n is 1 to 6, preferably 1, and m is 1, 2, 3, 4, 5 or 6, more preferably $Sp^5$ is —$CH_2$—, p is 2 or 3, preferably 2, and the both chains may have independent compositions, $X^1$, $X^2$ independently denote a group —OH, —$NH_2$, —$NHR^{11}$, —$NR^{11}_2$, —(CO)OH or a group of the formula

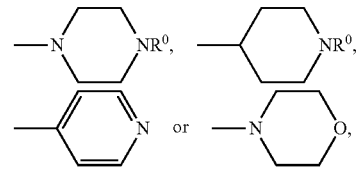

wherein $R^0$ is defined as above and preferably denotes H, more preferably $X^1$, $X^2$ denote —OH or —$NH_2$, especially OH, and n independently denotes 1, 2, 3 or 4.

For the compounds of formula I wherein $R^2$ is a group (A1) or (A2), the spacer $Sp^1$ is preferably not a single group. Further,

in formula I and its closer defined formulae preferably denotes a benzene ring. Ring B more preferably denotes a substituted benzene selected from the following formulae, where the bonds indicate the substituted positions

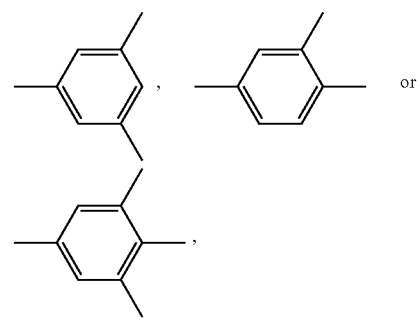

The group $R^2$ in the formulae above and below particularly preferably denotes a group of the sub-formula (A1a), (A2a), (A3a) or (A3b),

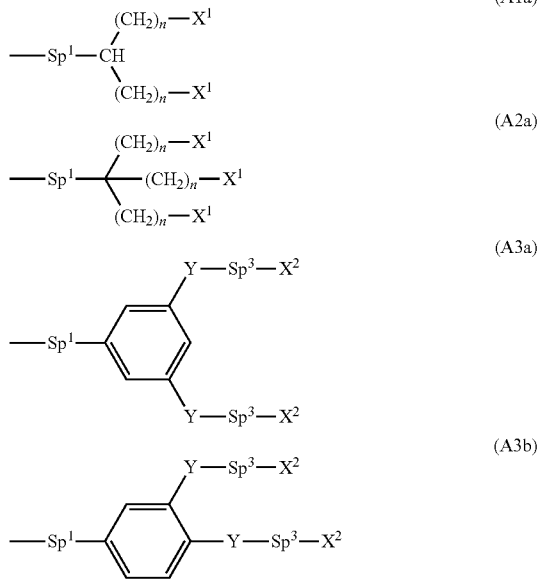

in which the variable groups are independently defined as above and below, and
n independently denotes 1, 2, 3 or 4, preferably 1,
while formulae (A1a) and (A3a) are particularly preferred.

The term "aryl" or "aromatic group" denotes an aromatic carbon group or a group derived there from. The term "heteroaryl" denotes "aryl" as defined above containing one or more heteroatoms.

Aryl and heteroaryl groups may be monocyclic or polycyclic, i.e. they may contain one ring (such as, for example, phenyl) or two or more rings, which may also be fused (such as, for example, naphthyl) or covalently bonded (such as, for example, biphenyl), or contain a combination of fused and bonded rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, pyrene, dihydropyrene, chrysene, perylene, tetracene, pentacene, benzo-pyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenan-thrimidazole, pyridimidazole, pyrazinimidazole, quinoxalinimidazole, benzoxazole, naphthoxazole, anthroxazole, phenanthroxazole, isoxazole, benzo-thiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothio-phene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The alicyclic and heterocyclic groups, which are non-aromatic, may be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]pentane-1,3-diyl, bicyclo[2.2.2]octane-1,4-diyl, spiro[3.3]heptane-2,6-diyl, octa-hydro-4,7-methanoindane-2,5-diyl and perhydrocyclopenta[a]phenanthrene-3,7-diyl.

The rings $A^1$ and $A^2$ in formula I above and below preferably denote each, independently of one another, a radical selected from the following groups:
a) the group consisting of 1,4-phenylene and 1,3-phenylene, in which, in addition, one or two CH groups may be replaced by N and in which, in addition, one or more H atoms may be replaced by $R^L$,
b) the group consisting of trans-1,4-cyclohexylene, 1,4-cyclo-hexenylene and 1,4'-bicyclohexylene, in which, in addition, one or more non-adjacent $CH_2$ groups may be replaced by —O— and/or —S— and in which, in addition, one or more H atoms may be replaced by F or Cl,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may, in addition, be mono- or polysubstituted by $R^L$,
d) the group consisting of saturated, partially unsaturated or fully unsaturated, and optionally substituted, polycyclic radicals having 5 to 20 cyclic C atoms, one or more of which may also be replaced by heteroatoms, preferably selected from the group consisting of 3,3'-bicyclobutylidene, bicyclo[1.1.1]pentane-1,3-diyl, bicyclo[2.2.2]octane-1,4-diyl, spiro[3.3]heptane-2,6-diyl, indane-2,5-diyl, perhydrocyclopenta[a]phenanthrene-3,17-diyl (in particular gonane-3,17-diyl),

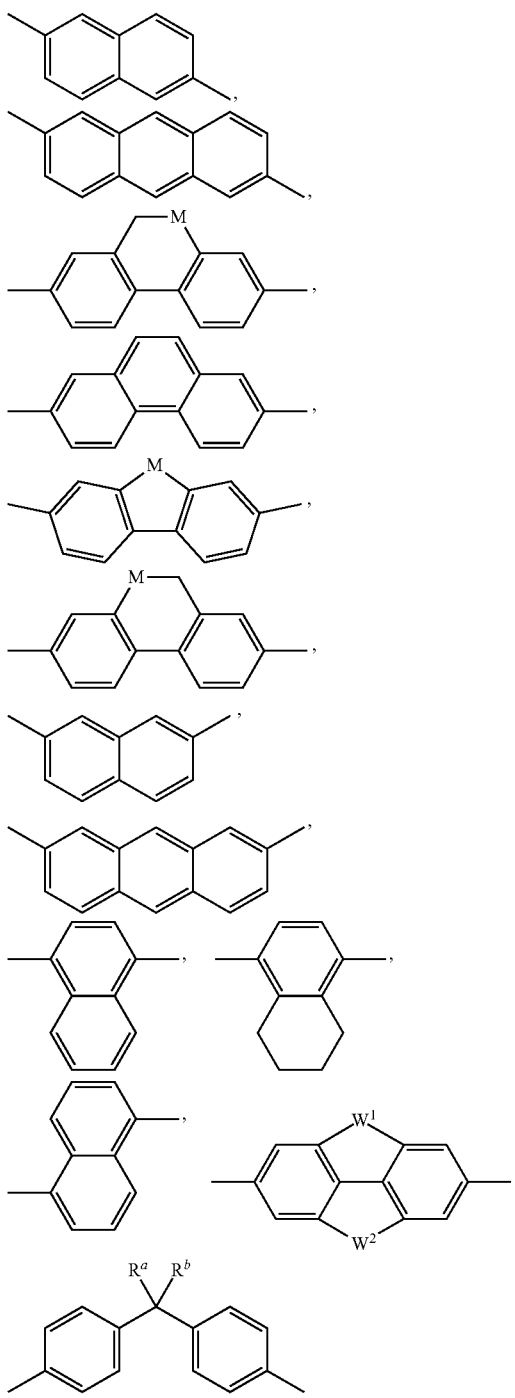

where, in addition, one or more H atoms in these radicals may be replaced by $R^L$, and/or one or more double bonds may be replaced by single bonds, and/or one or more CH groups may be replaced by N, $R^a$, $R^b$ each, independently of one another, denote H, F or straight-chain or branched alkyl having 1 to 12 C atoms, in which, in addition, one or more H atoms may be replaced by F, or together form a carbocyclic ring system, M denotes —O—, —S—, —$CH_2$—, —$CHY^1$— or —$CY^1Y^2$—, and $Y^1$ and $Y^2$ each, independently of one another, have one of the meanings indicated above for $R^0$, or denote Cl or CN, one of the groups Y' and $Y^2$ alternatively also denotes —$OCF_3$, preferably denote H, F, Cl, CN or $CF_3$.

The rings $A^1$ and $A^2$ particularly preferably denote
  each, independently of one another, 1,4-phenylene, 1,3-phenylene, 1,2-phenylene, where, in addition, one or more CH groups in these groups may be replaced by N, or cyclohexane-1,4-diyl, or cyclohexane-1,3-diyl, in which, in addition, one or more non-adjacent $CH_2$ groups may be replaced by 0, where all these groups may be unsubstituted or mono- or polysubstituted by a group $R^L$, most preferably $A^1$ and $A^2$ denote 1,4-phenylene optionally substituted by $R^L$ or cyclohexane-1,4-diyl.

Above and below $R^L$ preferably denotes on each occurrence, identically or differently, F, Cl, CN, or straight-chain or branched, in each case optionally fluorinated alkyl, alkoxy, alkylcarbonyl, alkoxycarbonyl, alkylcarbonyloxy or alkoxycarbonyloxy having 1 to 12 C atoms.

More preferably in formula I, each independently of one another, m1 denotes 1, 2 or 3 for acyclic anchor groups and 1 or 2 for anchor groups of formula (A2) comprising the ring B, and $A^1$ and $A^2$ independently denote 1,4-phenylene, 1,3-phenylene or cyclohexane-1,4-diyl.

In connection with the present invention, the term "alkyl" denotes a straight-chain or branched, saturated or unsaturated, preferably saturated, aliphatic hydrocarbon radical having 1 to 15 (i.e. 1, 2, 3, 4, 5, 6, 7, 8, 9, 10, 11, 12, 13, 14 or 15) carbon atoms.

The term "cyclic alkyl" encompasses alkyl groups which have at least one carbocyclic part, i.e., for example, also cycloalkylalkyl, alkylcycloalkyl and alkylcycloalkylalkyl. The carbocyclic groups encompass, for example, cyclopropyl, cyclobutyl, cyclopentyl, cyclohexyl, cycloheptyl, cyclooctyl, etc.

"Halogen" in connection with the present invention stands for fluorine, chlorine, bromine or iodine, preferably for fluorine or chlorine.

Particularly preferred compounds of the formula I are selected from the following illustrative compounds, which at the same time represent particularly preferred groups $A^1$, $A^2$, $Z^2$ and $R^2$ and preferred combinations of two or more of these groups (e.g. the group -$A^1$-($Z^2$-$A^2$)$_{m1}$-) of the self-alignment additives:

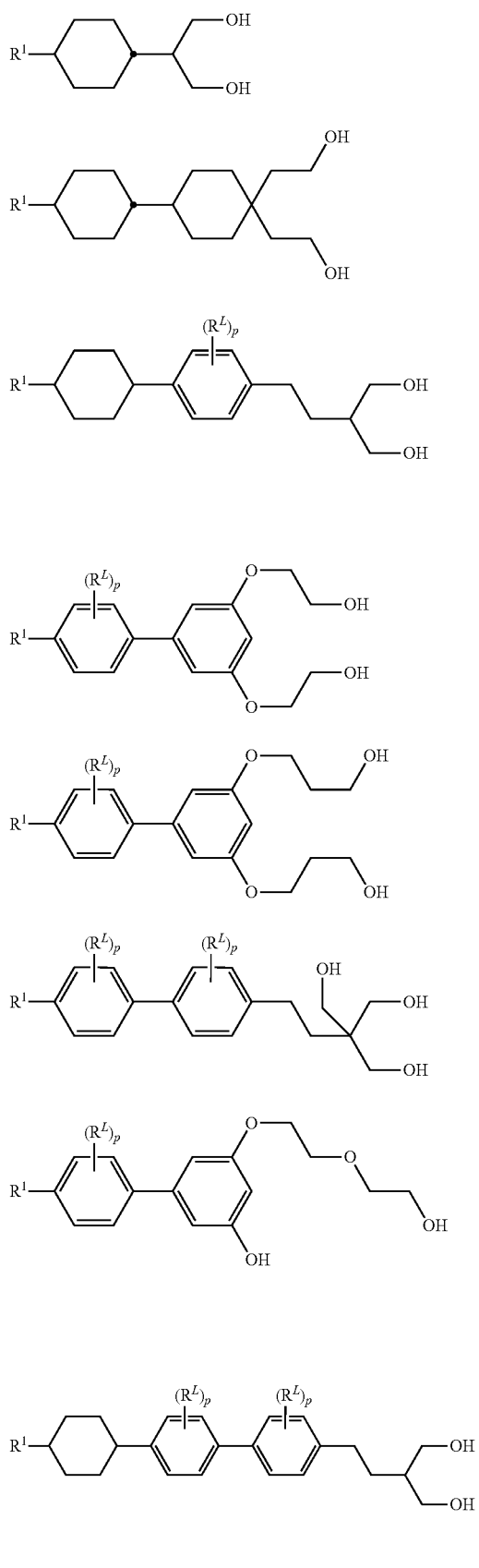

I-17
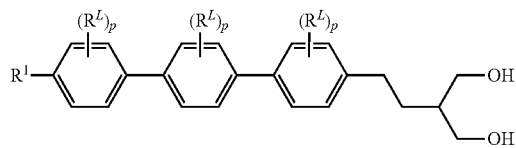
I-18
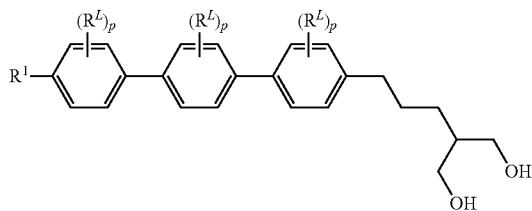
I-19
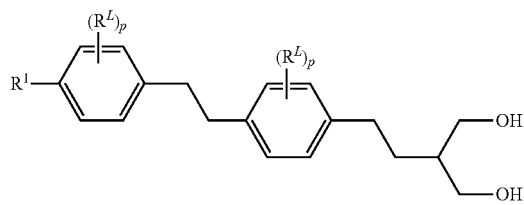
I-20
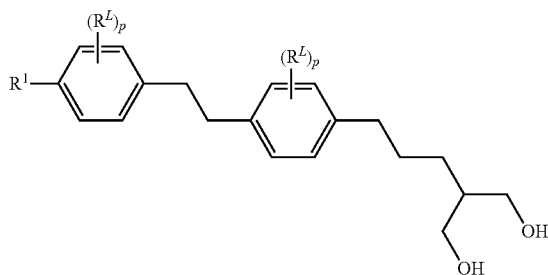
I-21
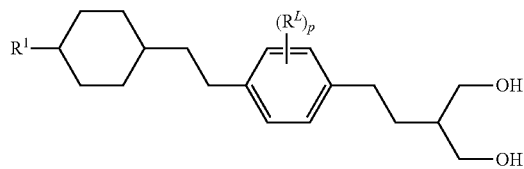
I-22
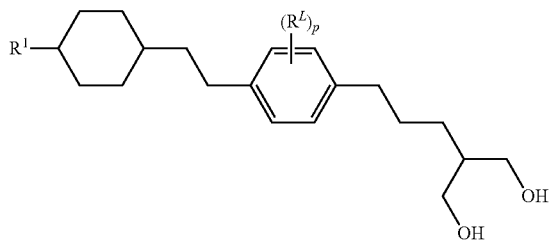
I-23
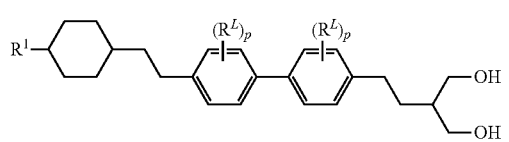
I-24
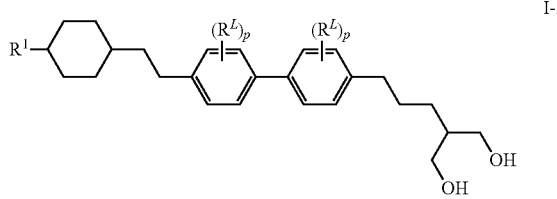
I-25
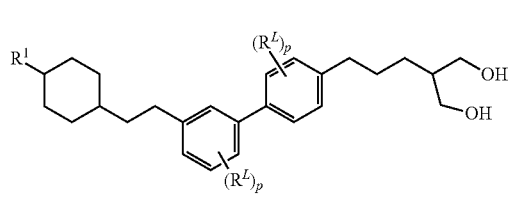
I-26
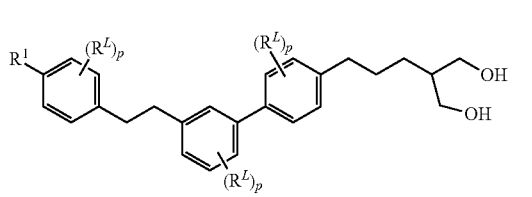
I-27
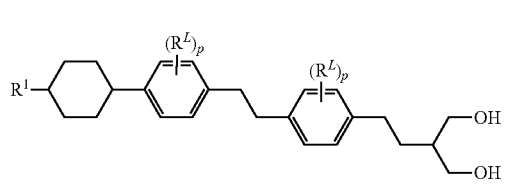
I-28
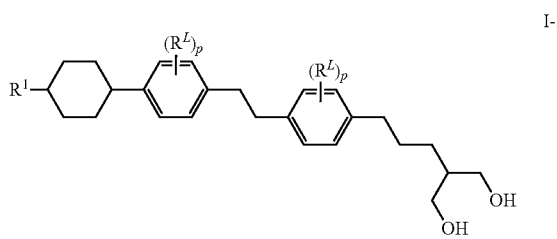
I-29
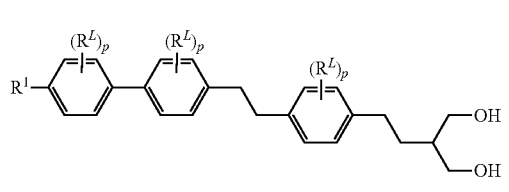
I-30
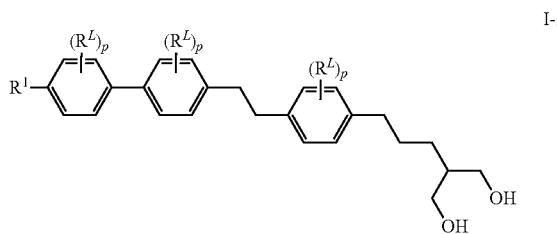

-continued
I-31
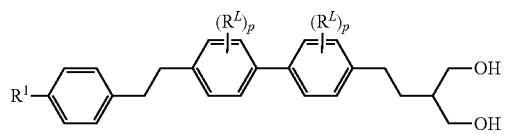
I-32
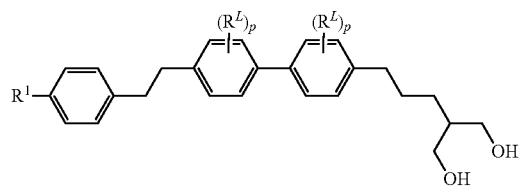
I-33
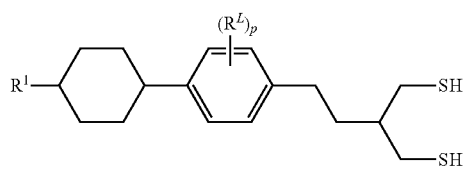
I-34
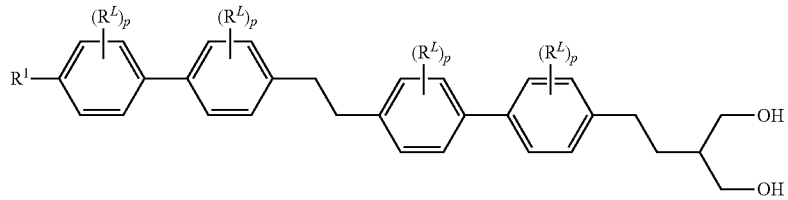
I-35
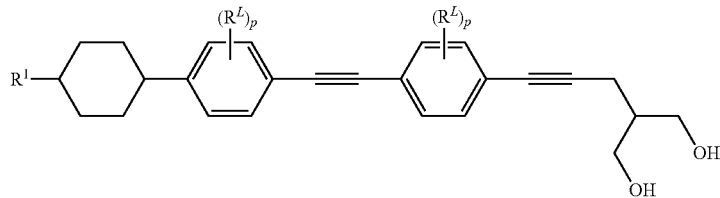
wherein $R^1$ has the meanings denoted above and below, and $R^L$ is independently defined as above and below for formula I, preferably denotes, independently, F, Cl, $CH_3$ or $CH_2CH_3$, and p independently denotes 0, 1, 3, or 4, preferably 0, 1 or 2, more preferably 0 or 1.
Preferred embodiments of the formulae I-1 to I-35 are shown in the following structure examples:
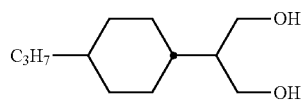
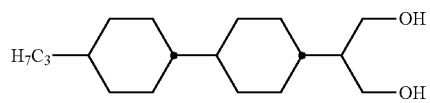
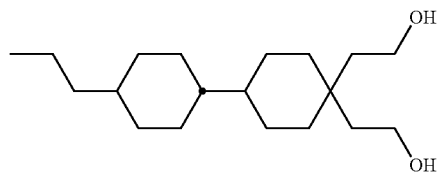
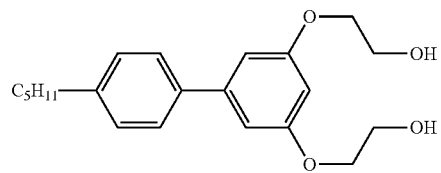
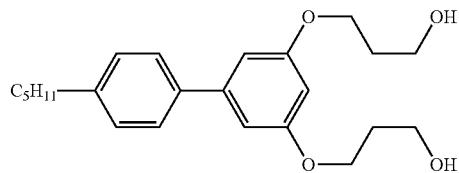
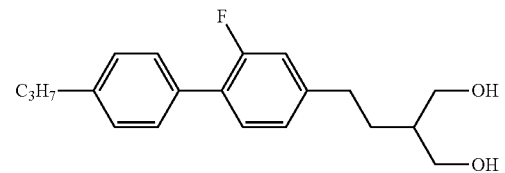
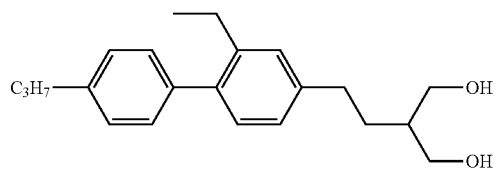
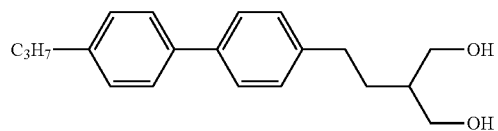

-continued
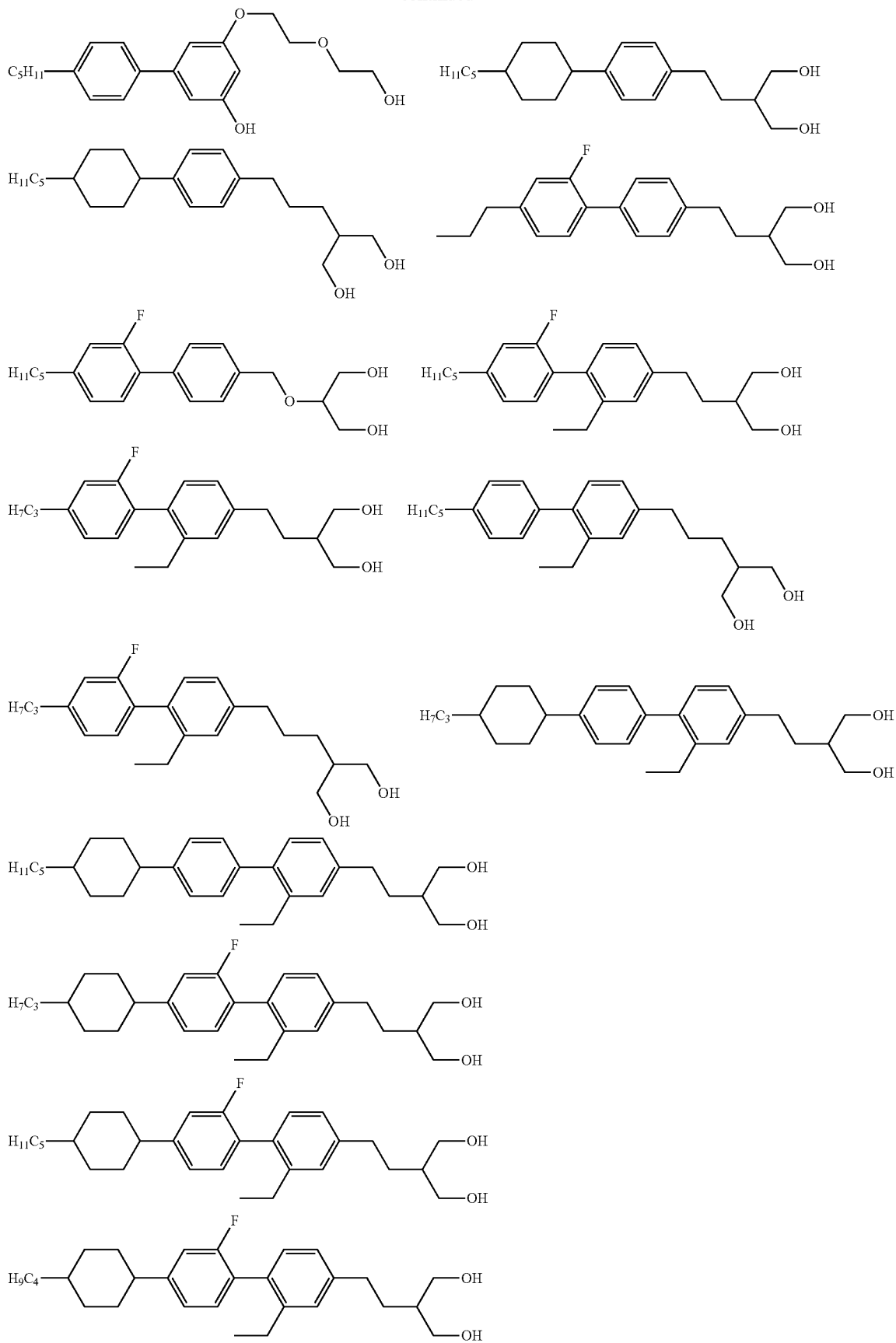

-continued
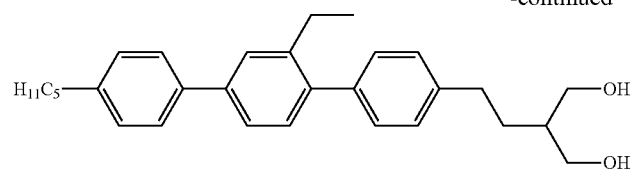
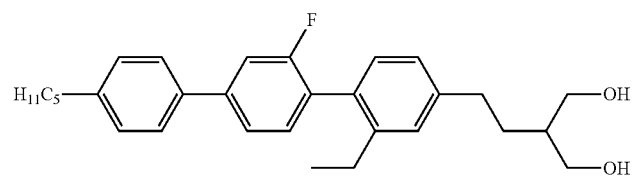
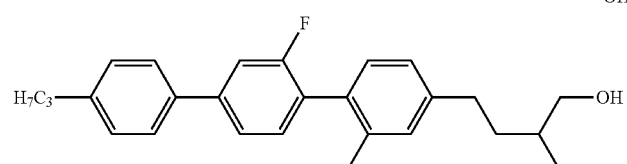
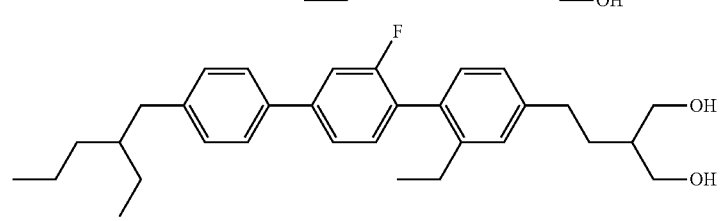
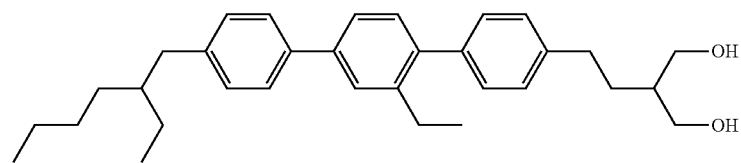
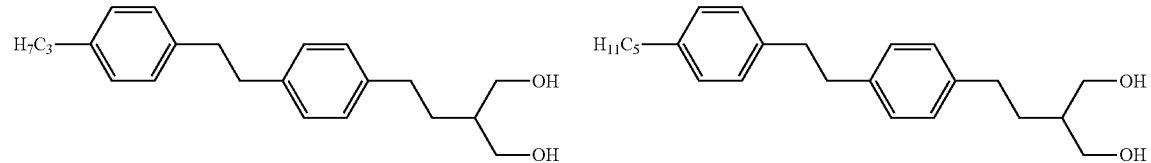
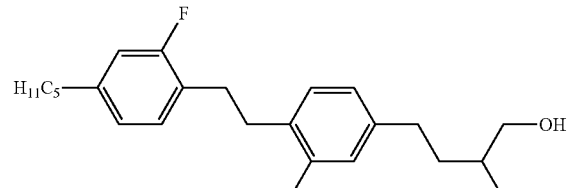
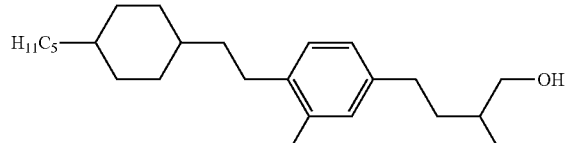
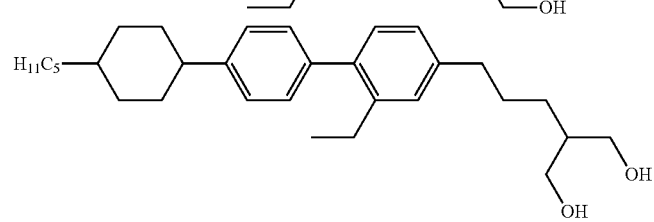
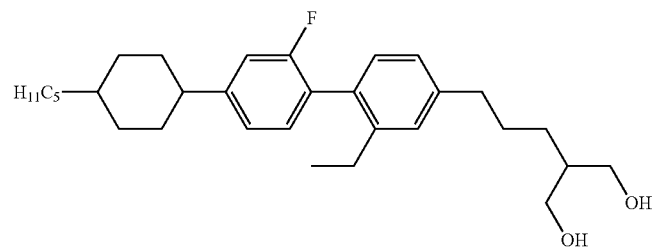

-continued
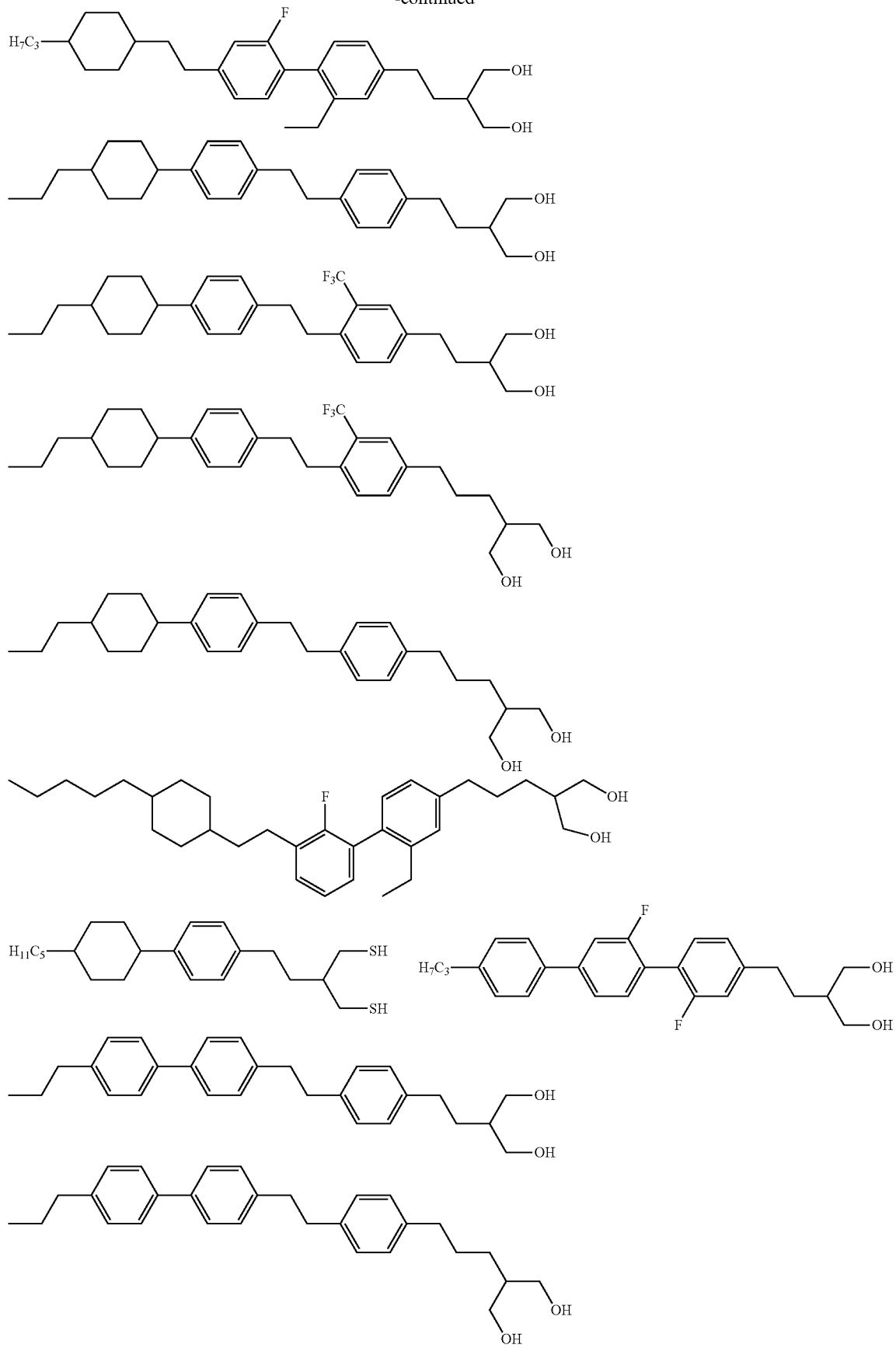

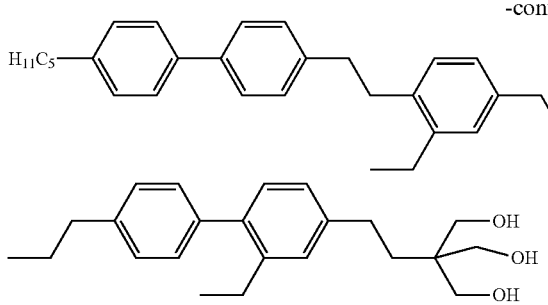
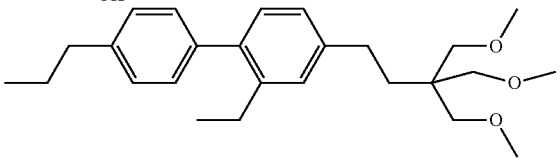

In a further preferred embodiment of the invention, use is made of self-aligning additives of the formula I which, besides the polar anchor, contain one or more polymerizable groups as further functionalisation (compare group $P^a$ or $P^b$ below). Preferred polymerizable groups are groups such as acrylate, methacrylate, fluoroacrylate, oxetane, vinyloxy or epoxide groups, particularly preferably acrylate and methacrylate. The inclusion of compounds of the formula I in the polymerization permanently immobilises the compounds, causing them to retain their function.

An advantage of the LC displays according to the invention is that the displays achieve the desired homeotropic alignment without the conventional polyimide alignment layer. Compared with previously known alignment additives the desired vertical alignment is already achieved at lower concentrations of the additive. The alignment additives according to the invention already show complete alignment of the cell at concentrations as low as 0.1 to 0.5% by weight. This alignment is generally also retained at elevated temperatures, which makes the additives compatible to the display production process e.g. resistance to heat-cure of the sealant. Heat load, even above the clearing point of the LC medium, is tolerated.

In case of applying the polymer stabilisation (e.g. PS-VA), the homeotropic alignment is additionally stabilised; improved temperature stability of the electro-optical switching is thus achieved. The polymer-stabilised displays according to the invention are distinguished by improved response times and a better contrast ratio (pretilt angle and temperature dependence of the contrast). The polymerized component, which is optionally present, can at the same time serve as a passivation layer, which increases the reliability of the display.

The compounds of the formula I do not destabilise the nematic phase of the LC medium thanks to their structure, but instead contribute to the stability. In addition, the relatively small amount of compounds of the formula I has virtually no effect on the properties of the LC media. It is therefore possible to use a broad range of liquid-crystal components in the LC display.

The LC displays according to the invention therefore preferably have no alignment layer for homeotropic alignment on the surfaces of the LC cell, i.e. they are polyimide-free. In the case where the LC displays nevertheless have alignment layers on one or both sides, these preferably consist of polyimide. The alignment layers are then preferably not rubbed, because no rubbing is needed. The rubbing of the alignment layer, a particularly time-consuming step in production, which was hitherto necessary is thus superfluous. The non-rubbed polyimide layer can serve as a passivation layer.

In a particular embodiment, the LC displays according to the invention use an LC medium having negative dielectric anisotropy ($\Delta\epsilon \leq -1.5$). In general, the display is a VA display having electrodes arranged on opposite sides (i.e. the substrates) of the LC cell, preferably having electrodes which are arranged in such a way that they are able to generate an electric field aligned predominantly perpendicular to the substrate surface. Typical substrates used are those which are used from the VAN mode and PSA-VA (structuring of the electrodes is therefore possible).

In a particular embodiment, the LC displays according to the invention use an LC medium having positive dielectric anisotropy ($\Delta\epsilon \geq 1.5$). In general, such display is a VA-IPS display having electrodes arranged on one side (i.e. one substrate) of the LC cell, preferably having electrodes which are arranged in such a way that they are able to generate an electric field aligned predominantly planar to the substrate surface, for example interdigital electrodes (in-plane addressing electrode configuration having a comb-shaped structure).

The LC displays are provided in a conventional manner with polariser(s), which make(s) the LC medium switching operation visible.

The compounds of formula I can be prepared by methods reported in the following, or in analogy to similar compounds taken from literature.

Numerous compounds with a liquid crystal backbone of formula $R^1\text{-}A^1\text{-}(Z^2\text{-}A^2)_{m1}\text{-}$ (part structure of formula I) are already well known to the expert. The introduction of an anchor group $R^2$ into the terminal end can be accomplished by known chemistry. This is illustrated by the following reaction schemes 1, 2 and 3.

Typical additives of formula I are diols of formula 4, derivable from malonic acid,

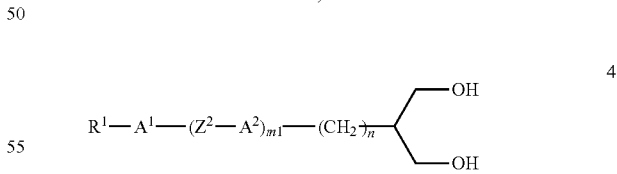

where $R^1$, $A^1$, $A^2$, n and m1 are as defined as in formula I above and below. Compounds of formula 4 with n=0 are known intermediates in liquid crystal chemistry (cf. Examples 1 and 2 below, or WO 2006/015683 A1). Compounds of formula 4 with n>0 and m1=1 are published in the document DD 269856 A1. Compounds of formula 4 with n>0 and m1>1 are new and can be synthesised by alkylation of malonic acid in the presence of a base (NaOEt, NaH, etc.) followed by reduction with, for example, lithium aluminium hydride (Scheme 1).

Scheme 1. R' = C$_{1-7}$ alkyl, X = a leaving group; R, A and m are analogous to R$^1$, A$^1$/A$^2$ and m1 in formula I.

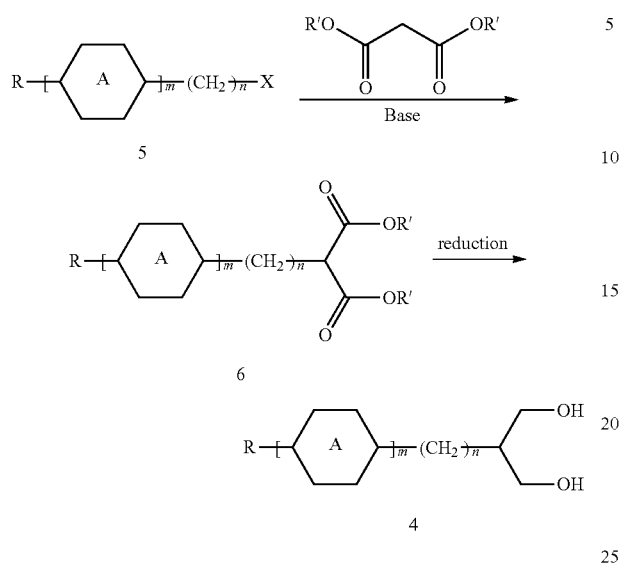

Compounds with an anchor group of formula (A3)

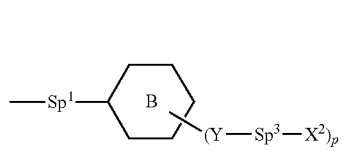

can be prepared from alcohols or phenols of formula (7) by alkylation with optionally protected hydroxy alkyl halides (or other leaving groups instead of halides), or in case of phenols (10) alternatively by Mitsunobu reaction with monoprotected diols (Scheme 2). Common commercially available reagents are 2-chloro- or 2-bromo-ethanol, or 3-benzyloxy-1-propanol.

Scheme 2. n = 1, 2, 3...; PG = protecting group. a) Base; b) DIAD, Ph$_3$P; c) deprotection.

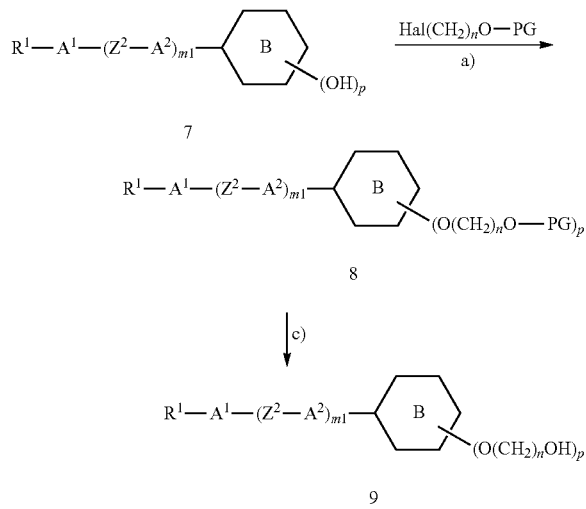

From the above-mentioned alcohols, the according amines are accessible, for example, by Gabriel synthesis as exemplified in Scheme 3.

Scheme 3.

The polymerized component (polymer), which is optionally present in the LC cell, is obtainable by polymerization of a polymerizable component, i.e. one or more kinds of monomers. The polymerizable component consists of one or more polymerizable compounds. Such polymerizable compounds have one to five, preferably two or three, polymerizable groups (preferably those groups P$^{1/2}$ indicated above and below). In general, the one or more monomers are firstly dissolved in the LC medium and are polymerized in the LC cell after homeotropic alignment or a high tilt angle of the LC medium has been established. In order to support the desired alignment, a voltage can be applied to the LC cell. However, in the simplest case, such a voltage is superfluous, and the desired alignment becomes established merely through the nature of the LC medium and the cell geometry.

Suitable monomers (polymerizable component) for the LC medium are those from the prior art which are used for PSA-VA displays, in particular and preferably polymerizable compounds of the formulae M1 to M42 below. The LC media according to the invention for use in PSA displays preferably comprise <5% by weight, particularly preferably <1% by weight and very particularly preferably <0.5% by weight, of polymerizable compounds, in particular polymerizable compounds of the formulae mentioned below. In order to achieve an adequate effect, 0.2% by weight or more is preferably employed. The optimum amount is dependent on the cell thickness.

Suitable and preferred polymerizable compounds (mesogenic monomers), particularly for use in PSA displays, are selected, for example, from the following formulae:

M1
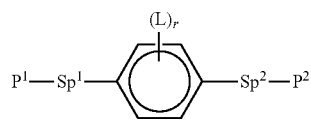

M2
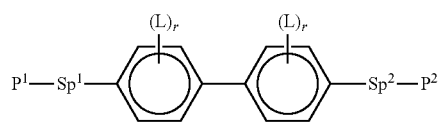

M3
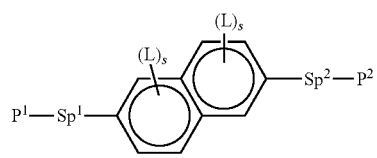

M4
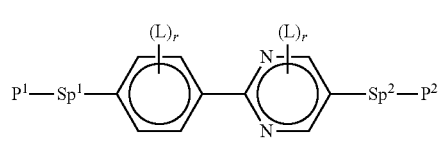

M5
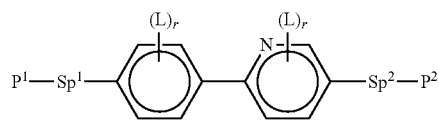

M6
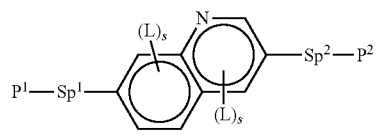

M7
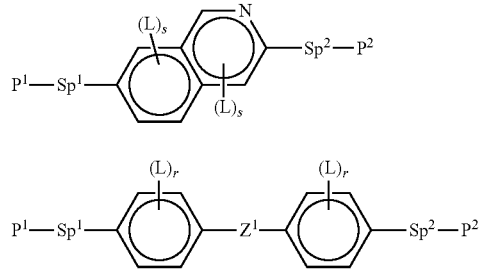

M8
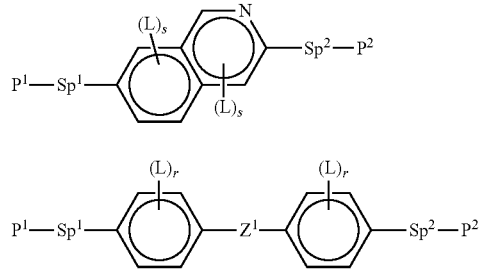

M9
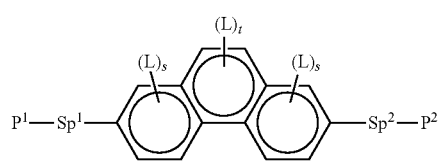

M10
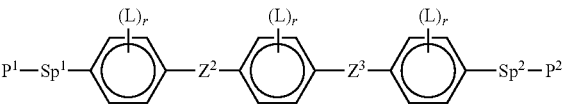

M11
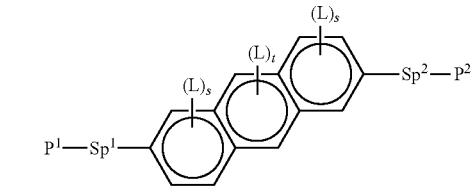

M12
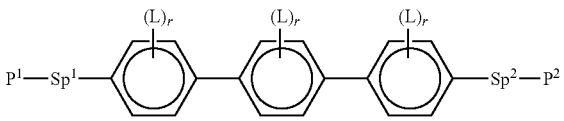

M13
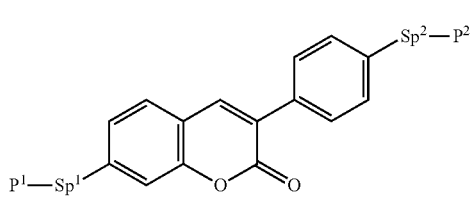

M14
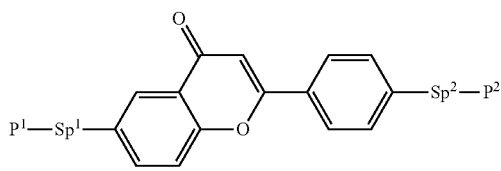

M15
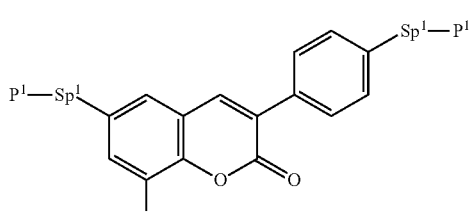

M16
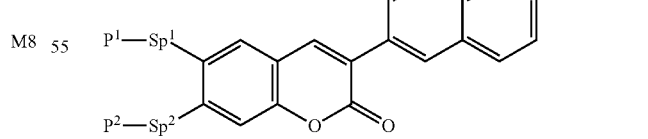

M17
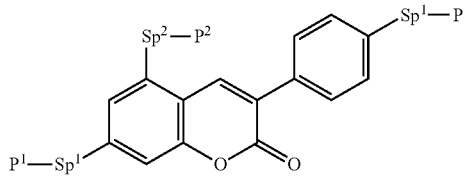

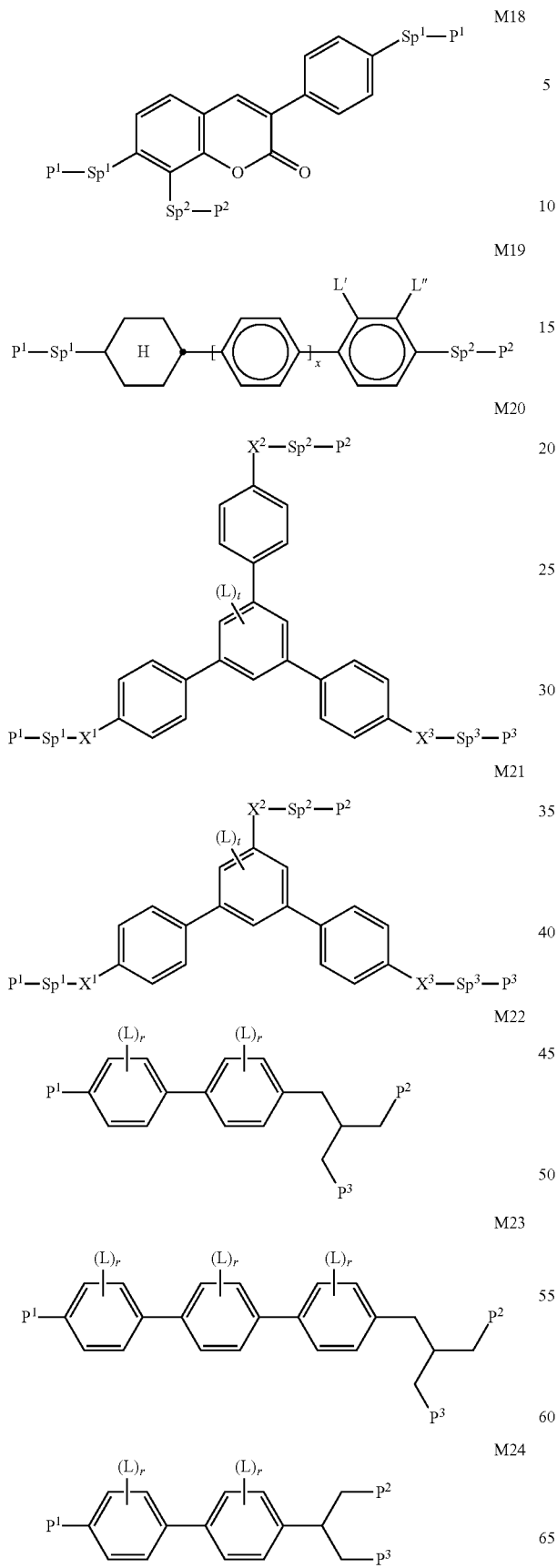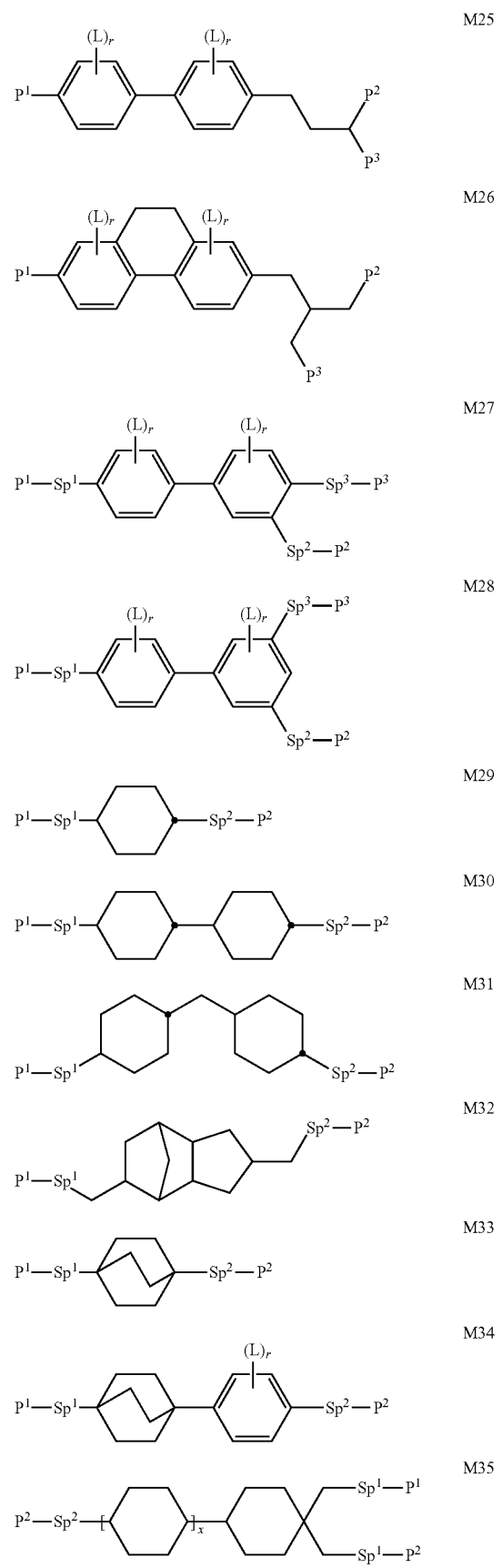

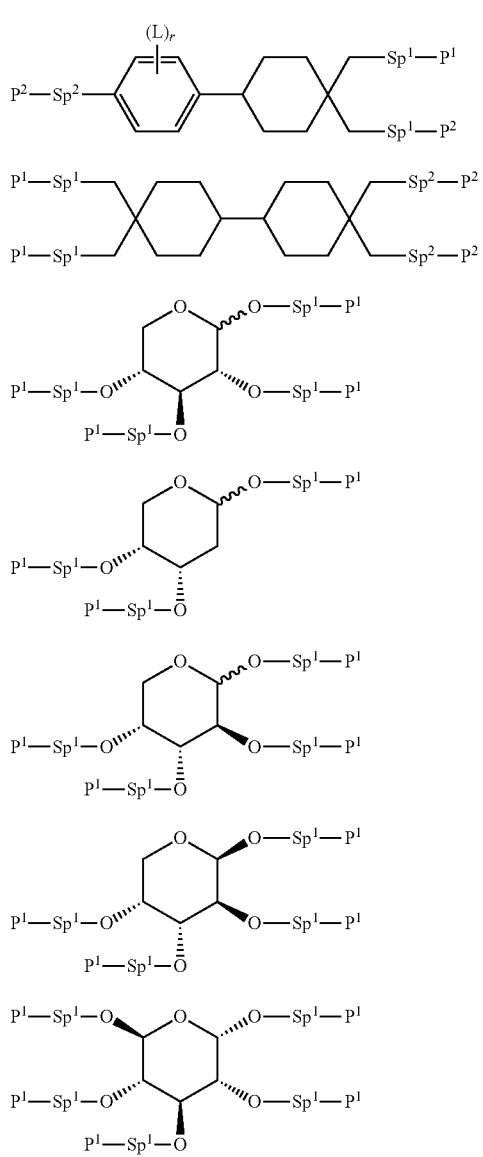

in which the individual radicals have the following meanings:

$P^1$ and $P^2$ each, independently of one another, denote a polymerisable group, preferably an acrylate, methacrylate, fluoroacrylate, oxetane, vinyloxy or epoxide group, $Sp^1$ and $Sp^2$ each, independently of one another, denote a single bond or a divalent spacer group, preferably having one of the meanings indicated above for Sp, and particularly preferably $-(CH_2)_{p1}-$, $-(CH_2)_{p1}-O-$, $-(CH_2)_{p1}-CO-O-$ or $-(CH_2)_{p1}-O-CO-O-$, in which p1 is an integer from 1 to 12, and where the linking to the adjacent ring in the last-mentioned groups takes place via the O atom, where, in addition, one or more of the radicals $P^1$-$Sp^1$- and $P^2$-$Sp^2$- may denote a radical $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^0$, $R^{00}$ each, independently of one another, denote H or alkyl having 1 to 12 C atoms, $R^y$ and $R^z$ each, independently of one another, denote H, F, $CH_3$ or $CF_3$, $Z^1$ denotes $-O-$, $-CO-$, $-C(R^yR^z)-$ or $-CF_2CF_2-$, $Z^2$ and $Z^3$ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN, SCN, $SF_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, and x denotes 0 or 1.

The LC medium or the polymerizable component preferably comprises one or more compounds selected from the group of the formulae M1-M42, particularly preferably from the group of the formulae M2-M26, very particularly preferably from the group of the formulae M2, M3, M9, M14 and M15.

The LC medium or the polymerizable component preferably comprises no compounds of the formula M10 in which $Z^2$ and $Z^3$ denote $-(CO)O-$ or $-O(CO)-$.

For the production of PSA displays, the polymerizable compounds are polymerized or crosslinked (if a polymerizable compound contains two or more polymerizable groups) by in-situ polymerization in the LC medium between the substrates of the LC display, optionally with application of a voltage. The polymerization can be carried out in one step. It is also possible firstly to carry out the polymerization with application of a voltage in a first step in order to produce a pretilt angle, and subsequently, in a second polymerization step, to polymerise or crosslink the compounds which have not fully reacted in the first step without an applied voltage ("end curing").

Suitable and preferred polymerization methods are, for example, thermal or photopolymerization, preferably photopolymerization, in particular UV photopolymerization. One or more initiators as an auxiliary substance can optionally also be added here. Suitable conditions for the polymerization and suitable types and amounts of initiators are known to the person skilled in the art and are described in the literature. Suitable for free-radical polymerization are, for example, the commercially available photoinitiators Irgacure651®, Irgacure184®, Irgacure907®, Irgacure369® or Darocure1173®(Ciba AG). If an initiator is employed, its proportion is preferably 0.001 to 5% by weight, particularly preferably 0.001 to 1% by weight.

The polymerizable compounds according to the invention are also suitable for polymerization without an initiator, which is associated with considerable advantages, such as, for example, lower material costs and, in particular, reduced contamination of the LC medium by possible residual amounts of the initiator or degradation products thereof. The polymerization can thus also be carried out without addition of an initiator. The LC medium thus, in a preferred embodiment, comprises no polymerization initiator.

The polymerizable component or the LC medium may also comprise one or more stabilisers as an auxiliary substance in order to prevent undesired spontaneous polymerization of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of the RMs or the polymerizable component, is preferably 10-10,000 ppm, particularly preferably 50-500 ppm.

Besides the self-aligning additives described above and the optional polymerizable compounds described above, the LC media for use in the LC displays according to the invention comprise an LC mixture ("host mixture") comprising one or more, preferably two or more, low-molecular-weight (i.e. not polymeric) compounds. The latter are stable or unreactive with respect to a polymerization reaction under the conditions used for the polymerization of the polymerizable compounds. In principle, a suitable host mixture is any dielectrically negative or positive LC mixture which is suitable for use in conventional VA and VA-IPS displays.

Suitable LC mixtures are known to the person skilled in the art and are described in the literature. LC media for VA displays having negative dielectric anisotropy are described in EP 1 378 557 A1.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851 and WO 96/28 521.

Preferred embodiments of the liquid-crystalline medium having negative dielectric anisotropy according to the invention are indicated below:

LC medium which additionally comprises one or more compounds selected from the group of the compounds of the formulae A, B and C,

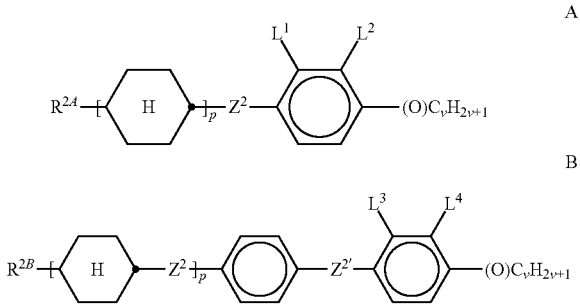

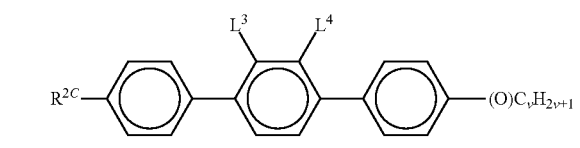

in which
R$^{2A}$, R$^{2B}$ and R$^{2C}$ each, independently of one another, denote H, an alkyl radical having up to 15 C atoms which is unsubstituted, monosubstituted by CN or CF$_3$ or at least monosubstituted by halogen, where, in addition, one or more CH$_2$ groups in these radicals may be replaced by —O—, —S—,

—C≡C—, —CF$_2$O—, —OCF$_2$—, —OC—O— or —O—CO— in such a way that O atoms are not linked directly to one another, L$^{1-4}$ each, independently of one another, denote F, Cl, CF$_3$ or CHF$_2$, Z$^2$ and Z$^{2'}$ each, independently of one another, denote a single bond, —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF—, —CH=CHCH$_2$O—, p denotes 1 or 2,
q denotes 0 or 1, and
v denotes 1 to 6.

In the compounds of the formulae A and B, Z$^2$ can have identical or different meanings. In the compounds of the formula B, Z$^2$ and Z$^{2'}$ can have identical or different meanings.

In the compounds of the formulae A, B and C, R$^{2A}$, R$^{2B}$ and R$^{2C}$ each preferably denote alkyl having 1-6 C atoms, in particular CH$_3$, C$_2$H$_5$, n-C$_3$H$_7$, n-C$_4$H$_9$, n-C$_5$H$_{11}$.

In the compounds of the formulae A and B, L$^1$, L$^2$, L$^3$ and L$^4$ preferably denote L$^1$=L$^2$=F and L$^3$=L$^4$=F, furthermore L$^1$=F and L$^2$=Cl, L$^1$=Cl and L$^2$=F, L$^3$=F and L$^4$=Cl, L$^3$=Cl and L$^4$=F. Z$^2$ and Z$^{2'}$ in the formulae A and B preferably each, independently of one another, denote a single bond, furthermore a —C$_2$H$_4$— bridge.

If Z$^2$=—C$_2$H$_4$— in the formula B, Z$^{2'}$ is preferably a single bond, or if Z$^{2'}$=—C$_2$H$_4$—, Z$^2$ is preferably a single bond. In the compounds of the formulae A and B, (O)C$_v$H$_{2v+1}$ preferably denotes OC$_v$H$_{2v+1}$, furthermore C$_v$H$_{2v+1}$. In the compounds of the formula C, (O)C$_v$H$_{2v+1}$ preferably denotes C$_v$H$_{2v+1}$. In the compounds of the formula C, L$^3$ and L$^4$ preferably each denote F.

The proportion of compounds of the formulae A and/or B in the mixture as a whole is preferably at least 20% by weight.

The values of the birefringence Δn in the liquid-crystal mixture are generally between 0.07 and 0.16, preferably between 0.08 and 0.12. The rotational viscosity γ$_1$ at 20° C. before the polymerization is preferably ≤165 mPa·s, in particular ≤140 mPa·s.

Preferred embodiments of the liquid-crystalline medium having positive dielectric anisotropy according to the invention are indicated below:

LC medium which additionally comprises one or more compounds of the formulae II and/or III:

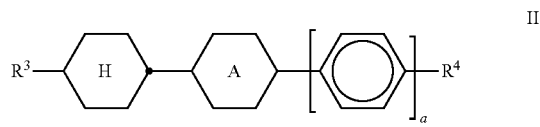

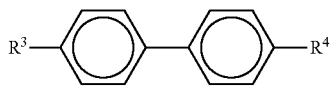
III in which ring A denotes 1,4-phenylene or trans-1,4-cyclohexylene, a is 0 or 1, R³ in each case, independently of one another, denotes alkyl having 1 to 9 C atoms or alkenyl having 2 to 9 C atoms, preferably alkenyl having 2 to 9 C atoms, and R⁴ in each case, independently of one another, denotes an unsubstituted or halogenated alkyl radical having 1 to 12 C atoms, where, in addition, one or two non-adjacent CH₂ groups may be replaced by —O—, —CH=CH—, —CH=CF—, —(CO)—, —O(CO)— or —(CO)O— in such a way that O atoms are not linked directly to one another, and preferably denotes alkyl having 1 to 12 C atoms or alkenyl having 2 to 9 C atoms.

The compounds of the formula II are preferably selected from the group consisting of the following formulae:

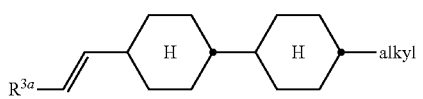
IIa

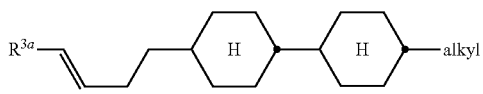
IIb

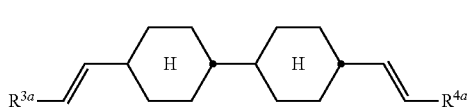
IIc

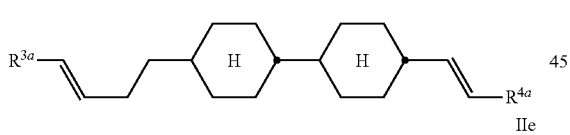
IId

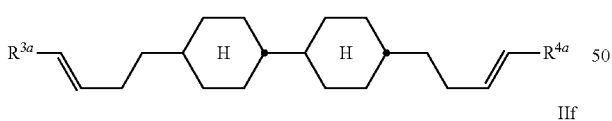
IIe

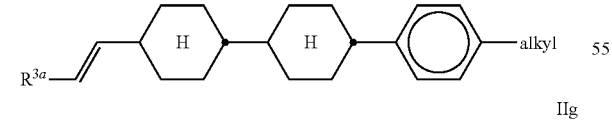
IIf

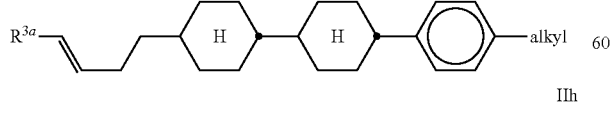
IIg

IIh

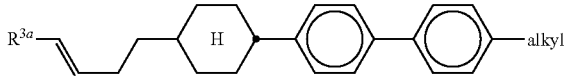
IIi in which $R^{3a}$ and $R^{4a}$ each, independently of one another, denote H, CH₃, C₂H₅ or C₃H₇, and "alkyl" denotes a straight-chain alkyl group having 1 to 8, preferably 1, 2, 3, 4 or 5, C atoms. Particular preference is given to compounds of the formulae IIa and IIf, in particular those in which $R^{3a}$ denotes H or CH₃, preferably H, and compounds of the formula IIc, in particular those in which $R^{3a}$ and $R^{4a}$ denote H, CH₃ or C₂H₅.

LC medium which additionally comprises one or more compounds of the following formula:

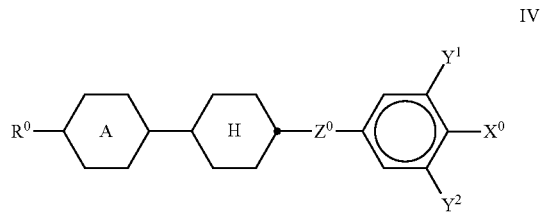
IV

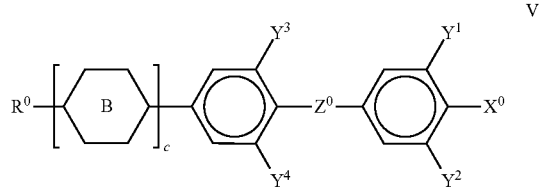
V in which

R⁰ denotes an alkyl or alkoxy radical having 1 to 15 C atoms, where, in addition, one or more CH₂ groups in these radicals may each be replaced, independently of one another, by —C≡C—, —CF₂O—, —CH=CH—,

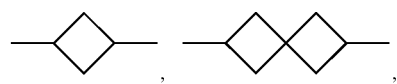

—O—, —(CO)O— or —O(CO)— in such a way that O atoms are not linked directly to one another, and in which, in addition, one or more H atoms may be replaced by halogen, ring A

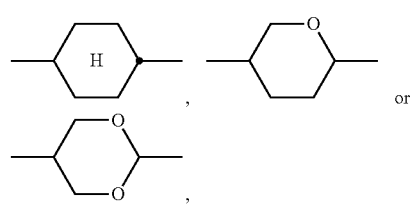

ring B each, independently of one another, denotes 1,4-phenylene, optionally substituted by one or two F or Cl,

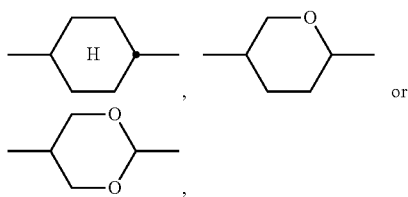

$X^0$ denotes F, Cl, CN, SF$_5$, SCN, NCS, a halogenated alkyl radical, halogenated alkenyl radical, halogenated alkoxy radical or halogenated alkenyloxy radical, each having up to 6 C atoms, $Y^{1-4}$ each, independently of one another, denote H or F, $Z^0$ denotes —CF$_2$O— or a single bond, and c denotes 0, 1 or 2, preferably 1 or 2.

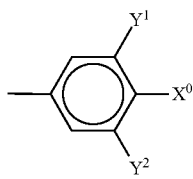

is preferably

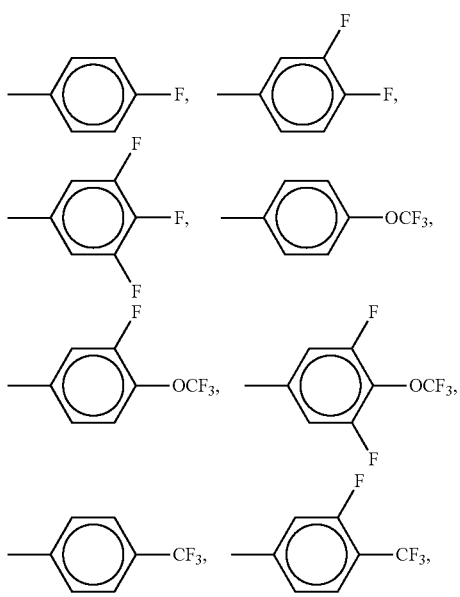

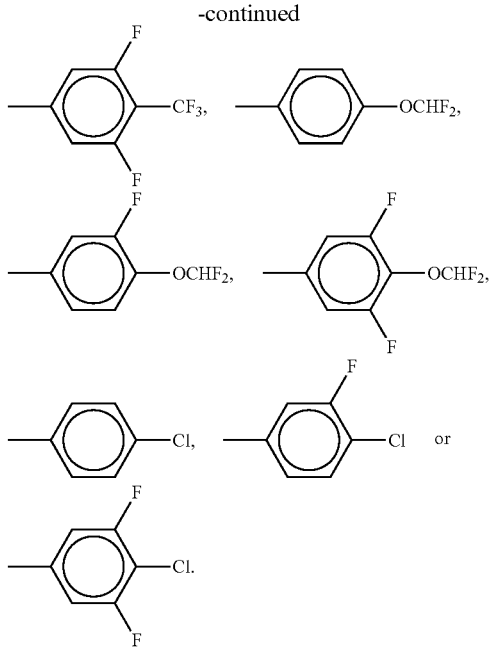

$R^0$ is generally preferably straight-chain alkyl or alkenyl having 2 to 7 C atoms;

$X^0$ is preferably F, furthermore OCF$_3$, Cl or CF$_3$;

the medium preferably comprises one or more compounds selected from the group of the compounds of the formula IV or V;

the proportion of compounds of the formulae II-V in the mixture as a whole is preferably 30 to 99% by weight;

The nematic phase of the dielectrically negative or positive LC medium according to the invention preferably has a nematic phase in a temperature range from 10° C. or less to 60° C. or more, particularly preferably from 0 or less to 70° C. or more.

Throughout the present application the group

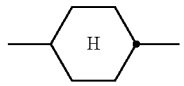

denotes a 1,4-trans-cyclohexane-1,4-diyl.

In the present application and in the examples below, the structures of the liquid-crystal compounds are indicated by means of acronyms, with the transformation into chemical formulae taking place in accordance with Table A below. All radicals C$_n$H$_{2n+1}$ and C$_m$H$_{2m+1}$ are straight-chain alkyl radicals having n and m C atoms respectively; n, m, z and k are integers and preferably denote 1, 2, 3, 4, 5, 6, 7, 8, 9, 10, 11 or 12. The coding in Table A is self-evident.

TABLE A

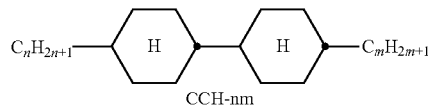
CCH-nm

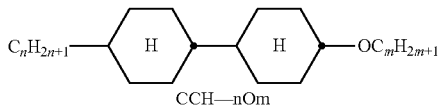
CCH—nOm

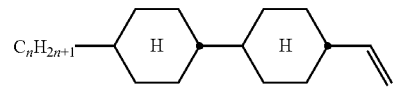

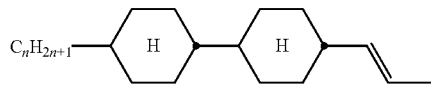

TABLE A-continued
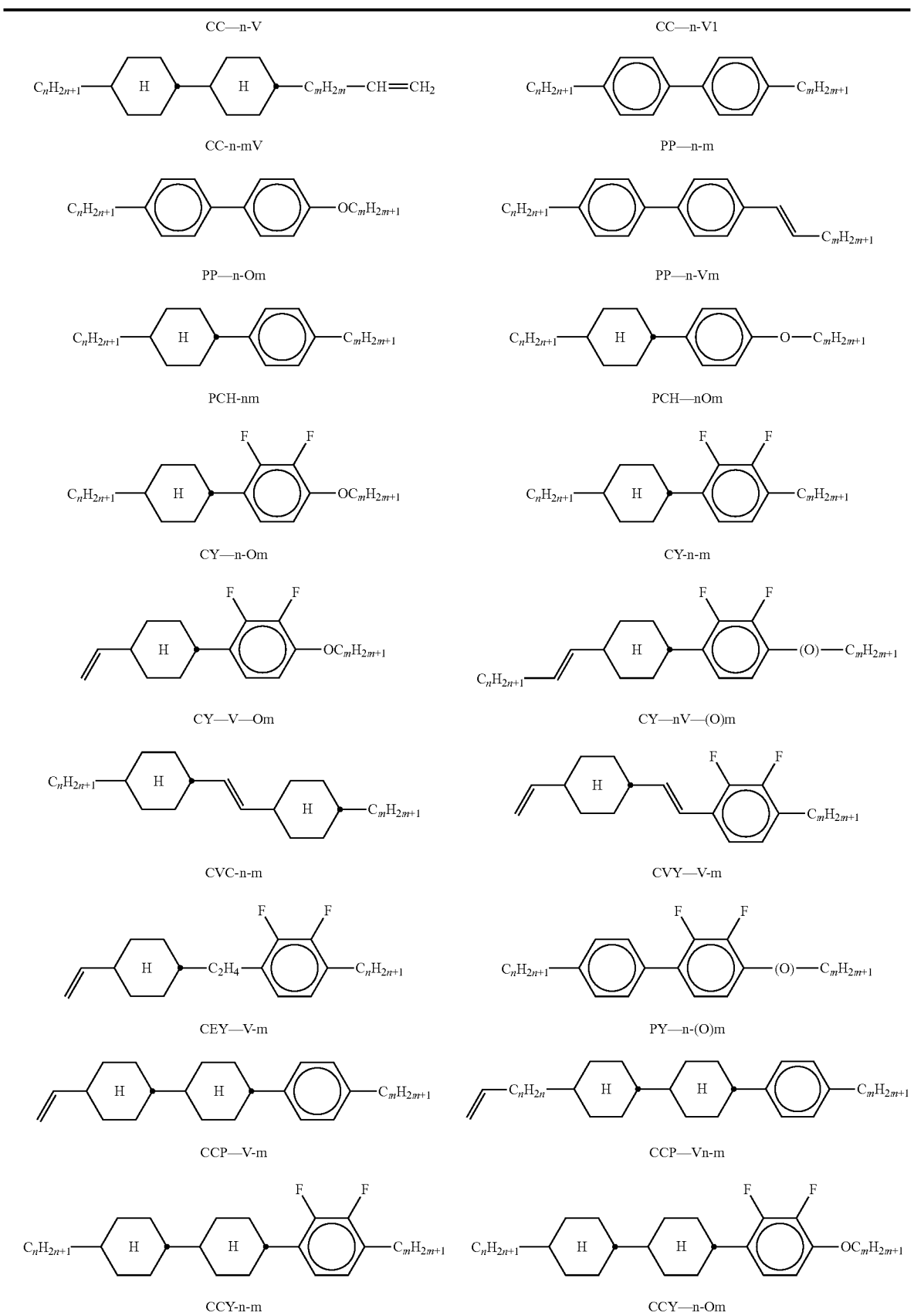

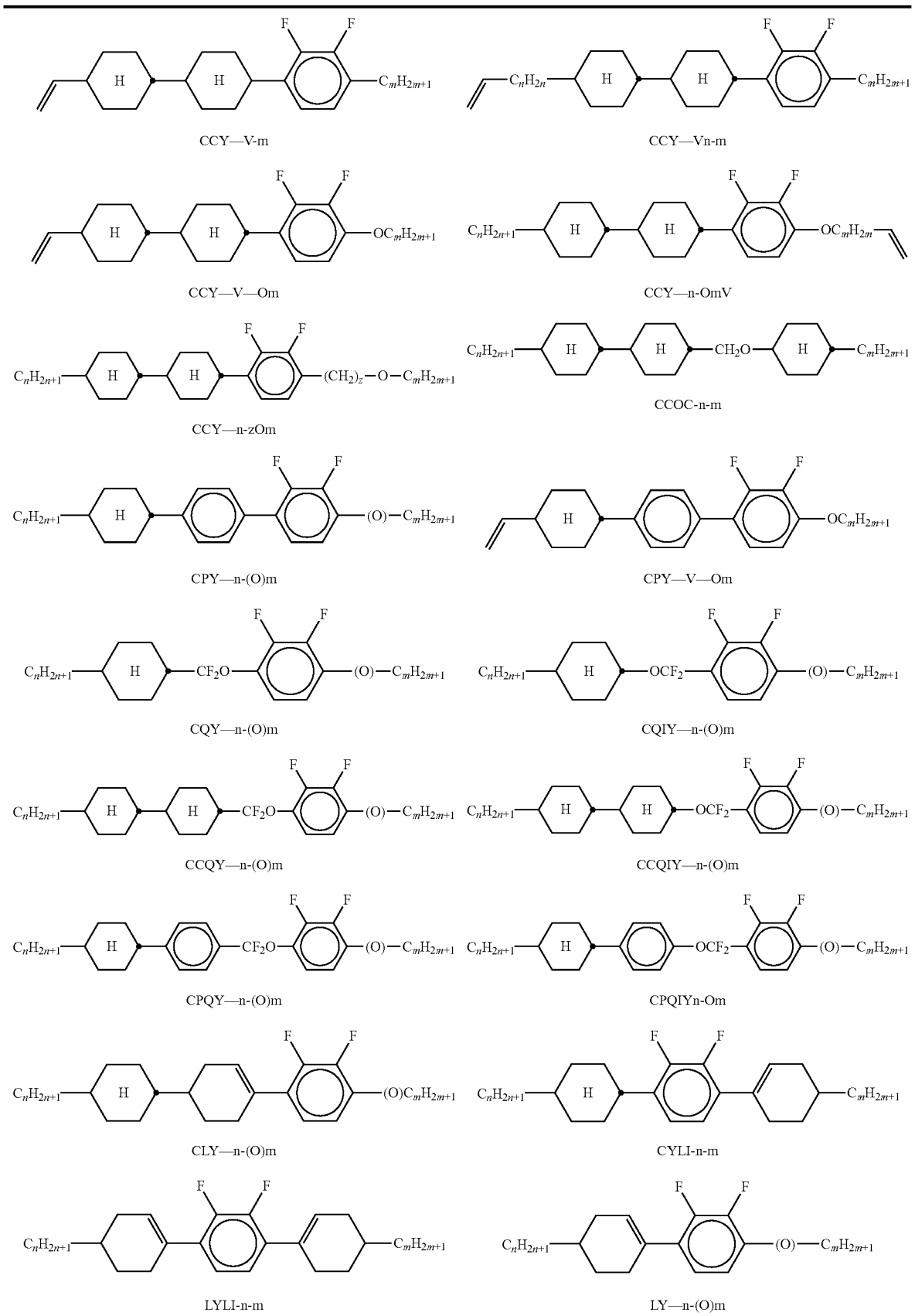

TABLE A-continued
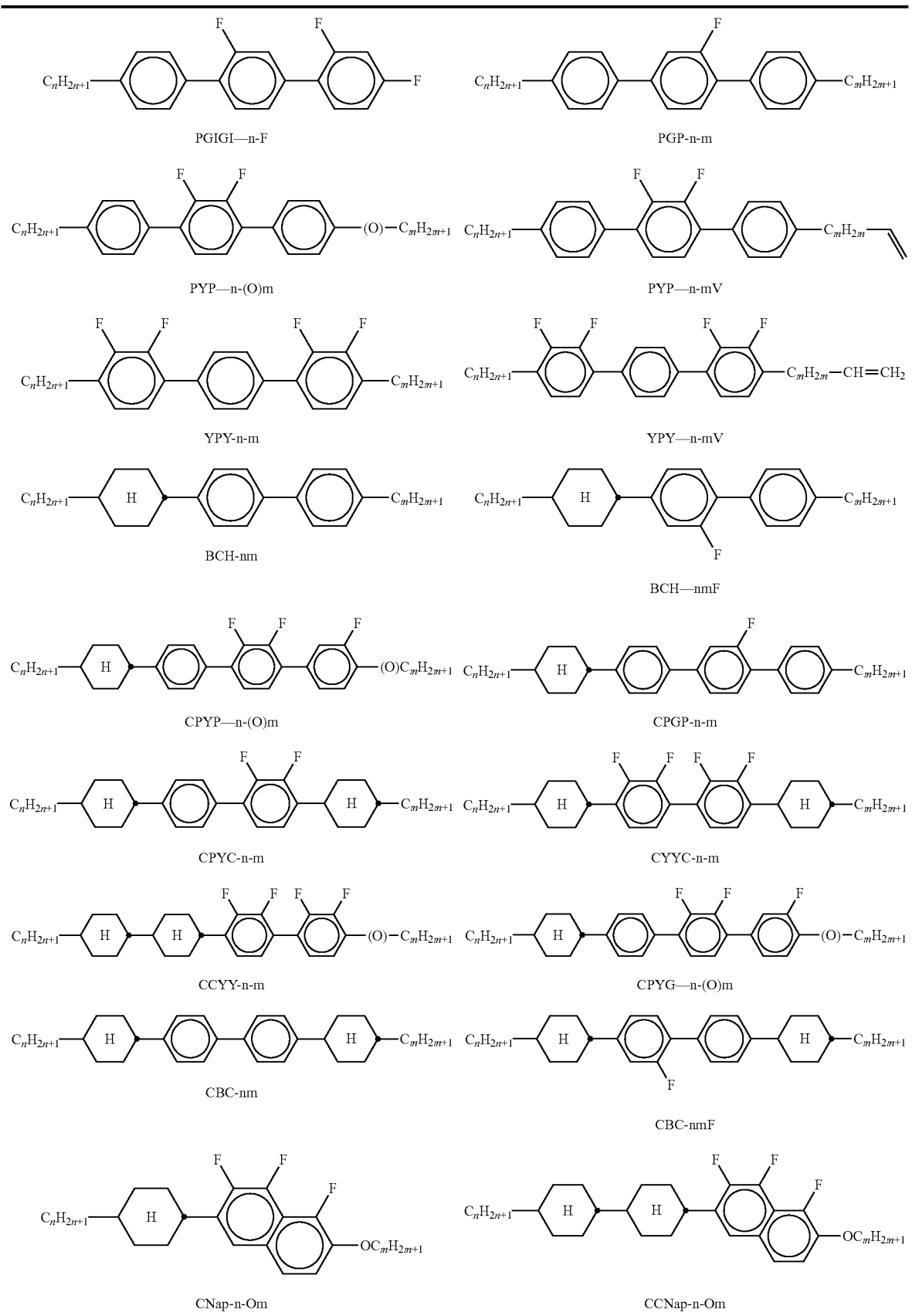

TABLE A-continued
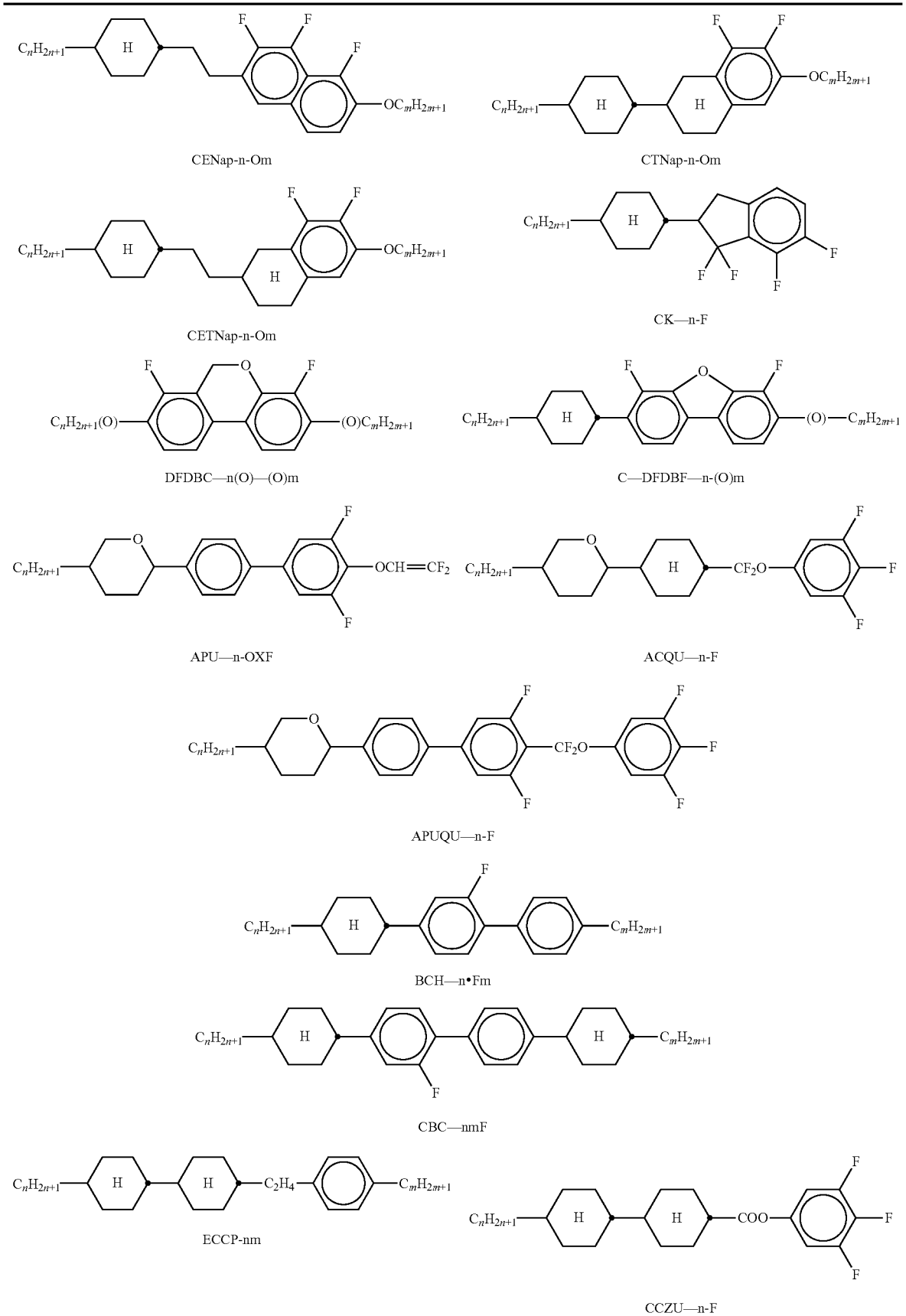

TABLE A-continued
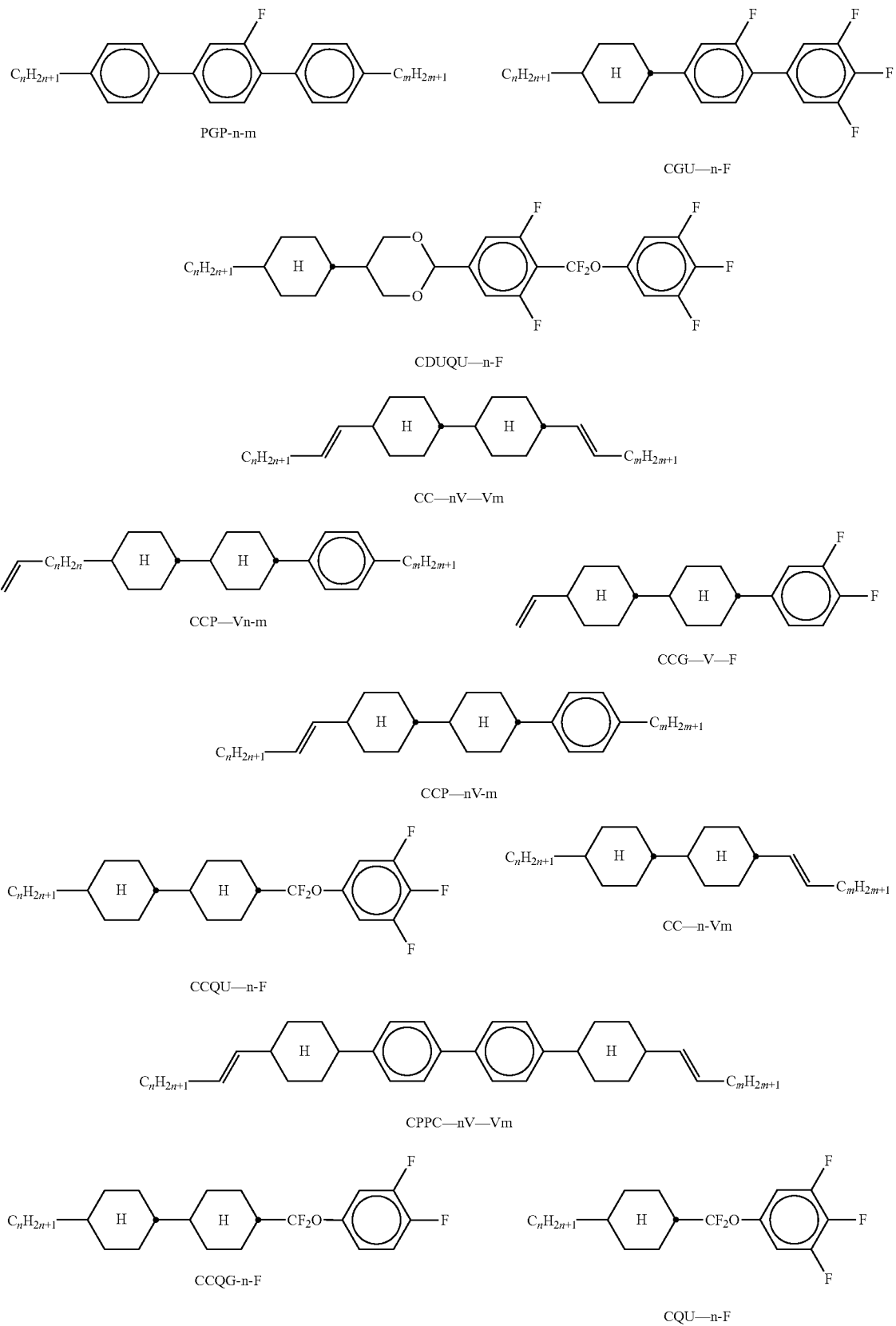

TABLE A-continued
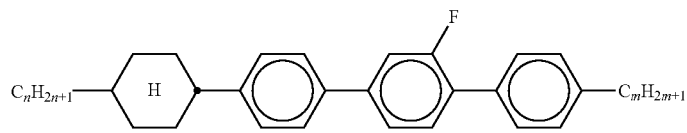
CPGP-n-m
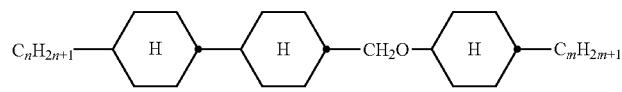
CCOC-n-m
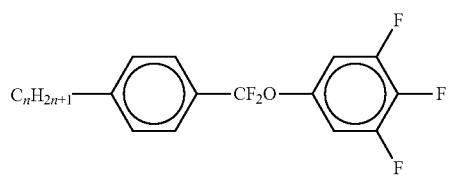
PQU—n-F
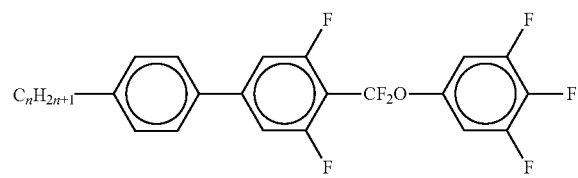
PUQU—n-F
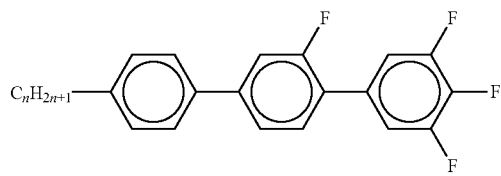
PGU—n-F
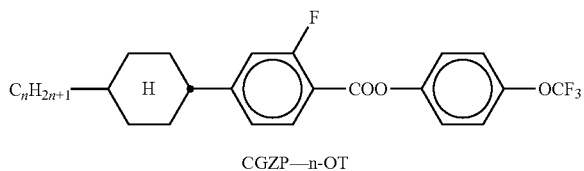
CGZP—n-OT
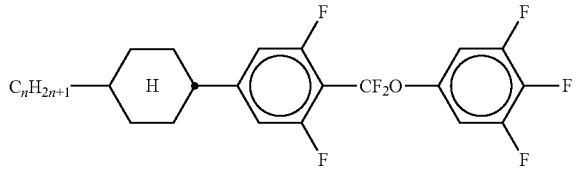
CUQU—n-F
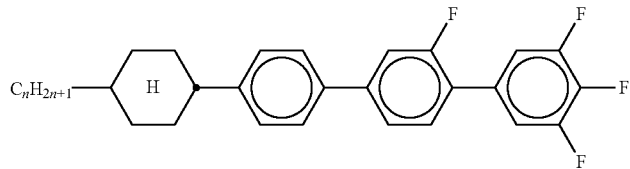
CPGU—n-F
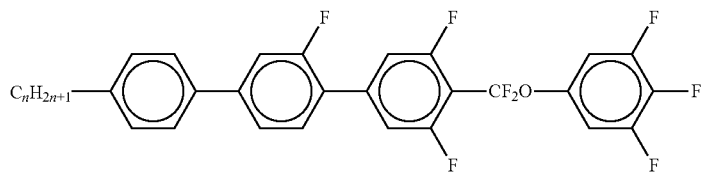
PGUQU—n-F
n, m, z, independently of one another, preferably denote 1, 2, 3, 4, 5 or 6.

In a preferred embodiment of the present invention, the LC media according to the invention comprise one or more compounds selected from the group consisting of compounds from Table A.
TABLE B
Table B indicates possible chiral dopants which can be added to the LC media according to the invention.
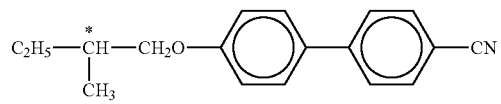
C 15
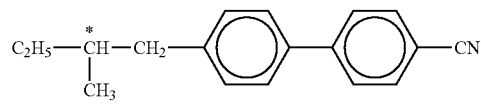
CB 15
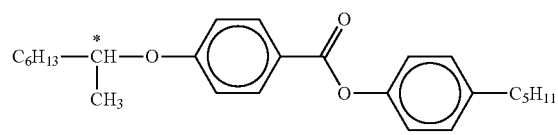
CM 21
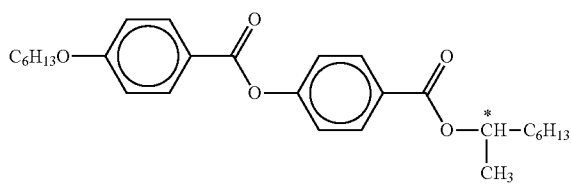
R/S-811
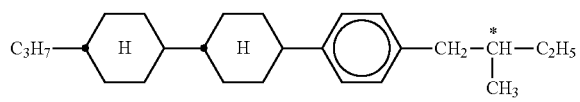
CM 44
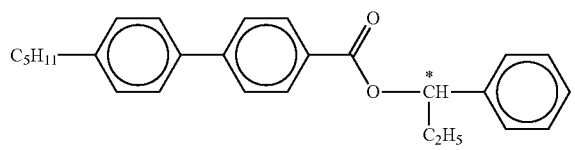
CM 45
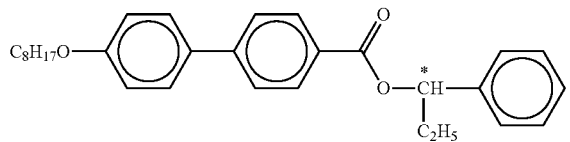
CM 47
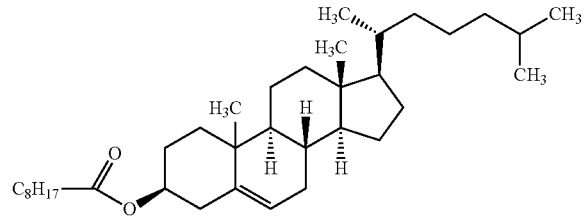
CN
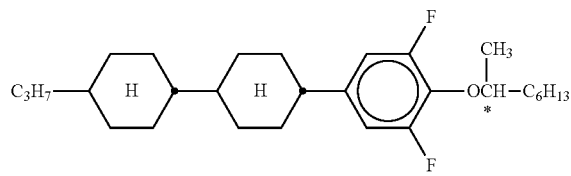
R/S-2011
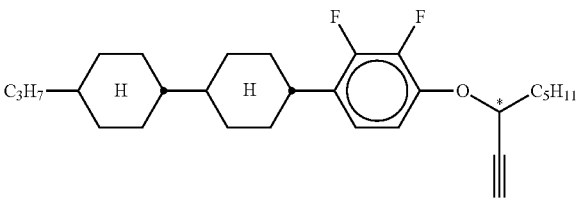
R/S-3011
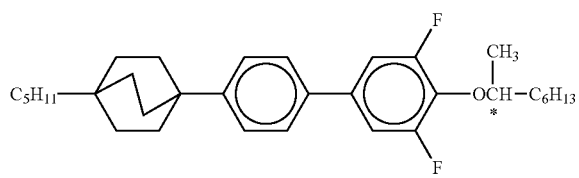
R/S-4011
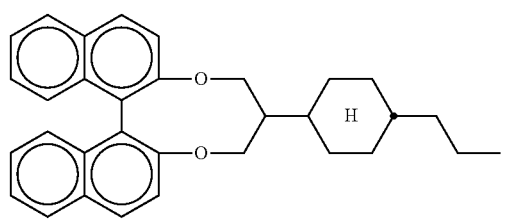
R/S-5011

TABLE B-continued
Table B indicates possible chiral dopants which can be added to the LC media according to the invention.
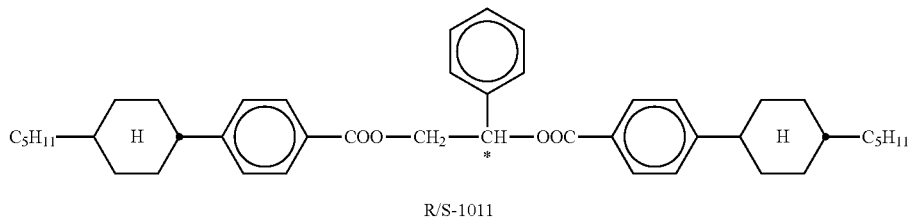
R/S-1011
TABLE C
Table C indicates possible stabilisers as auxiliary substances which can be added to the LC media according to the invention.
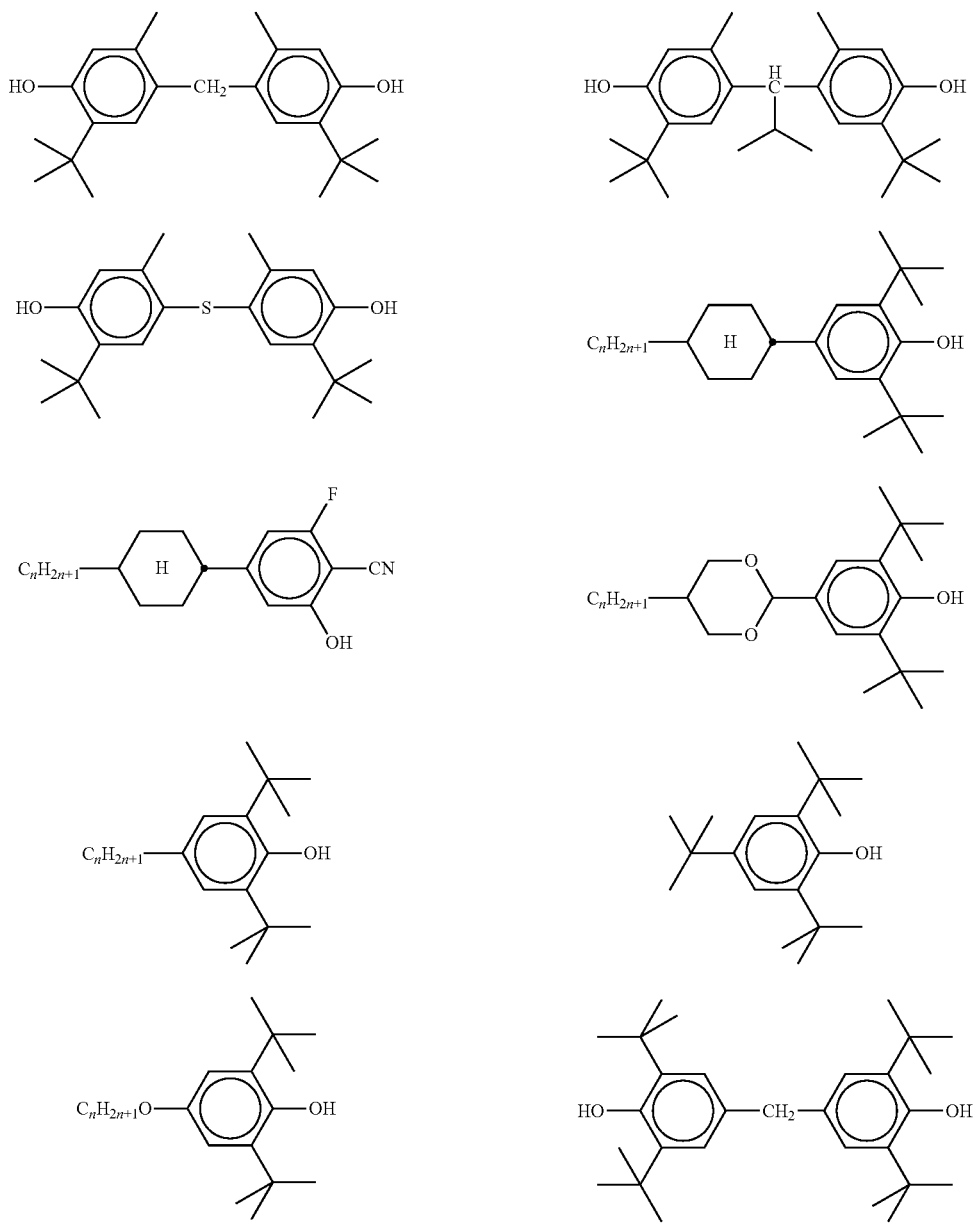

TABLE C-continued
Table C indicates possible stabilisers as auxiliary substances which can be added to the LC media according to the invention.
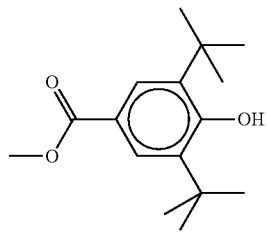 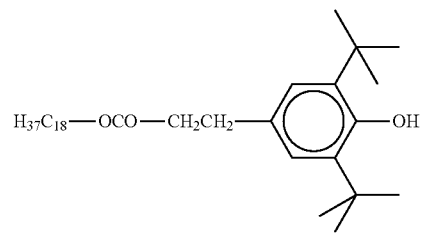
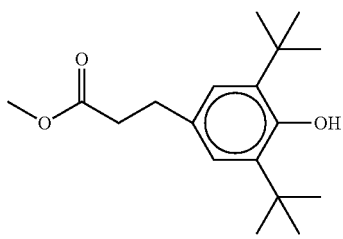 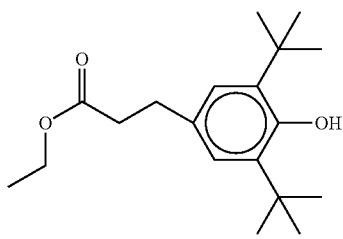
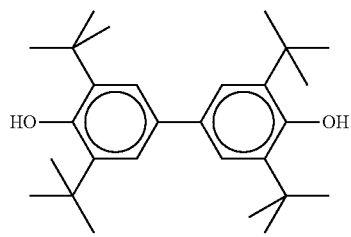 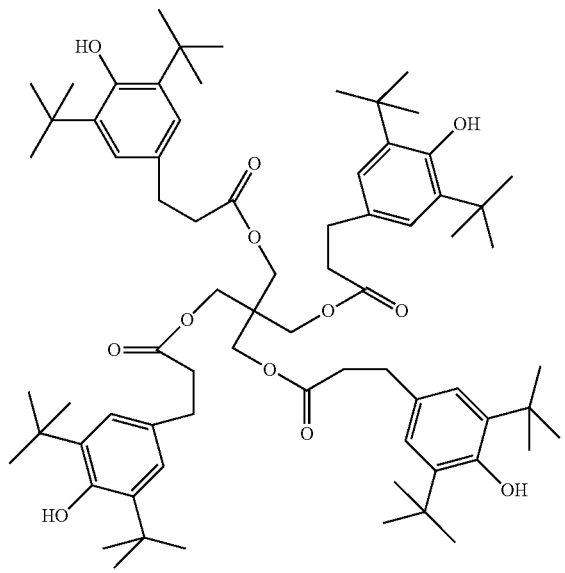 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
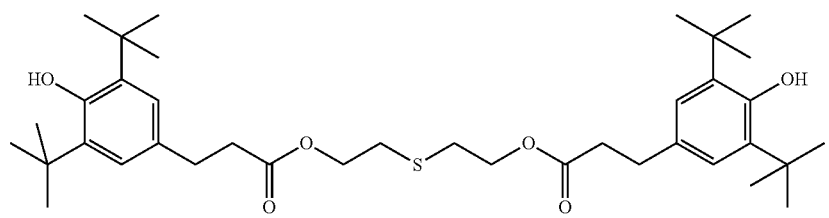 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE C-continued
Table C indicates possible stabilisers as auxiliary substances which can be added to the LC media according to the invention.
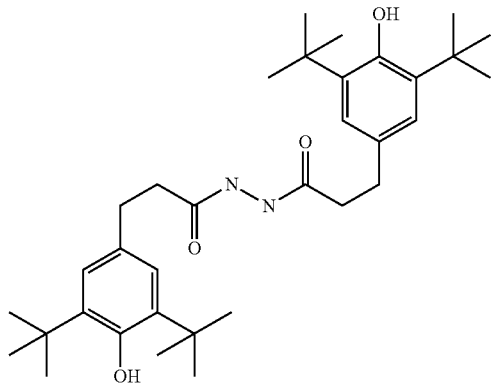 [SMILES: CC(C)(C)c1cc(CCC(=O)NNC(=O)CCc2cc(C(C)(C)C)c(O)c(C(C)(C)C)c2)cc(C(C)(C)C)c1O]
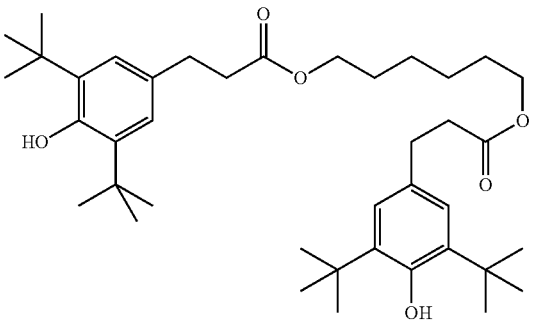 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
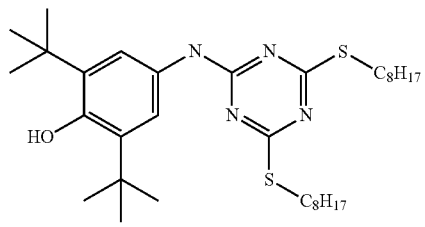
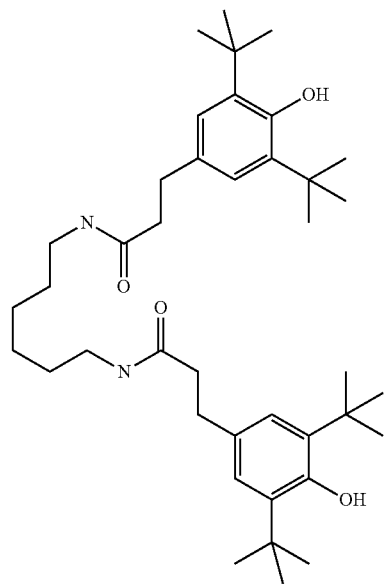 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
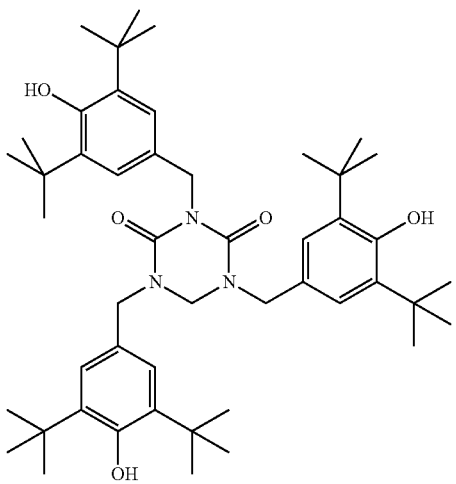 [SMILES: CC(C)(C)c1cc(CN2CN(Cc3cc(C(C)(C)C)c(O)c(C(C)(C)C)c3)C(=O)N(Cc3cc(C(C)(C)C)c(O)c(C(C)(C)C)c3)C2=O)cc(C(C)(C)C)c1O]
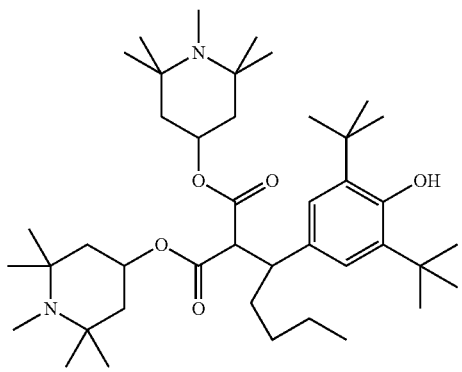 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE C-continued
Table C indicates possible stabilisers as auxiliary substances which can be added to the LC media according to the invention.
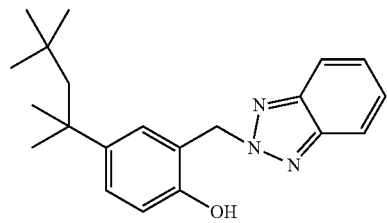 [SMILES: CC(C)(C)CC(C)(C)c1ccc(O)c(Cn2nc3ccccc3n2)c1]
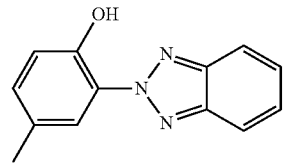 [SMILES: Cc1ccc(O)c(-n2nc3ccccc3n2)c1]
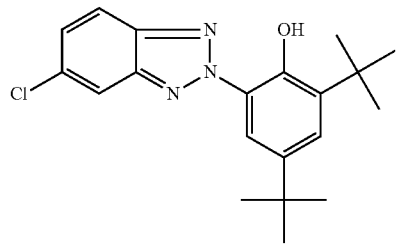 [SMILES: CC(C)(C)c1cc(-n2nc3ccc(Cl)cc3n2)c(O)c(C(C)(C)C)c1]
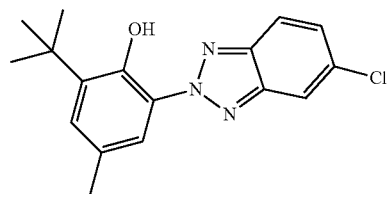 [SMILES: Cc1cc(-n2nc3ccc(Cl)cc3n2)c(O)c(C(C)(C)C)c1]
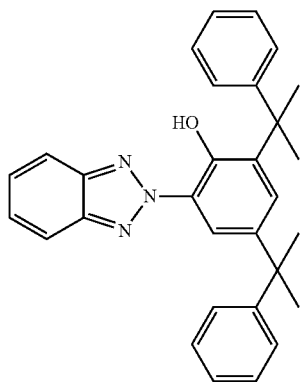 [SMILES: CC(C)(c1ccccc1)c1cc(-n2nc3ccccc3n2)c(O)c(C(C)(C)c2ccccc2)c1]
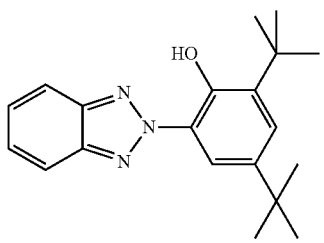 [SMILES: CC(C)(C)c1cc(-n2nc3ccccc3n2)c(O)c(C(C)(C)C)c1]
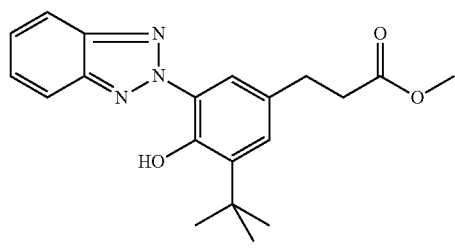 [SMILES: COC(=O)CCc1cc(-n2nc3ccccc3n2)c(O)c(C(C)(C)C)c1]
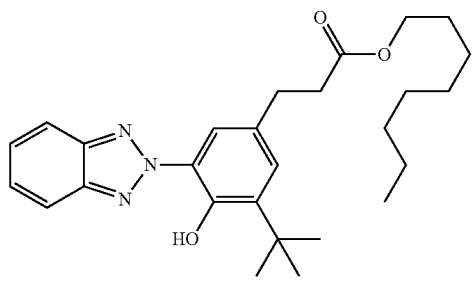 [SMILES: CCCCCCCCOC(=O)CCc1cc(-n2nc3ccccc3n2)c(O)c(C(C)(C)C)c1]

TABLE C-continued

Table C indicates possible stabilisers as auxiliary substances which can be added to the LC media according to the invention.

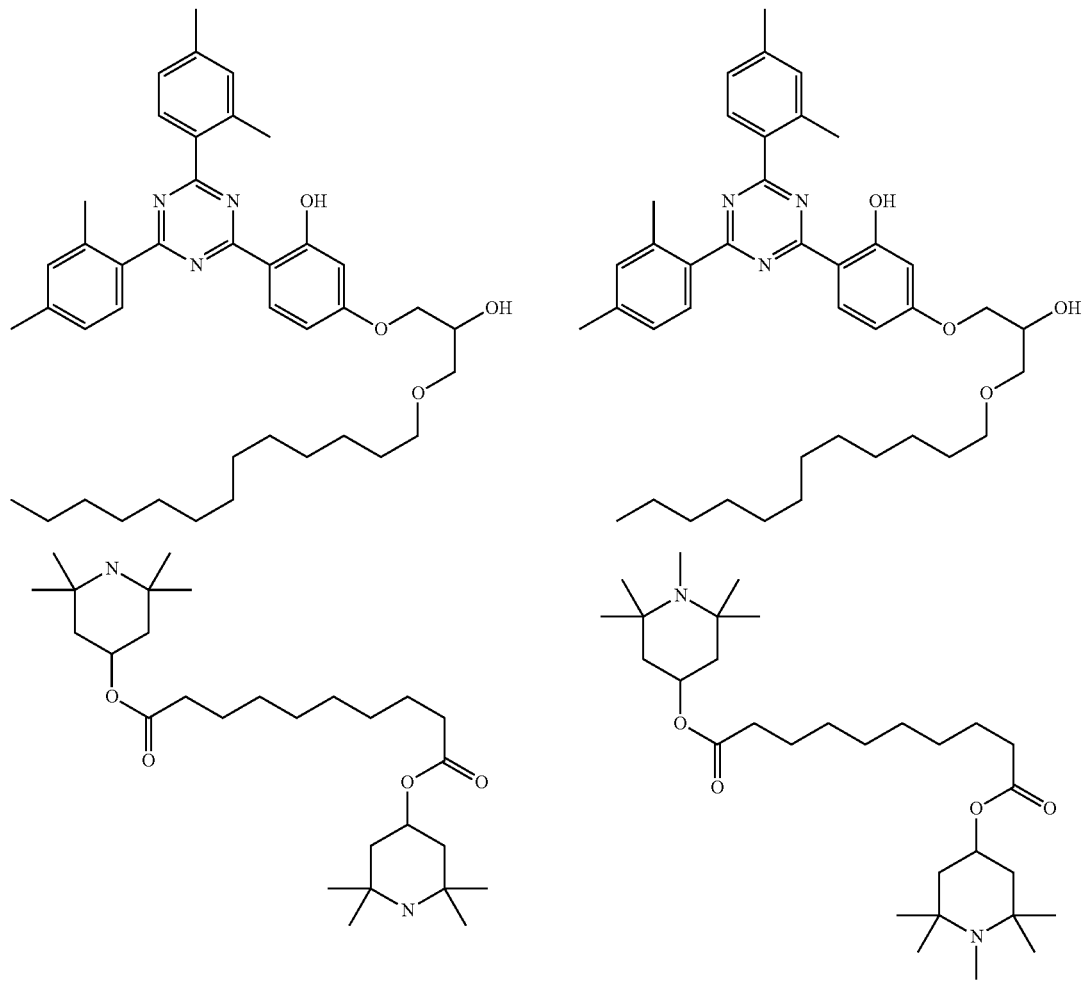

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

In the present application, the term "compounds", also written as "compound(s)", denotes, unless explicitly indicated otherwise, both one and also a plurality of compounds. Conversely, the term "compound" generally also encompasses a plurality of compounds, if this is possible according to the definition and is not indicated otherwise. The same applies to the terms LC media and LC medium. The term "component" in each case encompasses one or more substances, compounds and/or particles.

In addition, the following abbreviations and symbols are used:
$\Delta n$ optical anisotropy at 20° C. and 589 nm,
$\epsilon_{\parallel}$ dielectric permittivity parallel to the director at 20° C. and 1 kHz,
$\Delta\epsilon$ dielectric anisotropy at 20° C. and 1 kHz,
cl.p., T(N,I) clearing point [° C.],
$K_1$ elastic constant, "splay" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and $\Delta n$ is determined at 589 nm and $\Delta\epsilon$ at 1 kHz, unless explicitly indicated otherwise in each case.

Unless stated otherwise, the process of polymerising the polymerizable compounds in the PSA displays as described above and below is carried out at a temperature where the LC medium exhibits a liquid crystal phase, preferably a nematic phase, and most preferably is carried out at room temperature. At temperatures below the clearing point also good vertical alignment is observed due to the use of additives according to the invention.

Unless stated otherwise, methods of preparing test cells and measuring their electro-optical and other properties are carried out by the methods as described hereinafter or in analogy thereto.

The polymerizable compounds are polymerized in the display or test cell by irradiation with UVA light (usually 365 nm) of defined intensity for a pre-specified time, with a voltage optionally being applied simultaneously to the display (usually 10 to 30 V alternating current, 1 kHz). In the examples, unless indicated otherwise, a 100 mW/cm² mercury vapour lamp is used, and the intensity is measured using a standard UV meter (Ushio UNI meter) fitted with a 320 nm band-pass filter.

The following examples explain the present invention without intending to restrict it in any way. However, the physical properties make clear to the person skilled in the art what properties can be achieved and in what ranges they can be modified. In particular, the combination of the various properties which can preferably be achieved is thus well defined for the person skilled in the art.

Further combinations of the embodiments and variants of the invention in accordance with the description also arise from the claims.

EXAMPLES

The compounds employed, if not commercially available, are synthesised by standard laboratory procedures. The LC media originate from Merck KGaA, Germany.

COMPOUNDS—SYNTHESIS EXAMPLES

Example 1.
2-(trans-4-Propyl-cyclohexyl)-propane-1,3-diol (CAS-No. 132310-86-2), is commercially available.

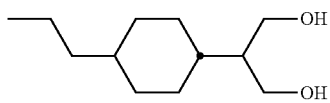

Example 2. 2-(trans-trans-4'-Propyl-bicyclohexyl-4-yl)-propane-1,3-diol (CAS-No. 188660-24-4), is prepared as described in DE 19531135 A1.

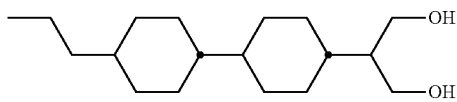

Example 3. 2-[4-(2-Hydroxy-ethyl)-4'-propyl-bicyclohexyl-4-yl]-ethanol (1315986-27-6) is prepared as described in WO 2011/088882 A1.

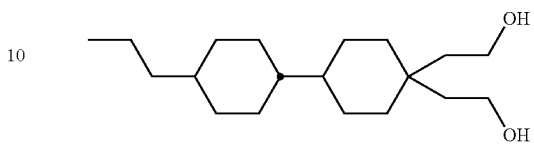

Example 4. 2-[5-(2-Hydroxy-ethoxy)-4'-pentyl-biphenyl-3-yloxy]-ethanol 4.1 3,5-dimethoxy-4'-pentylbiphenyl

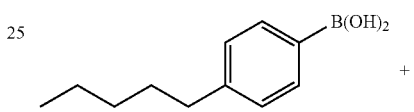

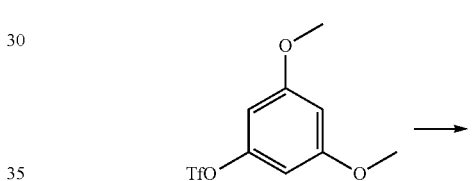

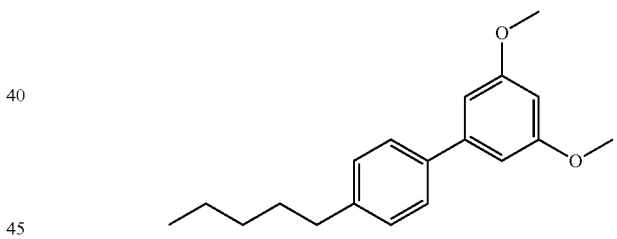

45.4 g (0.326 mol) sodium metaborate tetrahydrate and 8.25 g (12 mmol) bis(triphenylphosphine)palladium(II)chloride) are dissolved in water (150 ml). After addition of hydrazine hydrate (1 ml) a solution of 40.0 g (0.206 mol) 4-pentylbenzene boronic acid and 69.1 g (0.227 mol) 3,5-dimethoxyphenyl triflate in THF (900 ml) is added and the reaction is refluxed overnight and cooled to room temperature. Ethyl acetate is added, the aq. layer extracted with ethyl acetate and the combined organic layers are dried over sodium sulfate. The solvent is evaporated and the residue purified by chromatography on silica (heptane/toluene 1:1, then 1:9). 3,5-dimethoxy-4'-pentylbiphenyl is obtained as colourless crystals.

$^1$H NMR (500 MHz, CDCl$_3$)

δ=0.90 ppm (t, J=6.9 Hz, 3H, CH$_3$), 1.28-1.41 (m, 4H, CH$_2$), 1.59-1.70 (2H, CH$_2$), 2.63 (t, J=7.5 Hz, 2H, Ar—CH$_2$—CH$_2$—), 3.83 (s, 6H, 2-OCH$_3$), 6.44 (t, J=2.3 Hz, 1H, Ar—H), 6.72 (d, J=2.2 Hz, 2H, Ar—H), 7.23 (d, J=8.1 Hz, 2H, Ar—H), 7.48 (d, J=8.1 Hz, 2H, Ar—H).

4.2 4'-Pentylbiphenyl-3,5-diol

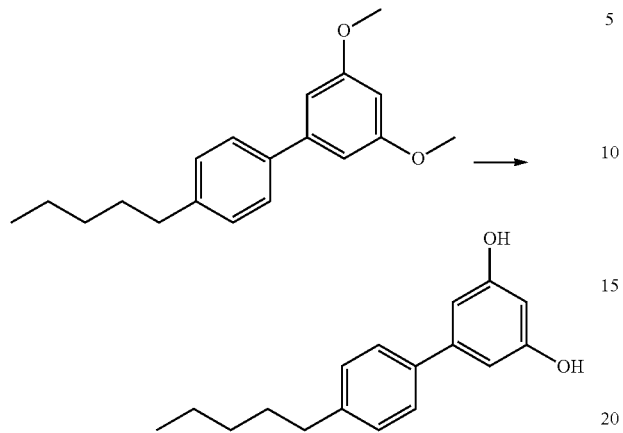

5.00 g (17.4 mmol) 3,5-dimethoxy-4'-pentylbiphenyl are dissolved in dichloromethane (70 ml) and a solution of 4 ml (43 mmol) of boron tribromide in dichloromethane (10 ml) is added dropwise under ice-cooling. The reaction is stirred for 3 h at the same temperature, is poured onto ice and the aq. layer is extracted three times with ethyl acetate. The combined org. layers are evaporated and the residue is recrystallised from toluene/heptane (1:2) to yield 4'-pentyl-biphenyl-3,5-diol as colourless crystals.

$^1$H NMR (400 MHz, DMSO-$d_6$)

δ=0.87 ppm (t, J=6.8 Hz, 3H, $CH_3$), 1.23-1.38 (m, 4H, $CH_2$), 1.53-1.64 (2H, $CH_2$), 2.58 (t, J=7.5 Hz, 2H, Ar—$CH_2$—$CH_2$—), 6.19 (t, J=2.3 Hz, 1H, Ar—H), 6.43 (d, J=2.2 Hz, 2H, Ar—H), 7.23 (d, J=8.2 Hz, 2H, Ar—H), 7.42 (d, J=8.1 Hz, 2H, Ar—H), 9.25 (s, 2H, —OH).

4.3 (5-Ethoxycarbonylmethoxy-4'-pentyl-biphenyl-3-yloxy)-acetic acid ethyl ester

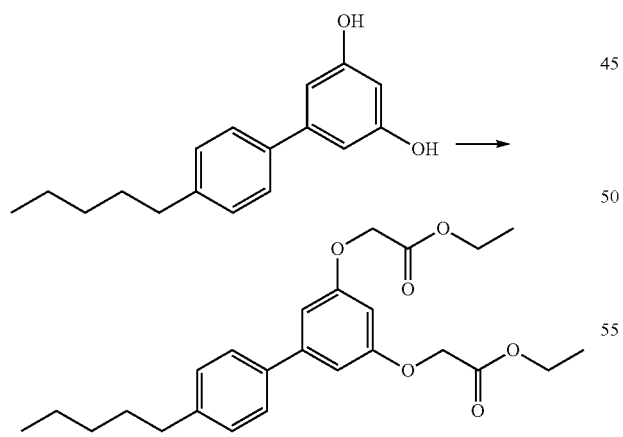

To 28.0 g (109 mmol) 4'-Pentylbiphenyl-3,5-diol and 107 g (328 mmol) caesium carbonate in 300 ml ethyl methyl ketone, 54.7 g (328 mmol) ethyl bromoacetate are added at 50° C. The reaction is heated under reflux for 4 h, cooled and diluted with 200 ml ethyl acetate. After addition of 200 ml water, the mixture is acidified carefully with 2 M hydrochloric acid. The aq. phase is separated and extracted three times with ethyl acetate. The combined org. layers are washed with brine, dried over sodium sulfate and the solvent is evaporated. The residue is filtered through silica with toluene/ethyl acetate (92:8) and the product is used in the next step without further purification.

4.4 2-[5-(2-Hydroxy-ethoxy)-4'-pentyl-biphenyl-3-yloxy]-ethanol

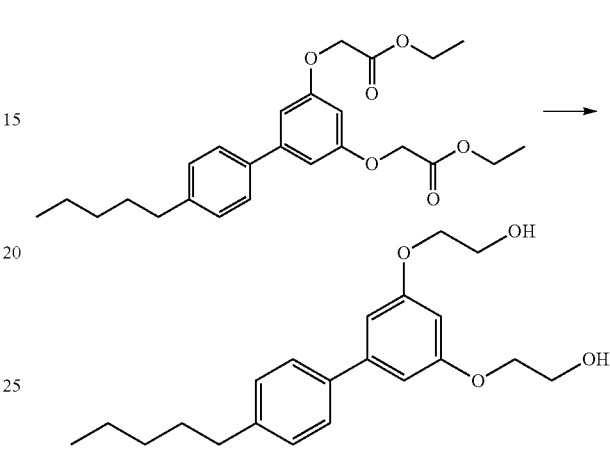

37.4 g (86.8 mmol) (5-Ethoxycarbonylmethoxy-4'-pentyl-biphenyl-3-yloxy)-acetic acid ethyl ester are dissolved in 200 ml THF and under cooling with ice, 86.8 ml (172 mmol) of a 2 M solution of lithium aluminium hydride in THF is added so that the temperature did not exceed 30° C. After 3 h the reaction is poured onto ice-water, acidified with 2 M hydrochloric acid and extracted three times with ethyl acetate. The combined org. layers are dried over solium sulfate and the solvent is evaporated. The residue is filtered through silica with ethyl acetate/toluene (2:1) and recrystallised from toluene ethyl acetate (8:2) to give 2-[5-(2-Hydroxy-ethoxy)-4'-pentyl-biphenyl-3-yloxy]-ethanol as colourless crystals, m.p. 94° C.

Example 5. 3-[5-(3-Hydroxy-propoxy)-4'-pentyl-biphenyl-3-yloxy]-propan-1-ol

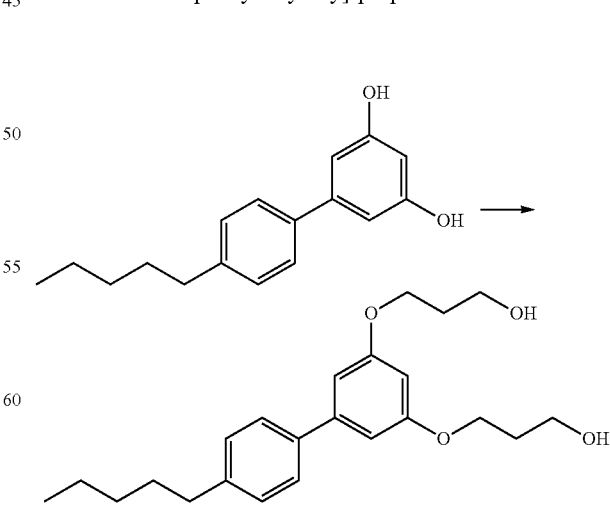

2.70 g (10.5 mmol) 4'-pentylbiphenyl-3,5-diol, 5.86 g (42.1 mmol) 3-bromo-1-propanol and 6.11 g (44.1 mmol)

potassium carbonate are heated in 60 ml ethyl methyl ketone overnight. The reaction is filtered, evaporated and the crude product is purified by chromatography on silica (ethyl acetate/toluene (7:3)) and recrystallised from heptane/ethyl acetate (9:1) to give 3-[5-(3-Hydroxy-propoxy)-4'-pentyl-biphenyl-3-yloxy]-propan-1-ol as colourless crystals, m.p. 90° C.

Example 6. 2-[2-(2-Fluoro-4'-propyl-biphenyl-4-yl)-ethyl]-propane-1,3-diol

6.1 2-[2-(2-Fluoro-4'-propyl-biphenyl-4-yl)-ethyl]-malonic acid diethyl ester

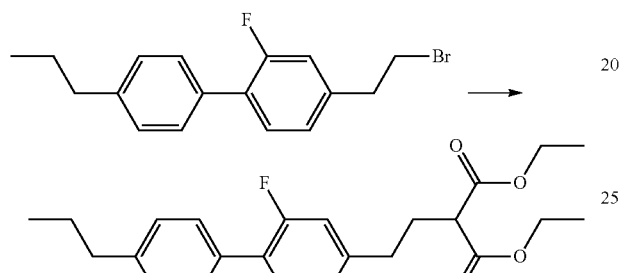

24 ml (0.063 mol) of a 20% solution of sodium ethanoate in ethanol is diluted with 10 ml of ethanol, and 9.5 ml (0.062 mol) ethyl malonate followed by 10.0 g (0.031 mol) 4-(2-Bromo-ethyl)-2-fluoro-4'-propyl-biphenyl are added under reflux. The reaction is refluxed for 2 h, water is added and the solution is extracted three times with MTB-Ether. The combined org. layers are washed with brine and dried over sodium sulfate. The solvent is evaporated and the product is purified by column chromatography with heptane/ethyl acetate (9:1) on silica and excess ethyl malonate is removed by bulb-to-bulb distillation. 2-[2-(2-Fluoro-4-propyl-biphenyl-4-yl)-ethyl]-malonic acid diethyl ester is obtained as yellow oil.

$^1$H NMR (500 MHz, CDCl$_3$)

δ=0.98 ppm (t, J=7.3 Hz, 3H, CH$_3$), 1.28 (t, J=7.1 Hz, 6H, —OCH$_2$CH$_3$), 1.68 (sext., J=7.4 Hz, 2H, CH$_2$), 2.25 (q, J=7.7 Hz, 2H, CH$_2$), 2.63 (dd, J=7.5 Hz, J=7.7 Hz, 2H, CH$_2$), 2.69 (dd, J=7.4 Hz, J=8.1 Hz, 2H, CH$_2$), 3.36 (s, 1H, —CH(COOEt)$_2$), 4.21 (q, J=7.1 Hz, 4H, —OCH$_2$CH$_3$), 6.98 (dd, J=11.6 Hz, J=1.5 Hz, 1H, Ar—H), 7.02 (dd, J=7.8 Hz, J=1.6 Hz, 1H, Ar—H), 7.24 (d, J=8.2 Hz, 2H, Ar—H), 7.34 (t, J=8.0 Hz, 1H, Ar—H), 7.45 (d, J=8.2 Hz, J=1.5 Hz, 2H, Ar—H).

6.2 2-[2-(2-Fluoro-4'-propyl-biphenyl-4-yl)-ethyl]-propane-1,3-diol

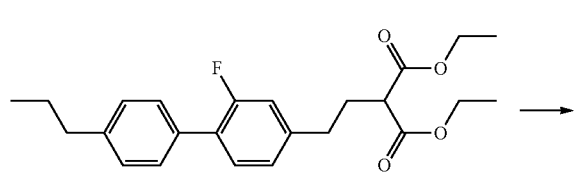

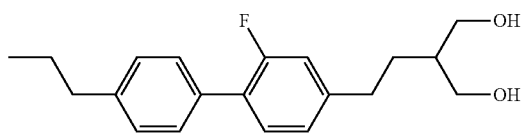

550 mg (14.5 mmol) lithiumaluminiumhydride are suspended in 4 ml toluene and a solution of 4.80 g (12 mmol) 2-[2-(2-Fluoro-4'-propyl-biphenyl-4-yl)-ethyl]-malonic acid diethyl ester in 20 ml THF is added dropwise. The reaction is refluxed for 1 h, poured onto ice-water and acidified with 2 N hydrochloric acid. The aq. layer is separated and extracted three times with MTB-Ether. The combined org. layer are washed with brine, dried over sodium sulfate and the solvent is evaporated. Crystallisation from heptane gave 2-[2-(2-Fluoro-4'-propyl-biphenyl-4-yl)-ethyl]-propane-1,3-diol as a white solid, m.p. 66° C. Phases: K 66 SmC 73 I.

Example 7. 2-[2-(2-Ethyl-4'-propyl-biphenyl-4-yl)-ethyl]-propane-1,3-diol

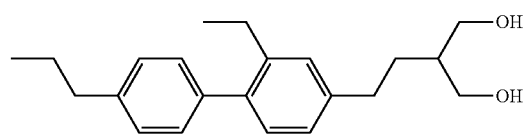 [SMILES: CCCc1ccc(-c2ccc(CCC(CO)CO)cc2CC)cc1]

Analogous to example 6, 2-[2-(2-Ethyl-4'-propyl-biphenyl-4-yl)-ethyl]-propane-1,3-diol is obtained as colourless crystals. M.p.=70° C.

Example 8. 2-[2-(4'-Propyl-biphenyl-4-yl)-ethyl]-propane-1,3-diol

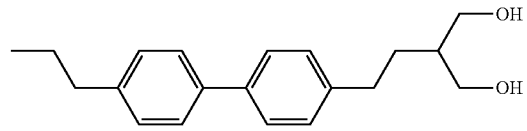 [SMILES: CCCc1ccc(-c2ccc(CCC(CO)CO)cc2)cc1]

Analogous to example 6, 2-[2-(4'-Propyl-biphenyl-4-yl)-ethyl]-propane-1,3-diol is obtained as colourless crystals.

Example 9. 5-[2-(2-Hydroxy-ethoxy)-ethoxy]-4'-pentyl-biphenyl-3-ol

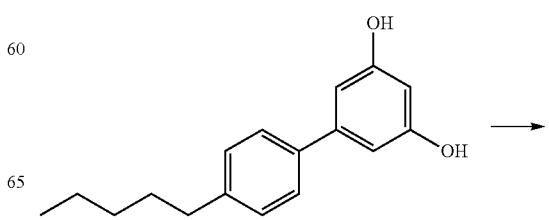

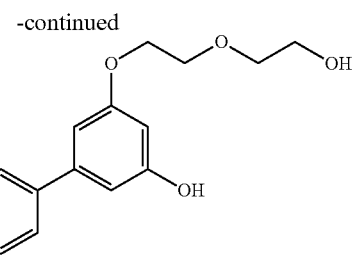

2.90 g (11.3 mmol) 4'-pentylbiphenyl-3,5-diol and 1.41 g (11.3 mmol) 2-(2-Chloro-ethoxy)-ethanol are dissolved in 30 ml DMF, 1.56 g (11.3 mmol) potassium carbonate are added and the reaction is heated at 100° C. for 2 d. After cooling to room temp. the solution is carefully acidified with 1 M hydrochloric acid, diluted with MTB-Ether and washed with brine. The solvent is evaporated and the crude product is purified by chromatography on silica (ethyl acetate/toluene 7:3) and crystallised from heptane/ethyl acetate at −30° C.

5-[2-(2-Hydroxy-ethoxy)-ethoxy]-4'-pentyl-biphenyl-3-ol is obtained as colourless crystals, m.p. 64° C.

Example 10 2-[2-(2'-Ethyl-4''-pentyl-[1,1';4',1'']terphenyl-4-yl)-ethyl]-propane-1,3-diol 10.1 Synthesis of 2-[4-(4,4,5,5-Tetramethyl[1,3,2]dioxaborolan-2-yl)-phenyl]-ethanol A

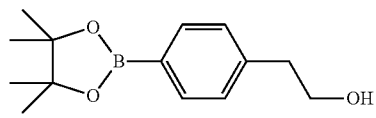

20.0 g (99.5 mmol) 2-(4-Bromo-phenyl)-ethanol, 28.4 g (109.4 mmol) bis-(pinacolato)-diboron, 32.3 g (330 mmol) potassium acetate and 2.5 g (3.4 mmol) PdCl₂dppf are dissolved in 355 ml 1,4-dioxane and are refluxed overnight. The reaction mixture is cooled to room temperature and 300 ml water is added. The mixture is extracted four times with Methyl-tert-butyl ether, washed with brine, dried over sodium sulphate, filtered and evaporated under vacuum. The crude product is purified via silica gel chromatography (toluene/ethyl acetate 4:1) to give 22 g (87% yield) of the product as yellow oil.

10.2 Synthesis of 2-(4'-Bromo-2'-ethyl-biphenyl-4-yl)-ethanol B

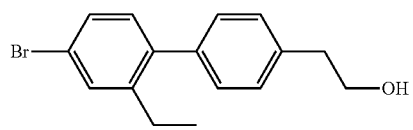

25 g (236 mmol) sodium carbonate is dissolved in 175 ml water and 75 ml ethanol. 29.6 g (95.2 mmol) 4-bromo-2-ethyl-1-iodo-benzene, 23.6 g (95.0 mmol) boronic ester A are dissolved in 375 ml toluene added to the reaction mixture. After adding Pd(PPh₃)₄ to the mixture it is refluxed for 5.5 h and cooled to room temperature. The organic phase is separated and the water phase is extracted two times with ethyl acetate. The combined organic phases are washed with brine, dried over sodium sulphate, filtered and evaporated under vacuum. The crude product is purified via silica gel chromatography (heptane/ethyl acetate 8:2) and (toluene/ethyl Acetate 95:5) to give 24.5 g (80% yield) of the product.

10.3 Synthesis of 2-(2'-Ethyl-4''-pentyl-[1,1';4',1'']terphenyl-4-yl)-ethanol C

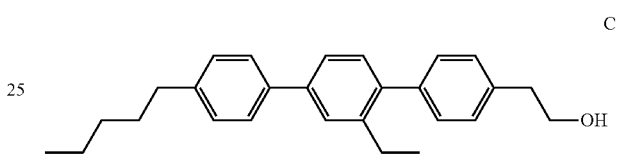

14.2 g (101 mmol) sodium metaborate tetrahydrate are dissolved in 215 ml water and added with 960 mg (1.34 mmol) Pd(PPh₃)₂Cl₂, 0.065 ml hydrazinium hydroxide, 21.5 g (67.0 mmol) of bromine B and 25 ml THF. The mixture is stirred for 5 min and then added with 12.9 g (67.2 mmol) 4-(pentylphenyl) boronic acid in 50 ml THF. The reaction mixture is refluxed for 16 h and cooled to room temperature. The reaction product is extracted with methyl-tert-butyl ether and the organic layer is washed with brine, dried over sodium sulphate, filtered and evaporated under vacuum. The crude product is purified via silica gel chromate-grapy (toluene/heptane 1:1) and afterwards crystallized from heptane to give 17.8 g (71% yield) of the product as white crystals.

10.4 4-(2-Bromo-ethyl)-2'-ethyl-4''-pentyl-[1,1';4',1'']terphenyl D

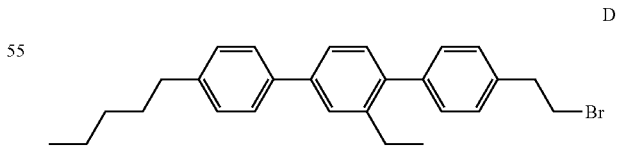

17.8 g (48.0 mmol) of alcohol C is solved in 93.0 ml (0.81 mol) of hydrobromic acid. The reaction mixture is refluxed for 16 h and cooled to room temperature. 50 ml of water are added and the layers separated. The product layer washed with brine, filtered, evaporated under vacuum and purified via silica gel chromatography with heptane/ethyl acetate (9:1) to give 15.6 g (73% yield) of the product as an oil.

10.5 Synthesis of 2-[2-(2'-Ethyl-4"-pentyl-[1,1';4',1"]terphenyl-4-yl)-ethyl]-malonicacid diethyl ester E

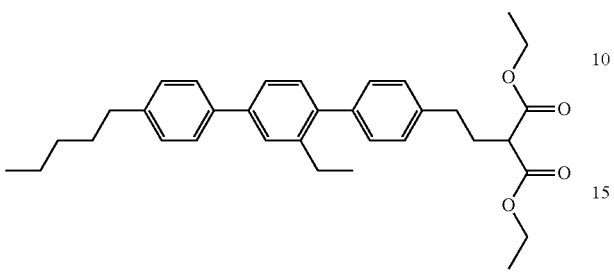

To 45 ml (0.77 mol) ethanol are added 1.5 g (65 mmol) sodium metal in small portions. (caution: $H_2$ formation) Afterwards are added 16.7 ml (109 mmol) diethylmalonate and 29.6 g (69 mmol) bromide D in 5 ml ethanol. The reaction mixture is then refluxed for 2.5 h and cooled to room temperature and evaporated. It is added with water and methyl-tert-butyl ether and ethyl acetate. The combined organic layers are washed with brine, dried with sodium hydrogen sulphate, filtered and evaporated under vacuum. The crude product is purified via silica gel chromatography (heptane/ethyl acetate 9:1) to give 15.5 g (44% yield) of the product.

10.6 2-[2-(2'-Ethyl-4"-pentyl-[1,1';4',1"]terphenyl-4-yl)-ethyl]-propane-1,3-diol F

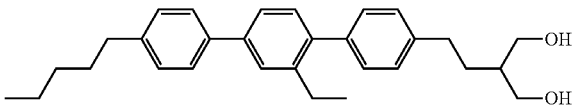

0.66 g (17.4 mmol) $LiAlH_4$ powder is added to 3.6 ml toluene. Afterwards 15 ml THF are cautiously added and, at 0 to 10° C., 7.5 g (0.14 mmol) of malonic ester E dissolved in 30 ml THF are slowly added. After complete addition the reaction mixture is stirred at 65° C. for 3.5 h, then cooled to 5° C. and very cautiously quenched with a 10 ml THF-water (1:1) mixture ($H_2$ generation!). The white suspension is treated with 2 N HCl until a pH value of 1 is reached. 50 ml of water are added and the mixture is extracted with 100 ml of ethyl ether. The organic layer is separated, washed with water, brine and dried over sodium sulphate. It is filtered and evaporated under vacuum. The crude product is purified via silica gel chromatography with heptane and heptane/ethyl acetate (8:2). The obtained product is finally crystallized from heptane and the product is obtained as white crystals with 3.5 g (58% yield).

Phases: Tg–25 K 79 SmA 96 I $^1$H NMR (500 MHz, DMSO-$d_6$):

δ=0.88 ppm (t, 7.02 Hz, 3H, $CH_3$), 1.08 ppm (t, 7.54 Hz, 3H, $CH_3$), 1.32 ppm ($m_c$, 4H, $CH_2$—H), 1.6 ppm (m, 5H, $CH_2$—H, $CH(CH_2OH)_2$), 2.64 ppm (m, 6H, arom.-$CH_2$), 3.45 ppm ($m_c$, 4H, $CH_2OH$), 4.34 ppm (t, 5.2 Hz, 2H, OH), 7.25 ppm (m, 7H, arom.-H), 7.48 ppm (dd, 7.92 Hz, 1.97 Hz, 1H, arom.-H), 7.57 ppm (d, 1.92 Hz, 1H, arom.-H), 7.60 ppm (d, 8.2 Hz, 2H, arom.-H).

Example 11. 2-[2-(4'-Propyl-bicyclohexyl-4-yl)-ethoxy]-propane-1,3-diol

11.1 4'-[2-(2-Benzyloxy-1-benzyloxymethyl-ethoxy)-ethyl]-4-propyl-bicyclohexyl

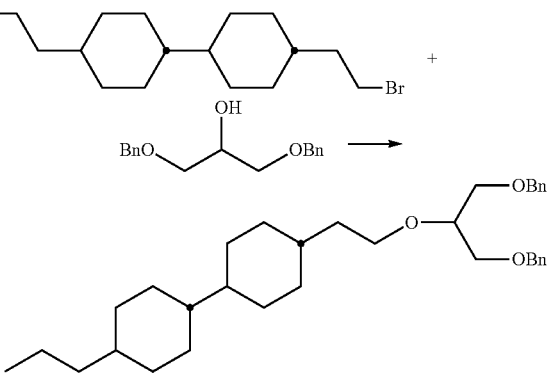

9.9 g (35 mmol) 1,3-dibenzyloxypropan-2-ol are dissolved in 20 ml DMF and added dropwise at 0° C. to a suspension of 1.8 g (44 mmol) sodium hydride (60% in paraffin oil) in 30 ml of DMF. After the effervescence had ceased, the cooling bath is removed and a solution of 9.3 g (29 mmol) 4'-(2-bromo-ethyl)-4-propyl-bicyclohexyl in 50 ml DMF is added. The reaction is stirred overnight, poured onto ice water, acidified with 2 M hydrochloric acid and extracted tree times with MTB-Ether. The combined org. layers are washed with brine, dried over sodium sulfate and evaporated. The crude 4'-[2-(2-benzyloxy-1-benzyloxymethyl-ethoxy)-ethyl]-4-propyl-bicyclohexyl is obtained as colourless oil which is used in the next step without further purification.

$^1$H NMR (500 MHz, $CDCl_3$)

δ=0.78-1.18 ppm (m, 17H, aliphatic H, therein: 0.87 (t, J=7.4 Hz, $CH_3$), 1.22-1.35 (m, 3H, aliphatic H), 1.47 (q, J=6.9 Hz, 1H, aliphatic H), 1.65-1.81 (m, 8H, aliphatic-H), 3.53-3.69 (m, 6H, —$CH_2O$—), 4.06 (tt, J=4.5 Hz, J=6.2 Hz, 1H, —$OCH(CH_2O—)_2$—), 4.59 (s, 4H, $PhCH2O$—), 7.38-7.42 (m, 10H, Ar—H).

11.2 2-[2-(4'-Propyl-bicyclohexyl-4-yl)-ethoxy]-propane-1,3-diol

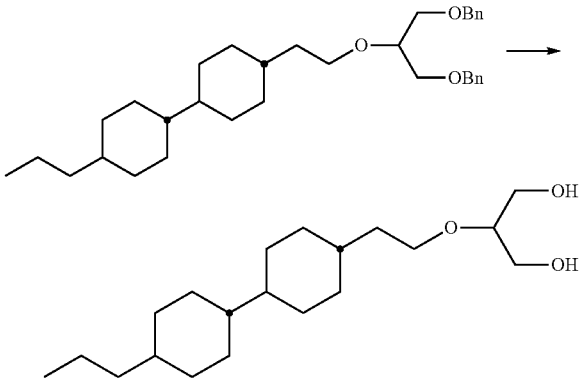

5.00 g (9.87 mmol) 4'-[2-(2-benzyloxy-1-benzyloxymethyl-ethoxy)-ethyl]-4-propyl-bicyclohexyl in THF are hydrogenated in the presence of palladium in charcoal until the reaction ceased. The solution is filtered, evaporated and the crude product is recrystallised from ethanol to give 2-[2-(4'-propyl-bicyclohexyl-4-yl)-ethoxy]-propane-1,3-diol as colourless crystals.

Example 12. 2-(2-{2-Ethyl-2'-fluoro-4'-[2-(4-pentyl-phenyl)-ethyl]-biphenyl-4-yl}-ethyl)-propane-1,3-diol

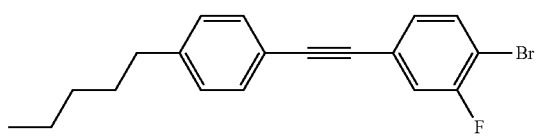

12.1 1-Bromo-2-fluoro-4-(4-pentyl-phenylethynyl)-benzene A

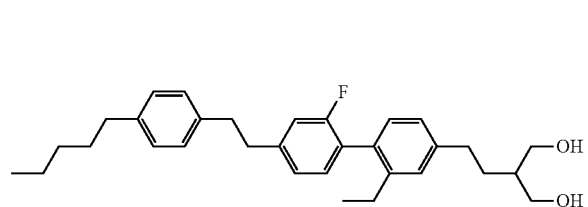 [SMILES: CCCCCc1ccc(CCc2ccc(-c3ccc(CCC(CO)CO)cc3CC)c(F)c2)cc1]

86.0 g (0.286 mol) of 4-bromo-2-fluoro-1-iodo-benzene, 4.5 g (6.41 mmol) Pd(PPh$_3$)$_2$Cl$_2$ and 1.20 g (6.30 mmol) of CuI are solved at RT in 500 ml triethylamine and properly degassed. 50.0 g (0.290 mol) of 1-ethynyl-4-pentyl-benzene is solved in 100 ml triethylamine and added dropwise to the mixture. The reaction temperature rises during the addition of the alkine and the reaction mixture is stirred at room temperature for 18 h. The reaction mixture is diluted with water, extracted with methyl tert-butyl ether and dried over Na$_2$SO$_4$. After evaporation of the solvent the crude product is purified via column chromatography with heptane and the product is obtained as a yellow solid.

12.2 Synthesis of Boronic Acid B 139.5 g (0.404 mol) of product A are dissolved in 1000 ml THF and cooled to −78° C. and 260 ml (1.6 M in hexane, 0.42 mol) of n-butyllithium are added dropwise at this temperature. After stirring for 15 min at −78° C. 50.0 ml (0.44 mol) of trimethyl borate is added dropwise and the resulting reaction mixture is stirred over night (18 h) with temperature rising up to room temperature during this time. The reaction mixture is acidified at 0° C. with 2 N HCl and the organic layer is separated, dried over brine and evaporated under vacuum to give the product B as slightly yellow crystals.

$^1$H NMR (500 MHz, CDCl$_3$): δ=0.93 ppm (t, 6.9 Hz, 3H, CH$_3$), 1.36 ppm (m$_c$, 4H, CH$_2$—H), 1.65 ppm (quint., 7.5 Hz, 2H, CH$_2$), 2.65 ppm (t, 7.8 Hz, 2H, CH$_2$), 7.20 ppm (d, 8.2 Hz, 3H, Ar.—H), 7.29 ppm (dd, 8.2 Hz, 1.8 Hz, 1H, Ar—H), 7.46 ppm (d, 8.2 Hz, 2H, Ar—H), 7.53 ppm (dd, 8.3 Hz, 8.2 Hz, 1H, Ar.—H).

12.3 Synthesis of 4'-Bromo-2'-ethyl-2-fluoro-4-(4-pentyl-phenylethynyl)-biphenyl C

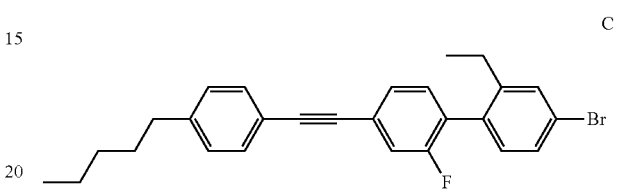

28.2 g (0.266 mol) Na$_2$CO$_3$ is dissolved in 100 ml water and to this 207 ml toluene and 33.2 g (106.9 mmol) of 4-bromo-2-ethyl-1-iodo-benzene are added. The mixture is heated to 75° C., 3.8 g (3.3 mmol) Pd(PPh$_3$)$_4$ are added and immediately a solution of boronic acid B (33.4 g [0.107 mol] in 33.2 ml ethanol is added during 15 min. The reaction mixture is refluxed for 18 h and is diluted with toluene and washed with water. The organic layer is washed with brine, dried over Na$_2$SO$_4$ and evaporated under vacuum. Raw material C is purified with heptane and heptane/toluene (10:1) via column chromatography and the product is obtained as a white solid.

12.4 Synthesis of 2-[2-Ethyl-2'-fluoro-4'-(4-pentyl-phenylethynyl)-biphenyl-4-yl]-ethano D

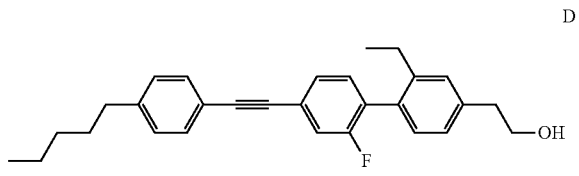 [SMILES: CCCCCc1ccc(C#Cc2ccc(-c3ccc(CCO)cc3CC)c(F)c2)cc1]

35.9 g (77.0 mmol) of bromide C is solved in 100 ml THF and cooled to −78° C. and n-butyl-lithium (51 ml, 1.6 M, [82.0 mmol]) is added dropwise. To the reaction mixture is added 4.1 g (93.0 mmol) of ethylene oxide in 10 ml cooled (0° C.) THF and after 30 min stirring at −78° C. 10.1 ml (80.0 mmol) of boron trifluoride etherate in 40 ml THF is added cautiously dropwise (exothermic reaction). The reaction mixture is allowed to rise to room temperature during 5 h and is then poured into ice water and extracted with methyl-tert-butyl ether. The combined organic layers are washed with brine and dried over Na$_2$SO$_4$ and evaporated under vacuum. The crude product is filtered via column chromatography and the product is obtained as a solid material.

12.5 Synthesis of 2-{2-Ethyl-2'-fluoro-4'-[2-(4-pentyl-phenyl)-ethyl]-biphenyl-4-yl}-ethanol

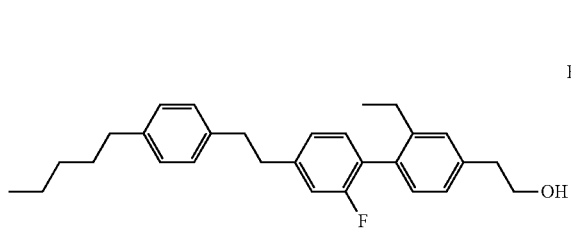

21.8 g (51.0 mmol) of alkine D is dissolved in 200 ml THF and to this 4.40 g Pd—C (5%/E101R/54% H$_2$O, Degussa) is added. The triple bond is reduced with H$_2$ (3.0 PRAX Air GmbH) at normal pressure and RT within 32 h after an additional addition of 4.4 g Pd—C after 16 h. The reaction mixture is filtered with silica gel with toluene/methyl tert-butyl ether (9:1) and evaporated under vacuum to give alcohol E.

12.6 Synthesis of methanesulfonic acid 2-{2-ethyl-2'-fluoro-4'-[2-(4-pentyl-phenyl)-ethyl]-biphenyl-4-yl}-ethyl ester F

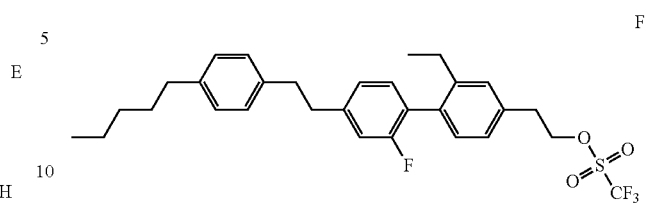

21.8 g (52.0 mmol) of alcohol E and 600 mg (4.91 mmol) 4-dimethylaminopyridine is solved in 100 ml dichloromethane and 9.5 ml (117.7 mmol) pyridine is added. The reaction mixture is cooled to 0° C. and 4.80 ml (62.0 mmol) methanesulfonylchloride is added. The mixture is stirred for 18 h and the temperature is allowed to rise up to room temperature during that time. After complete conversion the mixture is diluted with water and extracted with dichloromethane. The organic layer is washed with 2 N HCl and water, dried with Na$_2$SO$_4$ and evaporated under vacuum. The crude product is filtered over silica gel with dichloromethane and the product is obtained as a colourless oil.

12.7 2-(2-{2-Ethyl-2'-fluoro-4'-[2-(4-pentyl-phenyl)-ethyl]-biphenyl-4-yl}-ethyl)-propane-1,3-diol (Example 12)

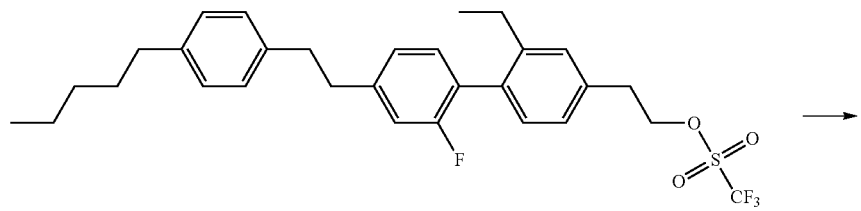

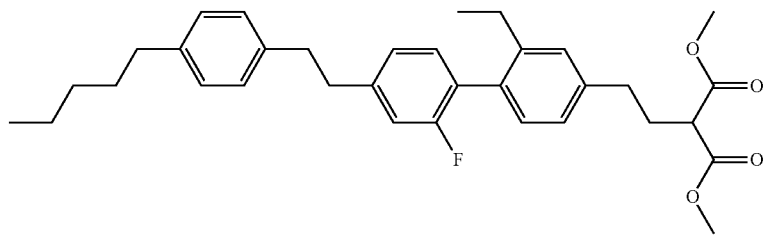

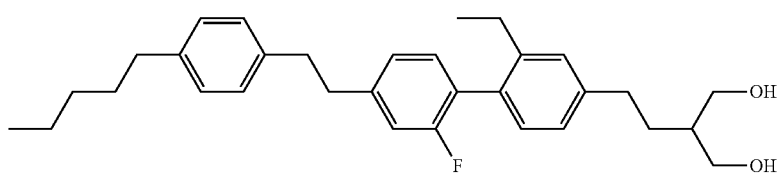

The synthetic transformations starting from F via G are done under the same reaction conditions like shown in the synthesis examples 10.5 and 10.6.

The title product is obtained as a colourless oil which, after extended cooling at −20° C., crystallizes to a white solid (mp.=35° C.).

Phases: Tg−34 Sm 21 K [35] I $^1$H NMR (500 MHz, CDCl$_3$): δ=0.89 ppm (t, 7.0 Hz, 3H, CH$_3$), 1.07 ppm (t, 7.6 Hz, 3H, CH$_3$), 1.32 ppm (m$_c$, 4H, CH$_2$—H), 1.64 ppm (m, 4H), 1.86 ppm (m$_c$, 1H, CH(CH$_2$OH)$_2$), 2.19 ppm (t, 4.9 Hz, 2H, OH), 2.49 ppm (q, 7.5 Hz, 2H, CH$_2$), 2.58 ppm (dd, 7.9 Hz, 2H, CH$_2$), 2.70 ppm (dd, 8.0 Hz, 2H, CH$_2$), 2.94 (s, 4H, CH$_2$), 3.74 ppm (m$_c$, 2H, CH$_2$OH), 3.89 ppm (m$_c$, 2H, CH$_2$OH), 6.94 ppm (dd, 10.6 Hz, 1.5 Hz, 1H, Arom.-H), 6.99 ppm (dd, 7.74 Hz, 1.6 Hz, 1H, Arom.-H), 7.11 ppm (m, 8H, Arom.-H).

The following compounds for use in LC media are prepared analogously or in accordance with a literature procedure.

According to Examples 4 and 5 the following compounds are synthesised:

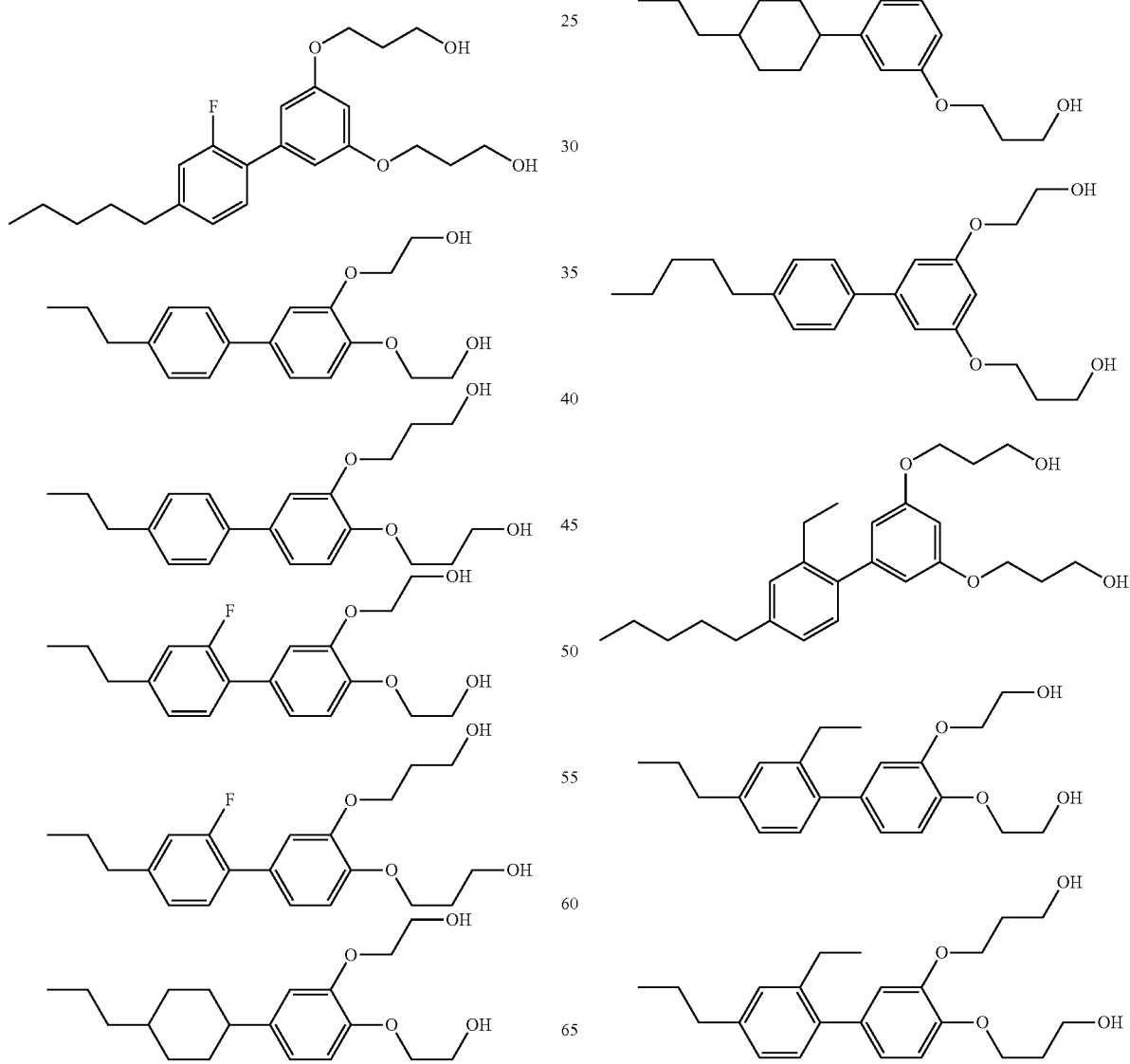

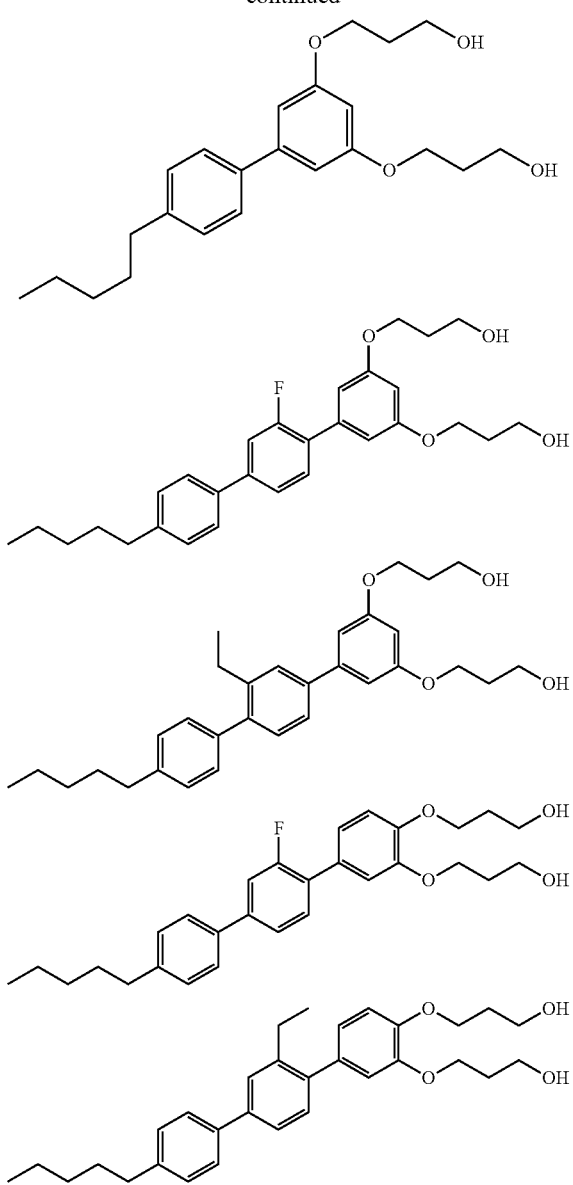
According to Example 6 or 11 the following compounds are synthesized:
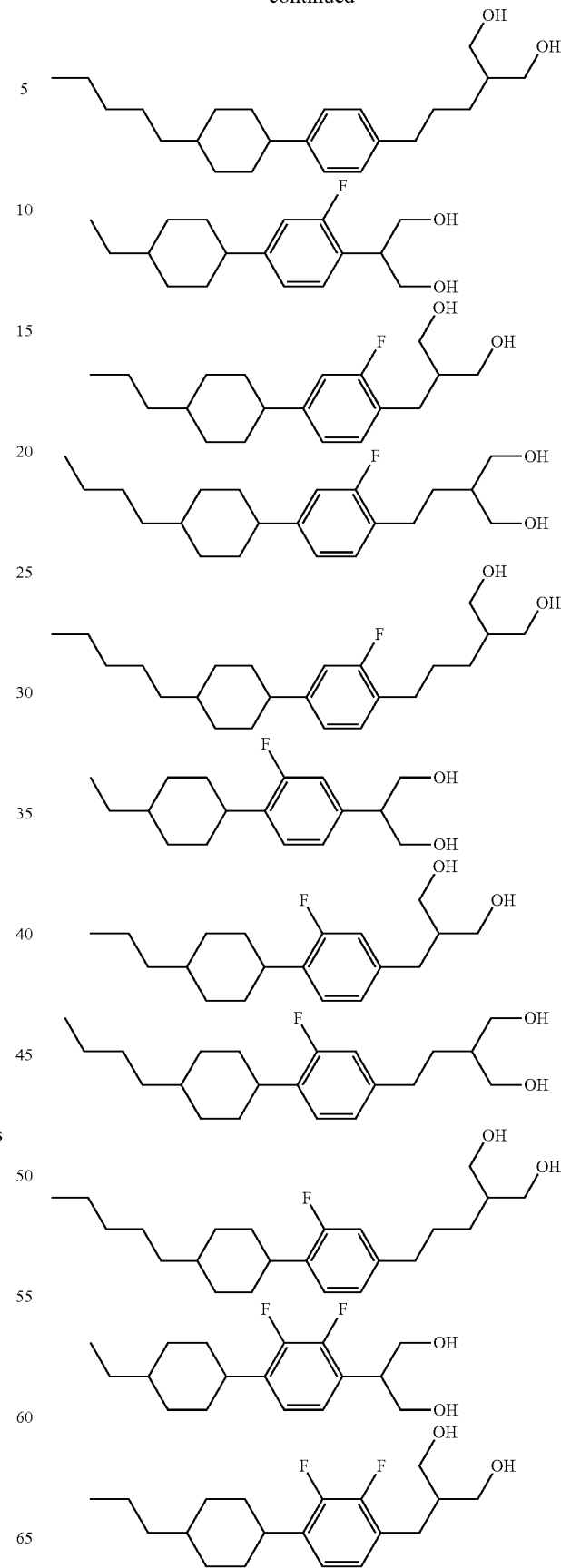

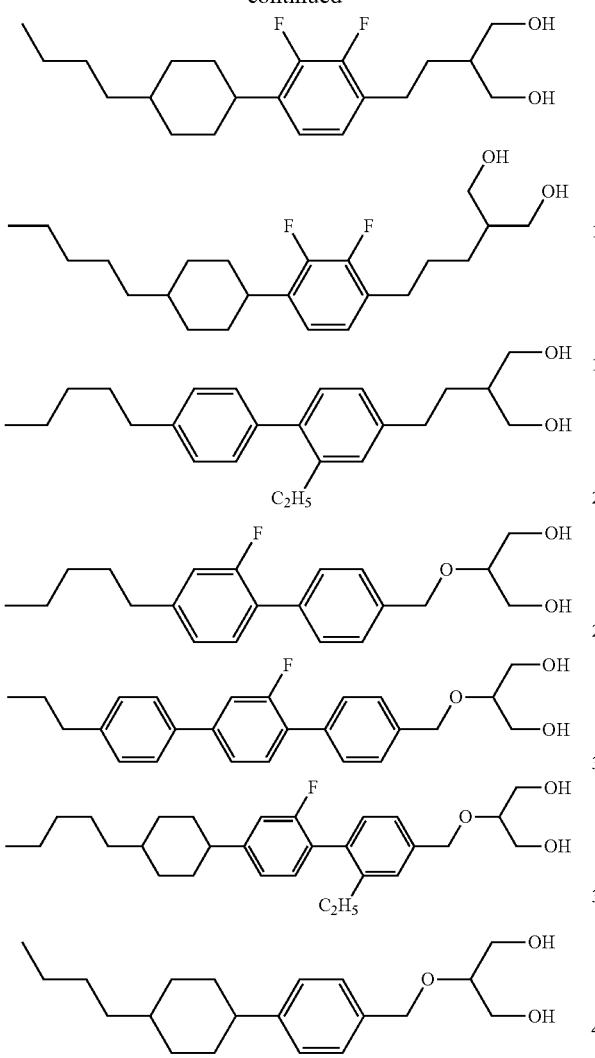
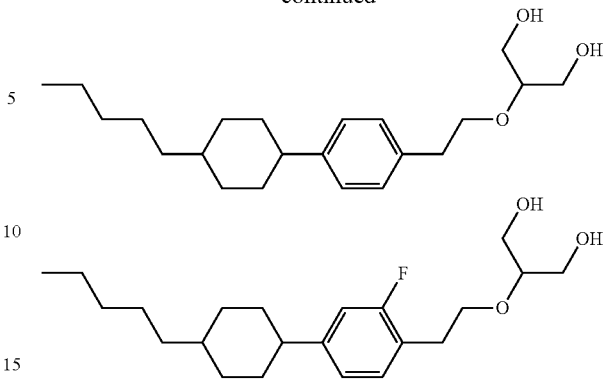
From the above alcohols, amines are prepared.
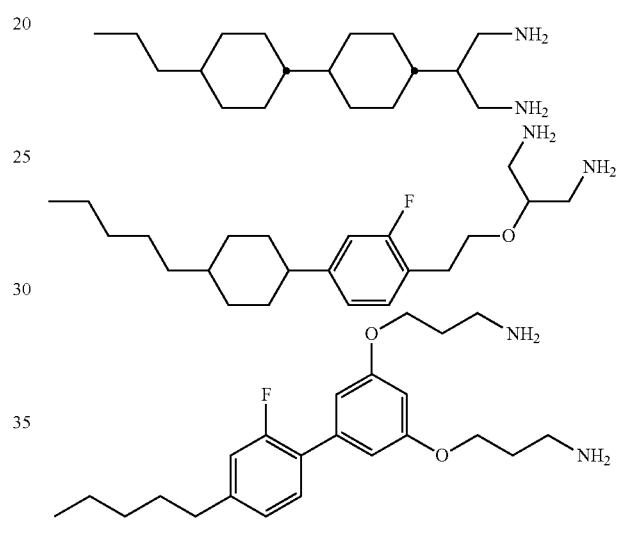
According to the example 12 the following molecules are synthesized:
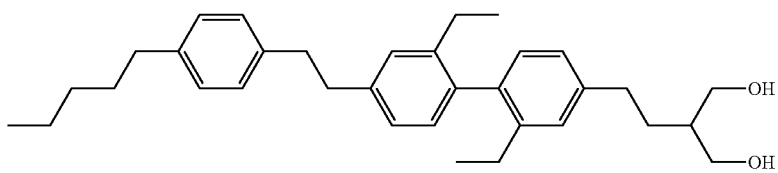
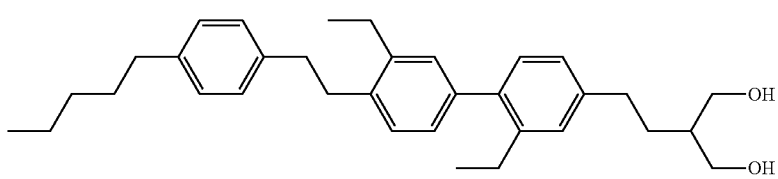
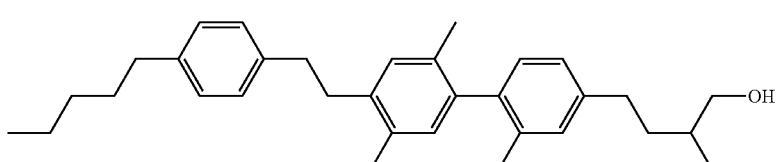

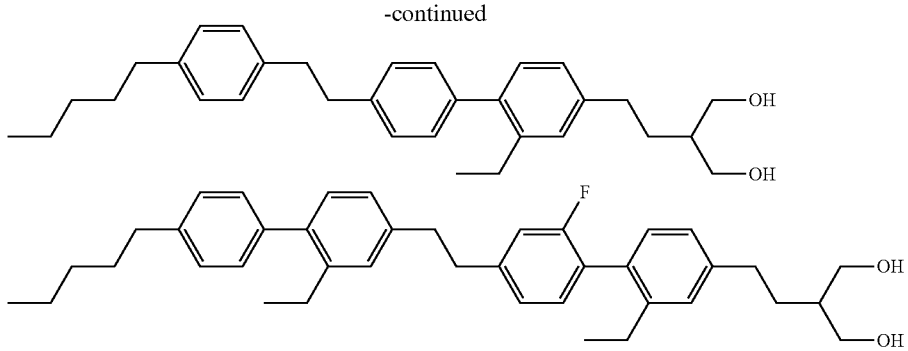

Mixture Examples

For the preparation of the LC media according to the invention, the following liquid-crystalline mixtures consisting of low-molecular-weight components in the stated percentage proportions by weight are used.

TABLE 1

| Nematic LC medium M1 ($\Delta\epsilon < 0$) | | | |
|---|---|---|---|
| CY-3-O2 | 15.5% | Cl.p. | +75° C. |
| CCY-3-O3 | 8% | $\Delta n$ | 0.098 |
| CCY-4-O2 | 10% | $\Delta\epsilon$ | −3.0 |
| CPY-2-O2 | 5.5% | $\epsilon_{\parallel}$ | 3.4 |
| CPY-3-O2 | 11.5% | $K_3/K_1$ | 1.02 |
| CCH-34 | 9.25% | | |
| CCH-23 | 24.5% | | |
| PYP-2-3 | 8.75% | | |
| PCH-301 | 7% | | |

TABLE 2

| Nematic LC medium M2 ($\Delta\epsilon < 0$) | | | |
|---|---|---|---|
| CY-3-O4 | 14% | Cl.p. | +80° C. |
| CCY-3-O2 | 9% | $\Delta n$ | 0.090 |
| CCY-3-O3 | 9% | $\Delta\epsilon$ | −3.3 |
| CPY-2-O2 | 10% | $\epsilon_{\parallel}$ | 3.4 |
| CPY-3-O2 | 10% | $K_3/K_1$ | 0.97 |
| CCY-3-1 | 8% | | |
| CCH-34 | 9% | | |
| CCH-35 | 6% | | |
| PCH-53 | 10% | | |
| CCH-301 | 6% | | |
| CCH-303 | 9% | | |

TABLE 3

| Nematic LC medium M3 ($\Delta\epsilon < 0$) | | | |
|---|---|---|---|
| CC-4-V | 10% | Cl.p. | +77° C. |
| CC-5-V | 13.5% | $\Delta n$ | 0.113 |
| PGU-3-F | 6.5% | $\Delta\epsilon$ | 19.2 |
| ACQU-2-F | 10% | $\epsilon_{\parallel}$ | 23.8 |
| ACQU-3-F | 12% | $K_3/K_1$ | 0.97 |
| PUQU-3-F | 11% | | |
| CCP-V-1 | 12% | | |
| APUQU-2-F | 6% | | |
| APUQU-3-F | 7% | | |
| PGUQU-3-F | 8% | | |
| CPGU-3-OT | 4% | | |

The following compounds 1 to 40 are used as self-aligning additives:

| Compound No. | Structure |
|---|---|
| 1 | 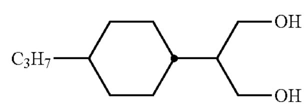 |
| 2 | 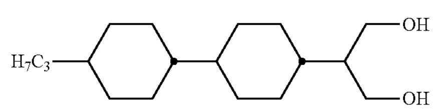 |
| 3 | 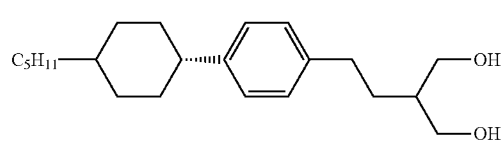 |

-continued

| Compound No. | Structure |
|---|---|
| 4 | C₃H₇—⟨phenyl⟩—⟨phenyl⟩—CH₂CH₂CH(CH₂OH)CH₂OH |
| 5 | C₃H₇—⟨phenyl⟩—⟨phenyl(2-F)⟩—CH₂CH₂CH(CH₂OH)CH₂OH |
| 6 | C₃H₇—⟨phenyl⟩—⟨phenyl(2-C₂H₅)⟩—CH₂CH₂CH(CH₂OH)CH₂OH |
| 7 | C₅H₁₁—⟨phenyl⟩—⟨phenyl(2-C₂H₅)⟩—CH₂CH₂CH(CH₂OH)CH₂OH |
| 8 | C₅H₁₁—⟨phenyl(2-F)⟩—⟨phenyl(2-C₂H₅)⟩—CH₂CH₂CH(CH₂OH)CH₂OH |
| 9 | C₅H₁₁—⟨phenyl(2-F)⟩—⟨phenyl⟩—CH₂CH₂CH₂CH(CH₂OH)CH₂OH |
| 10 | C₅H₁₁—⟨phenyl(2-F)⟩—⟨phenyl(2-C₂H₅)⟩—CH₂CH₂CH₂CH(CH₂OH)CH₂OH |
| 11 | C₃H₇—⟨cyclohexyl⟩—⟨cyclohexyl⟩(CH₂CH₂OH)(CH₂CH₂OH) |
| 12 | C₅H₁₁—⟨phenyl⟩—⟨phenyl(3,5-di(OCH₂CH₂OH))⟩ |

-continued

| Compound No. | Structure |
|---|---|
| 13 | C5H11-C6H4-C6H3(OCH2CH2CH2OH)(OCH2CH2CH2OH) |
| 14 | C5H11-C6H4-C6H3(OH)(OCH2CH2OCH2CH2OH) |
| 15 | C5H11-C6H4-C6H3(CH2CH2CH2OH)(CH2CH2CH2OH) |
| 16 | C3H7-C6H4-C6H3(C2H5)-CH2CH2-C(CH2OH)3 |
| 17 | C3H7-C6H4-CH2CH2-C6H3(C3H5)-CH2CH2-CH(CH2OH)2 |
| 18 | C5H11-C6H10-C6H4-C6H3(C2H5)-CH2CH2-CH(CH2OH)2 |
| 19 | C5H11-C6H10-C6H4-C6H3(C2H5)-CH2CH2CH2-CH(CH2OH)2 |
| 20 | C5H11-C6H10-C6H3(F)-C6H3(C2H5)-CH2CH2-CH(CH2OH)2 |
| 21 | C5H11-C6H4-C6H3(C2H5)-C6H4-CH2CH2-CH(CH2OH)2 |

-continued
| Compound No. | Structure |
|---|---|
| 22 | 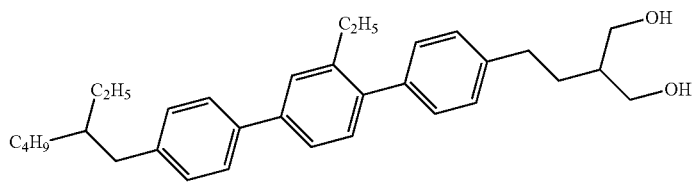 |
| 23 | 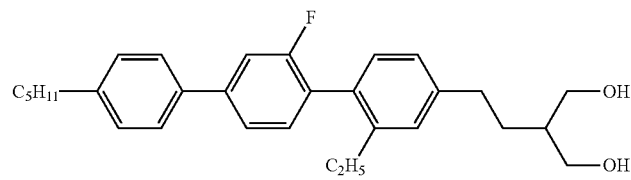 |
| 24 | 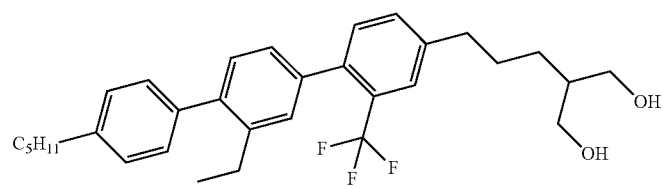 |
| 25 | 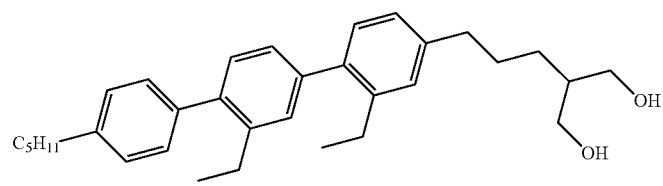 |
| 26 | 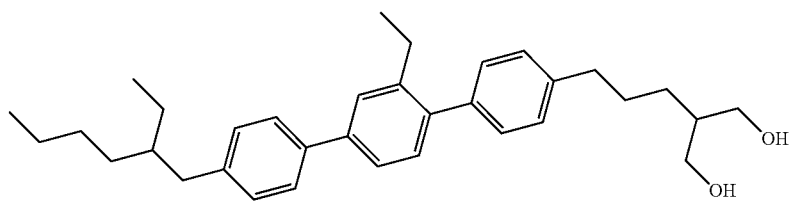 [SMILES: CCCCC(CC)Cc1ccc(-c2ccc(-c3ccc(CCCC(CO)CO)cc3)c(CC)c2)cc1] |
| 27 | 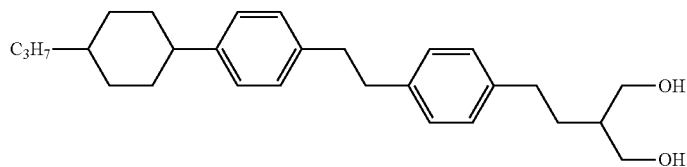 |
| 28 | 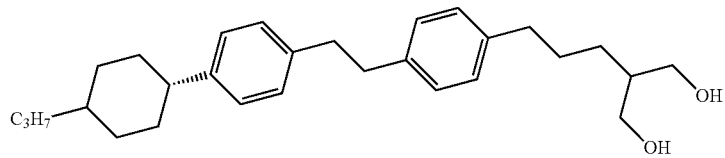 |
| 29 | 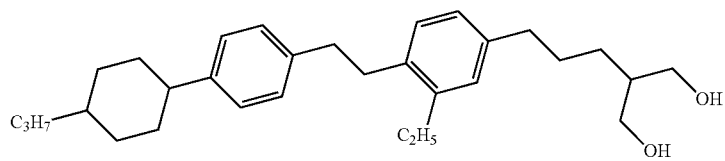 |

-continued

| Compound No. | Structure |
|---|---|
| 30 | C₃H₇–(cyclohexyl)–(C₆H₄)–CH₂CH₂–(C₆H₃ with CHF₂)–CH₂CH₂CH₂–CH(CH₂OH)(CH₂OH) |
| 31 | C₃H₇–(cyclohexyl)–(C₆H₄)–CH₂CH₂–(C₆H₃ with CF₃)–CH₂CH₂CH₂–CH(CH₂OH)(CH₂OH) |
| 32 | C₃H₇–(C₆H₄)–(C₆H₄)–CH₂CH₂–(C₆H₄)–CH₂CH(CH₂OH)(CH₂OH) |
| 33 | C₃H₇–(C₆H₄)–(C₆H₄)–CH₂CH₂–(C₆H₄)–CH₂CH₂CH(CH₂OH)(CH₂OH) |
| 34 | C₅H₁₁–(C₆H₄)–CH₂CH₂–(C₆H₄)–(C₆H₃ with C₂H₅)–CH₂CH₂CH(CH₂OH)(CH₂OH) |
| 35 | C₅H₁₁–(C₆H₄)–CH₂CH₂–(C₆H₃ with F)–(C₆H₃ with C₂H₅)–CH₂CH(CH₂OH)(CH₂OH) |
| 36 | C₅H₁₁–(C₆H₄)–CH₂CH₂–(C₆H₃ with C₂H₅)–(C₆H₃ with C₂H₅)–CH₂CH₂CH(CH₂OH)(CH₂OH) |
| 37 | C₅H₁₁–(C₆H₄)–CH₂CH₂–(C₆H₃ with C₂H₅)–(C₆H₃ with C₂H₅)–CH₂CH₂CH(CH₂OH)(CH₂OH) |

-continued

| Compound No. | Structure |
|---|---|
| 38 | [structure: C5H11-phenyl-CH2CH2-phenyl-biphenyl(C2H5)-CH2CH2CH(CH2OH)CH2OH with OH] |
| 39 | [structure: C5H11-phenyl-phenyl(C2H5)-CH2CH2-phenyl(F)-phenyl(C2H5)-CH2CH2CH(CH2OH)CH2OH] |
| 40 | [structure: C3H7-cyclohexyl-phenyl-C≡C-phenyl(C2H5)-C≡C-CH2CH(CH2OH)CH2OH] |

The following polymerizable mesogens are employed:

RM-1

RM-2

RM-3

RM-4

Mixture Example 1

The compound no. 1 (0.5% by weight) is added to the nematic LC medium M1 of the VA type (Δ∈<0, Table 1) and the mixture is homogenised.

Use in Test Cells without Pre-Alignment Layer:

The resulting mixture is introduced into a test cell (without polyimide alignment layer, LC layer thickness d≈4.0 μm, ITO coating on both sides (structured ITO in case of a multi-domain switching), no passivation layer). The LC medium has spontaneous homeotropic (vertical) alignment to the substrate surfaces. In the temperature-stable range, the VA cell can be switched reversibly between crossed polarisers by application of a voltage of between 0 and 30 V.

Mixture Example 2

The compound 1 (0.5% by weight) is added to a nematic LC medium M3 of the VA-IPS type (Δ∈>0, Table 3) and the mixture is homogenised.

Use in Test Cells without Pre-Alignment Layer:

The resulting mixture is introduced into a test cell (without polyimide alignment layer, layer thickness d≈4 μm, ITO interdigital electrodes arranged on a substrate surface, glass on the opposite substrate surface, no passivation layer). The LC medium has spontaneous homeotropic (vertical) alignment to the substrate surfaces. In the temperature-stable range, the VA-IPS cell can be switched reversibly between crossed polarisers by application of a voltage of between 0 and 20 V.

Mixture Examples 3-41

The compounds 2 to 40 are added analogously to Mixture Example 1 to a nematic LC medium M1 ($\Delta\epsilon<0$) and the mixture is homogenised. The proportions by weight of the compounds in the medium are indicated in Table 4. The resulting LC medium is in each case introduced into a test cell as in Mixture Example 1 (without pre-alignment layer) and shows spontaneous homeotropic (vertical) alignment to the substrate surfaces. In the temperature-stable range, the VA cell can be switched reversibly between crossed polarisers by application of a voltage of between 0 and 30 V.

TABLE 4

Proportions by weight for self-aligning additive in M1 and alignment of the resulting cell at 20° C. Test cell of the VA type.

| Mixture Example No. | Compound No. | Proportion by weight | Alignment at 20° C./ switchable |
|---|---|---|---|
| 3 | 2 | 0.25% | homeotropic/yes |
| 4 | 3 | 0.25% | homeotropic/yes |
| 5 | 4 | 0.25% | homeotropic/yes |
| 6 | 5 | 0.25% | homeotropic/yes |
| 7 | 6 | 0.25% | homeotropic/yes |
| 8 | 7 | 0.25% | homeotropic/yes |
| 9 | 8 | 0.25% | homeotropic/yes |
| 10 | 9 | 0.25% | homeotropic/yes |
| 11 | 10 | 0.25% | homeotropic/yes |
| 12 | 11 | 0.4% | homeotropic/yes |
| 13 | 12 | 0.4% | homeotropic/yes |
| 14 | 13 | 0.4% | homeotropic/yes |
| 15 | 14 | 0.4% | homeotropic/yes |
| 16 | 15 | 0.35% | homeotropic/yes |
| 17 | 16 | 0.1% | homeotropic/yes |
| 18 | 17 | 0.3% | homeotropic/yes |
| 19 | 18 | 0.15% | homeotropic/yes |
| 20 | 19 | 0.15% | homeotropic/yes |
| 21 | 20 | 0.15% | homeotropic/yes |
| 22 | 21 | 0.15% | homeotropic/yes |
| 23 | 22 | 0.15% | homeotropic/yes |
| 24 | 23 | 0.15% | homeotropic/yes |
| 25 | 24 | 0.15% | homeotropic/yes |
| 26 | 25 | 0.15% | homeotropic/yes |
| 27 | 26 | 0.15% | homeotropic/yes |
| 28 | 27 | 0.2% | homeotropic/yes |
| 29 | 28 | 0.2% | homeotropic/yes |
| 30 | 29 | 0.2% | homeotropic/yes |
| 31 | 30 | 0.2% | homeotropic/yes |
| 32 | 31 | 0.2% | homeotropic/yes |
| 33 | 32 | 0.2% | homeotropic/yes |
| 34 | 33 | 0.2% | homeotropic/yes |
| 35 | 34 | 0.2% | homeotropic/yes |
| 36 | 35 | 0.2% | homeotropic/yes |
| 37 | 36 | 0.2% | homeotropic/yes |
| 38 | 37 | 0.2% | homeotropic/yes |
| 39 | 38 | 0.3% | homeotropic/yes |
| 40 | 39 | 0.2% | homeotropic/yes |
| 41 | 40 | 0.15% | homeotropic/yes |

Results for Medium M2:

According to Mixture Example 1, further mixtures with compounds 1 to 40 are prepared with the LC medium M2, employing the same proportions by weight as reported in Table 4. Each resulting LC medium is introduced into a test cell according to Mixture Example 1 without pre-alignment layer. It has spontaneous homeotropic (vertical) alignment to the substrate surfaces. In the temperature-stable range, the VA cell can be switched reversibly between crossed polarisers by application of a voltage of between 0 and 30 V.

The additives no. 1 to 40 show favourable alignment properties in both LC media with negative $\Delta\epsilon$, M1 and M2.

Mixture Examples 42-80

The compounds 2 to 40 are added analogously to Mixture Example 2 to a nematic LC medium M3 ($\Delta\epsilon>0$) and the mixture is homogenised. The proportions by weight of the compounds in the medium are indicated in Table 5. The resulting LC medium is in all cases introduced into a test cell without pre-alignment layer and has spontaneous homeotropic (vertical) alignment to the substrate surfaces. In the temperature-stable range, the VA-IPS cell can be switched reversibly between crossed polarisers by application of a voltage of between 0 and 20 V.

TABLE 5

Proportions by weight for doping in M3 and alignment of the resulting cell at 20° C. Test cell of the VA-IPS type

| Mixture Example No. | Compound No. | Proportion by weight | Alignment at 20° C./ switchable |
|---|---|---|---|
| 42 | 2 | 0.25% | homeotropic/yes |
| 43 | 3 | 0.25% | homeotropic/yes |
| 44 | 4 | 0.25% | homeotropic/yes |
| 45 | 5 | 0.25% | homeotropic/yes |
| 46 | 6 | 0.25% | homeotropic/yes |
| 47 | 7 | 0.25% | homeotropic/yes |
| 48 | 8 | 0.25% | homeotropic/yes |
| 49 | 9 | 0.25% | homeotropic/yes |
| 50 | 10 | 0.25% | homeotropic/yes |
| 51 | 11 | 0.4% | homeotropic/yes |
| 52 | 12 | 0.4% | homeotropic/yes |
| 53 | 13 | 0.4% | homeotropic/yes |
| 54 | 14 | 0.4% | homeotropic/yes |
| 55 | 15 | 0.35% | homeotropic/yes |
| 56 | 16 | 0.1% | homeotropic/yes |
| 57 | 17 | 0.3% | homeotropic/yes |
| 58 | 18 | 0.15% | homeotropic/yes |
| 59 | 19 | 0.15% | homeotropic/yes |
| 60 | 20 | 0.15% | homeotropic/yes |
| 61 | 21 | 0.15% | homeotropic/yes |
| 62 | 22 | 0.15% | homeotropic/yes |
| 63 | 23 | 0.15% | homeotropic/yes |
| 64 | 24 | 0.15% | homeotropic/yes |
| 65 | 25 | 0.15% | homeotropic/yes |
| 66 | 26 | 0.15% | homeotropic/yes |
| 67 | 27 | 0.2% | homeotropic/yes |
| 68 | 28 | 0.2% | homeotropic/yes |
| 69 | 29 | 0.2% | homeotropic/yes |
| 70 | 30 | 0.2% | homeotropic/yes |
| 71 | 31 | 0.2% | homeotropic/yes |
| 72 | 32 | 0.2% | homeotropic/yes |
| 73 | 33 | 0.2% | homeotropic/yes |
| 74 | 34 | 0.2% | homeotropic/yes |
| 75 | 35 | 0.2% | homeotropic/yes |
| 76 | 36 | 0.2% | homeotropic/yes |
| 77 | 37 | 0.2% | homeotropic/yes |
| 78 | 38 | 0.3% | homeotropic/yes |
| 79 | 39 | 0.2% | homeotropic/yes |
| 80 | 40 | 0.15% | homeotropic/yes |

Mixture Example 81 to 88 (Polymer Stabilisation of Previous Mixture Examples)

A polymerizable compound (RM-1, 0.3% by weight) and a self-aligning compound (5, 0.25% by weight, or 6, 0.25% by weight, or 19, 0.15% by weight, or 21, 0.15% by weight, or 26, 0.15% by weight, or 34, 0.20% by weight or 35, 0.20% by weight) are added to the nematic LC medium M1 ($\Delta\epsilon<0$) and the mixture is homogenised.

Use in Test Cells without Pre-Alignment Layer:

The resulting mixture is introduced into a test cell (without polyimide alignment layer, layer thickness d≈4.0 μm, ITO coating on both sides (structured ITO in case of a multi-domain switching), no passivation layer). The LC medium has spontaneous homeotropic (vertical) alignment to the substrate surfaces. The cell is irradiated with UV light of intensity 100 mW/cm² at 20° C. for 15 min with application of a voltage greater than the optical threshold voltage. This causes polymerization of the monomeric, polymerizable compound. The homeotropic alignment is additionally stabilized, and the pre-tilt is tuned. The resultant PSA-VA cell can be switched reversibly at up to the clearing point with application of a voltage of between 0 and 30 V. The response times are reduced compared to the un-polymerized cell.

Auxiliary substances like Irganox® 1076 (Ciba Specialty Chem.) may be added (e.g. 0.001%) for preventing spontaneous polymerization. A UV-cut filter may be used during polymerization for preventing damage of the mixtures (e.g. 320 or 340 nm UV cut-filter).

Polymerization may also be performed without an applied voltage. After polymerization a passivation layer is formed, without changing the pre-tilt. The passivation layer improves the long-time stability of the self-orientation.

Polymer Stabilisation of Analogous Mixture Experiments

Analogously to Mixture examples 81 to 88, mixtures with RM-1 and the LC medium M2 are performed with compound 5, 6, 19, 26, 34, and 35. Comparable results to Mixture Examples 81 to 88 are obtained.

Variation of the Reactive Mesogen

RM-2, RM-3 and RM-4 are employed (replacing RM-1), with both M1 and M2. Comparable results to Mixture Examples 81 to 88 are obtained.

Heat Load Experiments (Stability of the Self-Orientation of Mixture Examples 3 to 41)

The LC media of the Mixture Examples 3 to 41 are filled into a test cell (without polyimide alignment layer, layer thickness d≈4.0 μm, ITO coating on both sides (structured ITO in case of a multi-domain switching), no passivation layer). The LC medium has spontaneous homeotropic (vertical) alignment to the substrate surfaces. The resulting VA-cell is treated at 120° C. for at least 1 h. After heat-stress, all cells still show high quality of the self-orientation. The compounds are thus compatible with the conditions of a production process used in the display industry.

The invention claimed is:
1. A LC medium comprising a low-molecular-weight liquid-crystalline mixture and one or more self-aligning additives of formula I:

$$R^1\text{-}A^1\text{-}(Z^2\text{-}A^2)_{m1}\text{-}R^2 \quad (I)$$

$R^2$ denotes a group

(A1)

(A2)

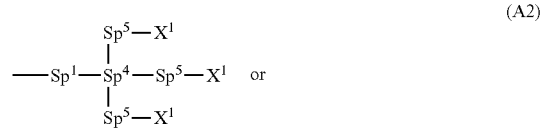

-continued

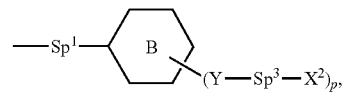

(A3)

$Sp^1$, $Sp^3$, $Sp^5$ independently of each other, denotes a spacer group or a single bond,
$Sp^2$ denotes a trivalent, acyclic spacer group,
$Sp^4$ denotes a tetravalent, acyclic spacer group,
Y is independently of each other O, S, (CO), $NR^0$ or a single bond,
$X^1$ and $X^2$ independently of each other a group —OH, —$NH_2$, —$NHR^{11}$, —SH, —$SR^{11}$, —$NR^{11}_2$, —$OR^{11}$ or —(CO)OH,

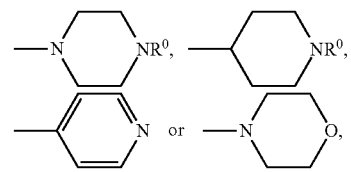

$R^{11}$ in each case independently denotes a halogenated or unsubstituted alkyl chain having 1 to 15 C atoms, in which one or more $CH_2$ groups are each optionally replaced, independently of one another, by —C≡C—, —CH=CH—, —(CO)O—, —O(CO)—, —(CO)— or —O— in such a way that O or N atoms are not linked directly to one another, and where two radicals $R^{11}$ are optionally linked to one another to form a ring,
B a ring or condensed ring, optionally substituted by one, two or three $R^L$,
p is 2, 3, 4 or 5,
$A^1$ and $A^2$ each, independently of one another, denote an aromatic, heteroaromatic, alicyclic or heterocyclic group, which optionally contains fused rings, and which is optionally mono- or polysubstituted by $R^L$,
$R^L$ in each case, independently of one another, denotes OH, SH, $SR^0$, —$(CH_2)_{n1}$—OH, F, Cl, Br, I, —CN, —$NO_2$, —NCO, —NCS, —OCN, —SCN, —C(=O)N($R^0$)$_2$, —C(=O)$R^0$, —N($R^0$)$_2$, —$(CH_2)_{n1}$—N($R^0$)$_2$, optionally substituted silyl, optionally substituted aryl or cycloalkyl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which one or more H atoms are optionally replaced by F or Cl, and two vicinal $R^L$ together are optionally =O,
n1 denotes 1, 2, 3, 4 or 5,
$Z^2$ in each case, independently of one another, denotes a single bond, —O—, —S—, —CO—, —CO—O—, —OCO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CH_2)_{n1}$—, —$CF_2CH_2$—, —$CH_2CF_2$—, —$(CF_2)_{n1}$—, —CH=CH—, —CF=CF—, —C≡C—, —CH=CH—COO—, —OCO—CH=CH— or $CR^0R^{00}$,
$R^0$ and $R^{00}$ each, independently of one another, denote H or alkyl having 1 to 12 C atoms,
$R^1$ denotes H, halogen, straight-chain, branched or cyclic alkyl having 1 to 25 C atoms, in which one or more non-adjacent $CH_2$ groups are optionally replaced by —C≡C, —CH=CH, —$NR^0$—, —O—, —S—, —CO—, —CO—O—, —O—CO—, or —O—CO—O— in such a way that N, O and/or S atoms are not linked directly to one another, and in which one or more tertiary carbon atoms (CH groups) are optionally replaced by N, and in which one or more H atoms are optionally replaced by F or Cl, and m1 denotes 0, 1, 2, 3, 4 or 5.

2. The LC medium according to claim 1, further comprising a polymerizable or polymerized component, where the polymerized component is obtainable by polymerization of a polymerizable component.

3. The LC medium according to claim 1, wherein in the compound of formula I, m1 is 1, 2 or 3.

4. The LC medium according to claim 1, wherein, in the compound of formula I, $R^2$ contains two or three hydroxy groups.

5. The LC medium according to claim 1, wherein in the compound of formula I, $R^2$ comprises two groups $X^1$ or two groups $X^2$.

6. The LC medium according to claim 1, wherein, in the compound of formula I, $A^1$ and $A^2$, if present, are independently 1,4-phenylene and/or cyclohexane-1,4-diyl, which are all optionally substituted by $R^L$.

7. The LC medium according to claim 1, wherein, in the compound of formula I,
Sp² is CH, CR⁰ or N,
Sp⁴ is C, and

denotes a benzene ring.

8. The LC medium according to claim 1, wherein in the compound of formula I
$R^2$ denotes

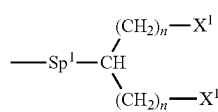  (A1a)

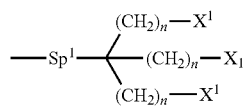  (A2a)

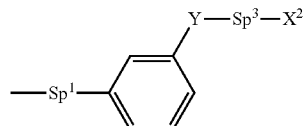  (A3a)

or (A3b)

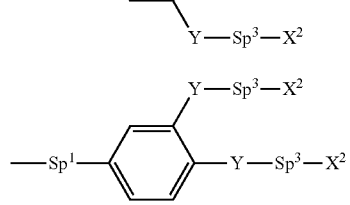

in which Y, $X^1$, $X^2$, $Sp^1$ and $Sp^3$ are independently defined as for the compound of formula I, and
n independently denotes 1, 2, 3 or 4.

9. The LC medium according to claim 1, comprising one or more compounds of the following formulae:

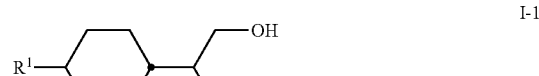  I-1

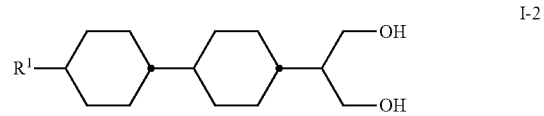  I-2

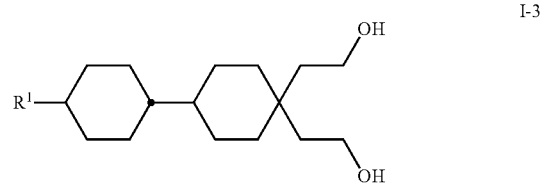  I-3

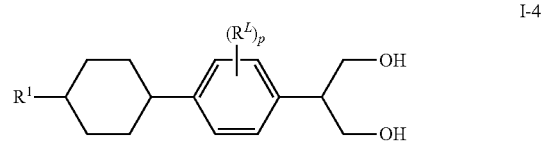  I-4

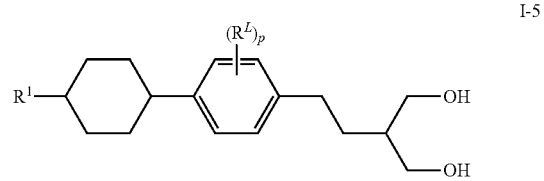  I-5

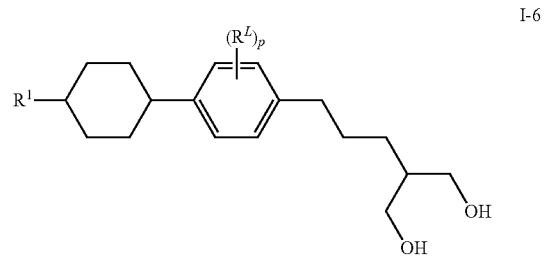  I-6

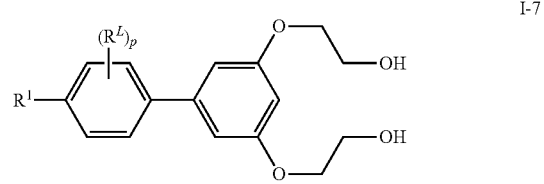  I-7

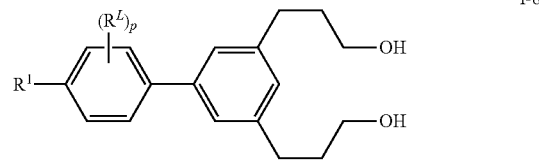  I-8

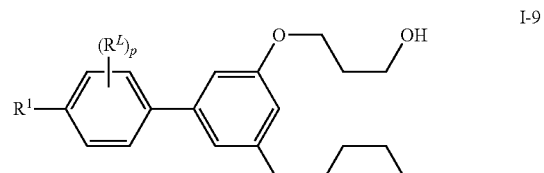  I-9

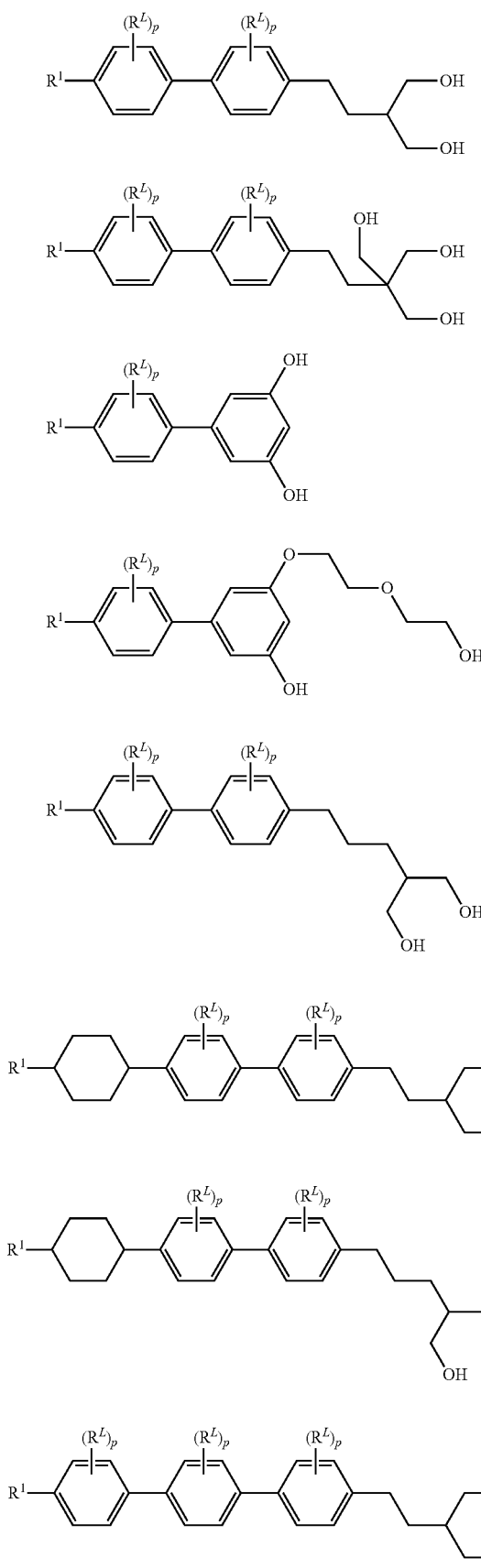
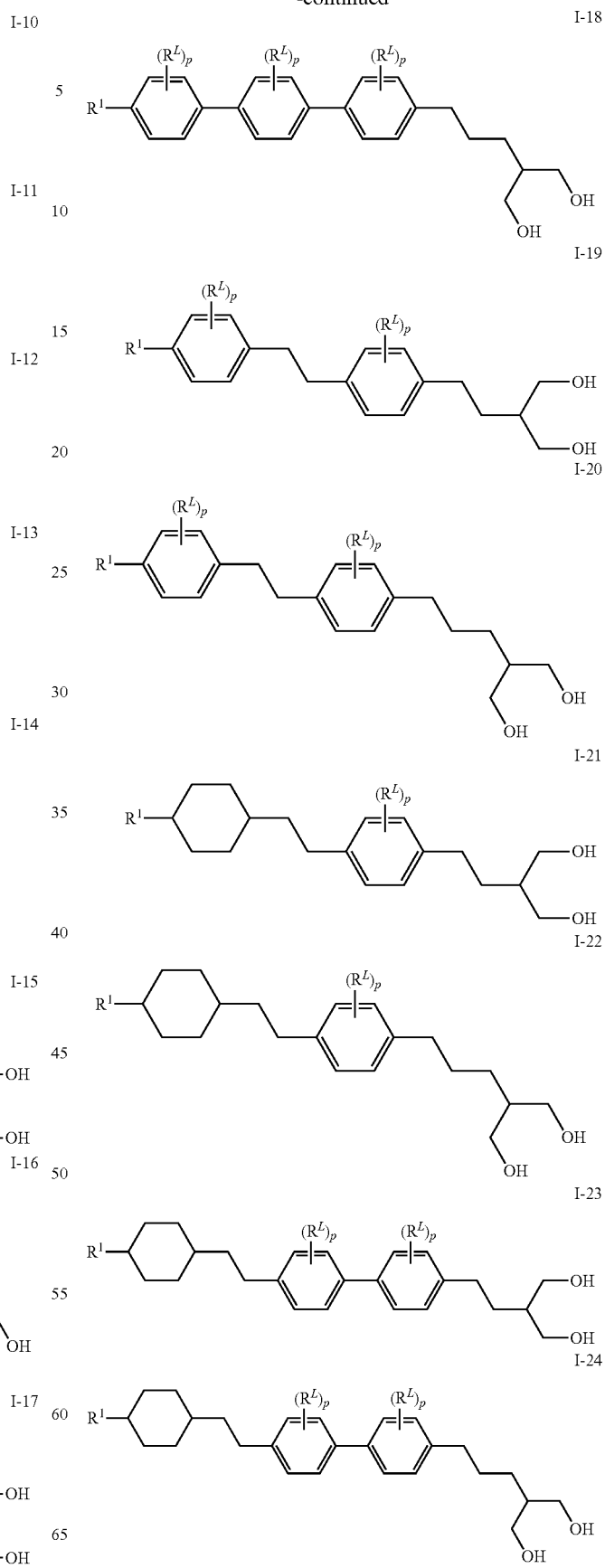

I-25
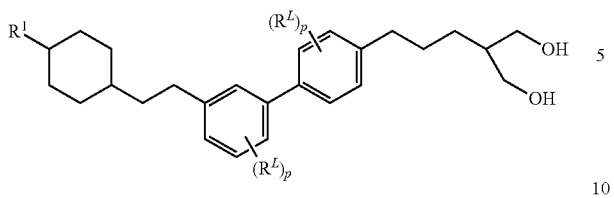

I-26
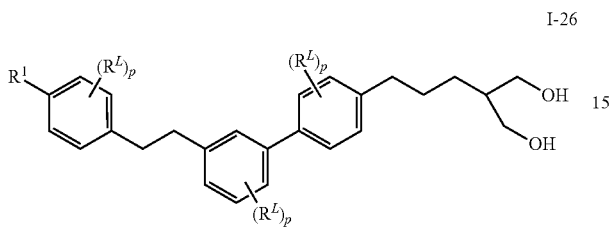

I-27
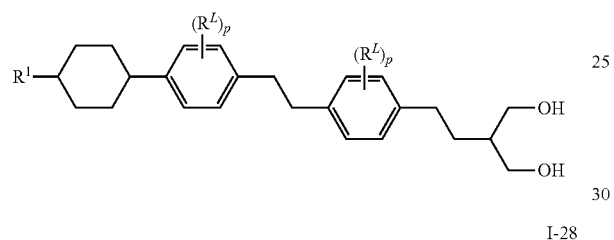

I-28
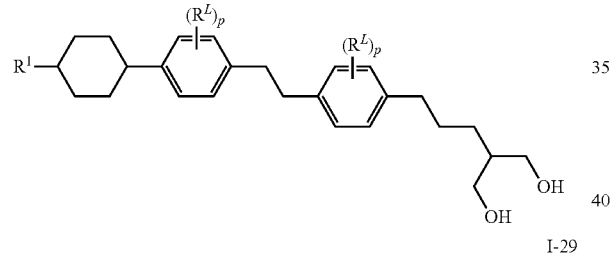

I-29
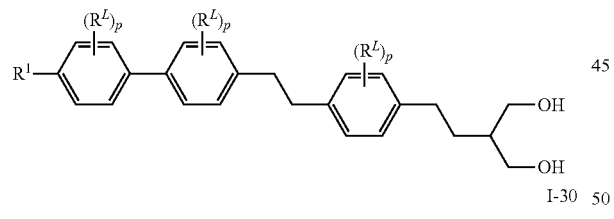

I-30
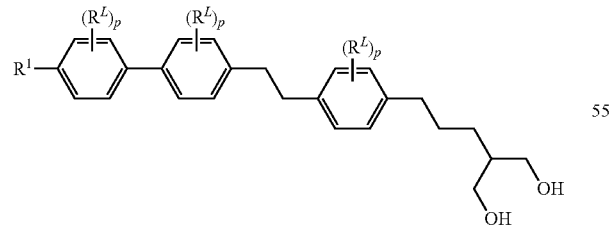

I-31
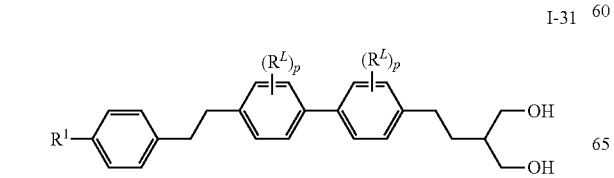

I-32
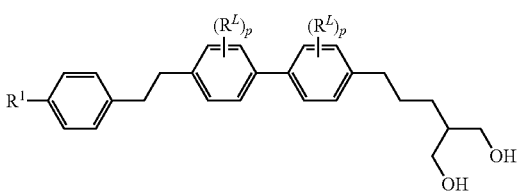

I-33
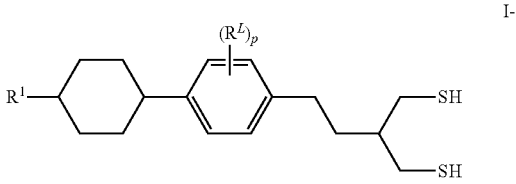

I-34
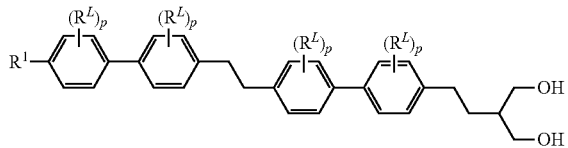

I-35
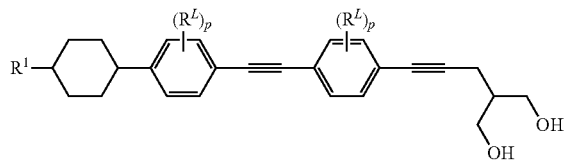

wherein $R^1$, $R^L$ and p are independently defined as for the compound of formula I.

10. The LC medium according to claim 1, comprising the one or more compounds of formula I in a concentration of less than 1% by weight.

11. The LC medium according to claim 1, comprising one or more polymerizable compounds or a polymerized component, which comprises one or more compounds in polymerized form, wherein the one or more polymerizable compounds are of the following formulae:

M1

M2
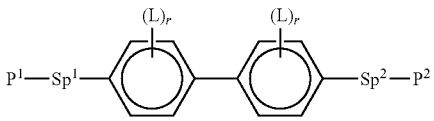

M3
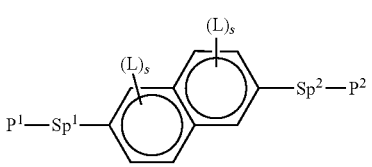

M4
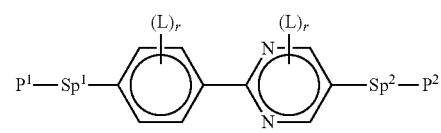
M5
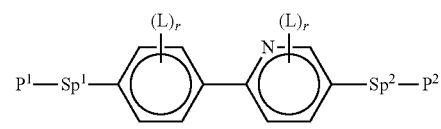
M6
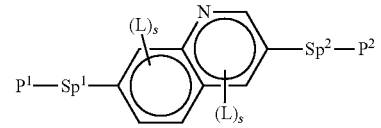
M7
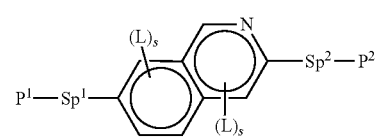
M8
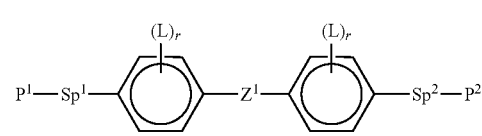
M9
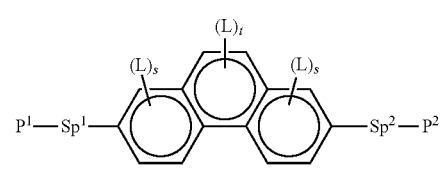
M10
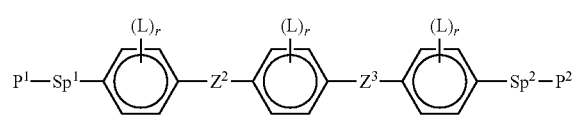
M11
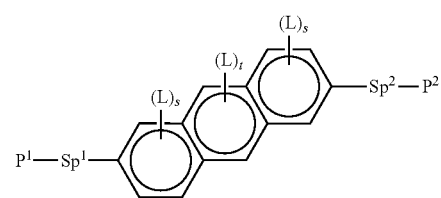
M12
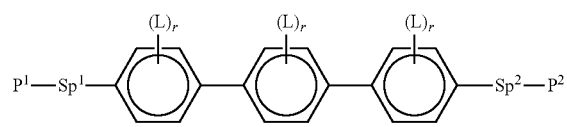
M13
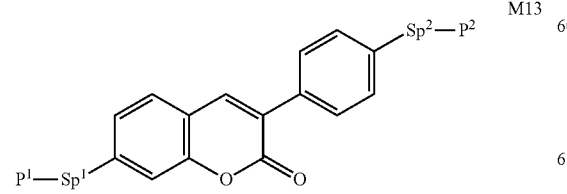
M14
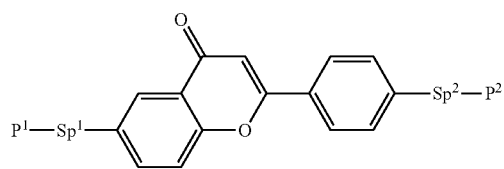
M15
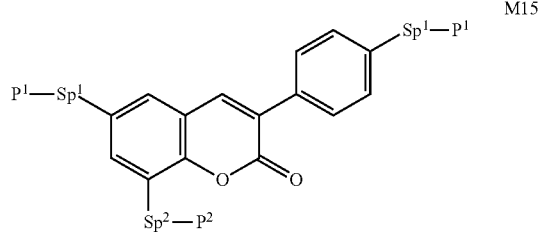
M16
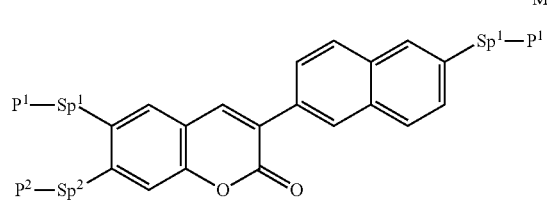
M17
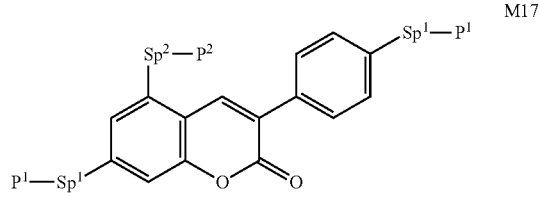
M18
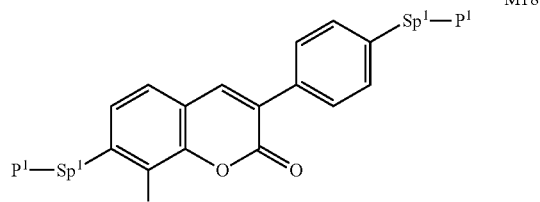
M19
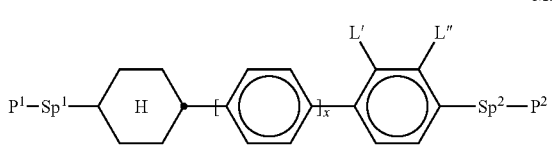
M20
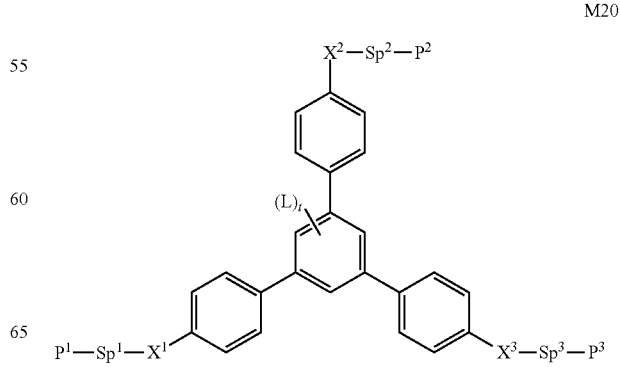

M21–M40 (chemical structure diagrams)

-continued

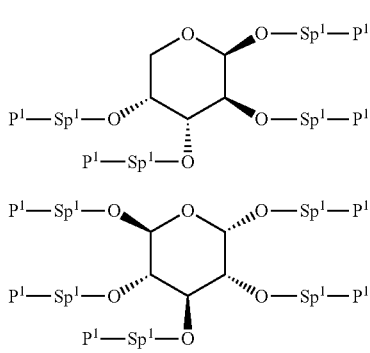

M41

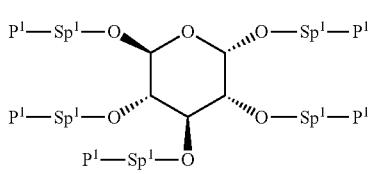

M42 wherein
P¹ and P² each, independently of one another, denote a polymerisable group,
Sp¹ and Sp² each, independently of one another, denote a single bond or a divalent spacer group, where, in addition, one or more of the radicals P¹-Sp¹- and P²—Sp²- optionally denote a radical R$^{aa}$, with the proviso that at least one of the radicals P¹-Sp¹- and P²—Sp²- present does not denote R$^{aa}$,
R$^{aa}$ denotes H, F, Cl, CN or straight-chain or branched alkyl having 1 to 25 C atoms, in which one or more non-adjacent CH₂ groups are each optionally replaced, independently of one another, by C(R⁰)=C(R⁰⁰)—, —C≡C—, —N(R⁰)—, —O—, —S—, —CO—, —CO—O—, —O—CO—, or —O—CO—O— in such a way that O and/or S atoms are not linked directly to one another, and in which one or more H atoms are optionally replaced by F, Cl, CN or P¹—Sp¹-,
R⁰, R⁰⁰ each, independently of one another, denote H or alkyl having 1 to 12 C atoms,
R$^y$ and R$^z$ each, independently of one another, denote H, F, CH₃ or CF₃,
Z¹ denotes —O—, —CO—, —C(R$^y$R$^z$)— or —CF₂CF₂—,
Z² and Z³ each, independently of one another, denote —CO—O—, —O—CO—, —CH₂O—, —OCH₂—, —CF₂O—, —OCF₂— or —(CH₂)$_n$—, where n is 2, 3 or 4,
L on each occurrence, identically or differently, denotes F, Cl, CN, SCN, SF₅ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms,
L' and L" each, independently of one another, denote H, F or Cl,
r denotes 0, 1, 2, 3 or 4,
s denotes 0, 1, 2 or 3,
t denotes 0, 1 or 2, and
x denotes 0 or 1.

12. The LC medium according to claim 1, comprising <5% by weight of polymerizable compounds.

13. An LC display comprising an LC cell having two substrates and at least two electrodes, where at least one substrate is transparent to light and at least one substrate has one or two electrodes, and a layer of an LC medium according to claim 1 located between the substrates, where the compound of the formula I is suitable for effecting homeotropic alignment of the LC medium with respect to the substrate surfaces.

14. The LC display according to claim 13, wherein the substrates have no alignment layers for homeotropic alignment.

15. The LC display according to claim 13, wherein the substrates have unrubbed alignment layers on one or both sides.

16. The LC display according to claim 13, which is a VA display containing an LC medium having negative dielectric anisotropy and electrodes arranged on opposite substrates.

17. The LC display according to claim 13, which is a VA-IPS display containing an LC medium having positive dielectric anisotropy and two electrodes arranged on at least one substrate.

18. A process for preparing a LC medium according to claim 1, comprising mixing together one or more compounds of formula I with a low-molecular-weight liquid-crystalline component or components, and optionally adding one or more polymerizable compounds and/or auxiliary substances.

19. A compound of formula I'

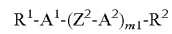

in which
R² denotes

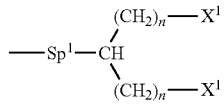

(A1a)

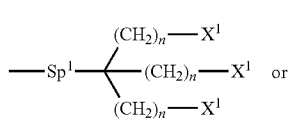

(A2a)

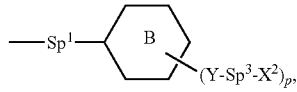

(A3)

n independently denotes 1, 2, 3 or 4,
Sp¹, Sp³, Sp⁵ independently of each other, denotes a spacer group or a single bond,
Sp² denotes a trivalent, acyclic spacer group,
Sp⁴ denotes a tetravalent, acyclic spacer group,
Y is independently of each other O, S, (CO), NR⁰ or a single bond,
X¹ and X² independently of each other a group —OH, —NH₂, —NHR¹¹, —SH, —SR¹¹, —NR¹¹₂, —OR¹¹ or —(CO)OH,

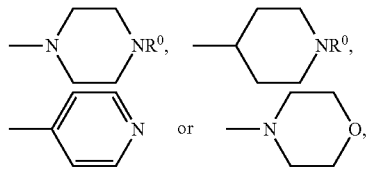

R¹¹ in each case independently denotes a halogenated or unsubstituted alkyl chain having 1 to 15 C atoms, in which one or more CH₂ groups are each optionally replaced, independently of one another, by —C≡C—, —CH=CH—, —(CO)O—, —O(CO)—, —(CO)— or —O— in such a way that O or N atoms are not linked directly to one another, and where two radicals $R^{11}$ are optionally linked to one another to form a ring, B a ring or condensed ring, optionally substituted by one, two or three $R^L$, p is 2, 3, 4 or 5, $A^1$ and $A^2$ each, independently of one another, denote an aromatic, heteroaromatic, alicyclic or heterocyclic group, which optionally contains fused rings, and which is optionally mono- or polysubstituted by $R^L$, $R^L$ in each case, independently of one another, denotes OH, SH, $SR^0$, —$(CH_2)_{n1}$—OH, F, Cl, Br, I, —CN, —$NO_2$, —NCO, —NCS, —OCN, —SCN, —C(=O)N($R^0$)$_2$, —C(=O)$R^0$, —N($R^0$)$_2$, —$(CH_2)_{n1}$—N($R^0$)$_2$, optionally substituted silyl, optionally substituted aryl or cycloalkyl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which one or more H atoms are optionally replaced by F or Cl, and two vicinal $R^L$ together are optionally =O, n1 denotes 1, 2, 3, 4 or 5, $Z^2$ in each case, independently of one another, denotes a single bond, —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—COO—, —OCO—CH=CH— or $CR^0R^{00}$, $R^0$ and $R^{00}$ each, independently of one another, denote H or alkyl having 1 to 12 C atoms, $R^1$ denotes H, halogen, straight-chain, branched or cyclic alkyl having 1 to 25 C atoms, in which one or more non-adjacent CH$_2$ groups are optionally replaced by —C≡C—, —CH=CH, —NR$^0$—, —O—, —S—, —CO—, —CO—O—, —O—CO—, or —O—CO—O— in such a way that N, O and/or S atoms are not linked directly to one another, and in which one or more tertiary carbon atoms (CH groups) are optionally replaced by N, and in which one or more H atoms are optionally replaced by F or Cl, and m1 denotes 1, 2, 3 or 4.

20. The compound according to claim 19, wherein $Sp^1$ is not a single bond.

21. The compound according to claim 19, wherein m1 denotes 1, 2 or 3, and $R^2$ denotes a group of formula

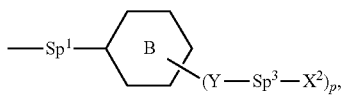

and p, $Sp^1$, ring B, Y, $Sp^3$ and $X^2$ are defined as for the compound of formula I'.

22. A method for effecting homeotropic alignment between two substrates of an LC cell, comprising providing a layer of the LC medium according to claim 1 between the two substrates.

23. A process for preparing a LC display comprising a LC cell having two substrates and at least two electrodes, where at least one substrate is transparent to light and at least one substrate has one or two electrodes, comprising the process steps of:

filling of the cell with the LC medium according to claim 1 and optionally a polymerizable component, and optionally polymerizing the polymerizable component, optionally with application of a voltage to the cell or under the action of an electric field.

24. A compound of formula I'

$$R^1\text{-}A^1\text{-}(Z^2\text{-}A^2)_{m1}\text{-}R^2 \qquad (I')$$

in which $R^2$ denotes a group

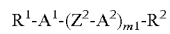 (A1)

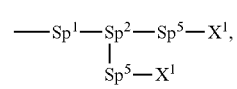 (A2)

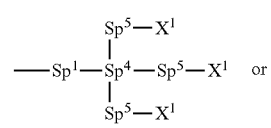 or

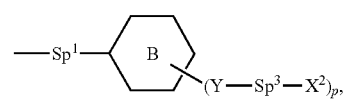 (A3)

$Sp^1$, $Sp^3$, $Sp^5$ independently of each other, denotes a spacer group or a single bond, $Sp^2$ denotes a trivalent, acyclic spacer group, $Sp^4$ denotes a tetravalent, acyclic spacer group, Y is independently of each other O, S, (CO), $NR^0$ or a single bond, $X^1$ and $X^2$ independently of each other a group —OH, —$NH_2$, —$NHR^{11}$, —SH, —$SR^{11}$, —$NR^{11}_2$, —$OR^{11}$ or —(CO)OH,

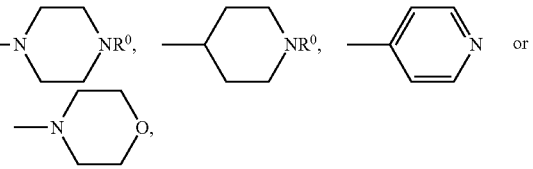

$R^{11}$ in each case independently denotes a halogenated or unsubstituted alkyl chain having 1 to 15 C atoms, in which one or more CH$_2$ groups are each optionally replaced, independently of one another, by —C≡C—, —CH=CH—, —(CO)O—, —O(CO)—, —(CO)— or —O— in such a way that O or N atoms are not linked directly to one another, and where two radicals $R^{11}$ are optionally linked to one another to form a ring, B a ring or condensed ring, optionally substituted by one, two or three $R^L$, p is 2, 3, 4 or 5, $A^1$ and $A^2$ each, independently of one another, denote 1,4-phenylene and/or cyclohexane-1,4-diyl, which is optionally mono- or polysubstituted by $R^L$, $R^L$ in each case, independently of one another, denotes OH, SH, $SR^0$, —$(CH_2)_{n1}$—OH, F, Cl, Br, I, —CN, —$NO_2$, —NCO, —NCS, —OCN, —SCN, —C(=O)N($R^0$)$_2$, —C(=O)$R^0$, —N($R^0$)$_2$, —$(CH_2)_{n1}$—N($R^0$)$_2$, optionally substituted silyl, optionally substituted aryl or cycloalkyl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which one or more H atoms are optionally replaced by F or Cl, and two vicinal $R^L$ together are optionally =O, n1 denotes 1, 2, 3, 4 or 5, $Z^2$ in each case, independently of one another, denotes a single bond, —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—COO—, —OCO—CH=CH— or $CR^0R^{00}$, $R^0$ and $R^{00}$ each, independently of one another, denote H or alkyl having 1 to 12 C atoms, $R^1$ denotes H, halogen, straight-chain, branched or cyclic alkyl having 1 to 25 C atoms, in which one or more non-adjacent CH$_2$ groups are optionally replaced by —C≡C—, —CH=CH—, —NR$^0$—, —O—, —S—, —CO—, —CO—O—, —O—CO—, or —O—CO—O— in such a way that N, O and/or S atoms are not linked directly to one another, and in which one or more tertiary carbon atoms (CH groups) are optionally replaced by N, and in which one or more H atoms are optionally replaced by F or Cl, and m1 denotes 2, 3 or 4.

\* \* \* \* \*